US011578334B2

(12) United States Patent
Nagy

(10) Patent No.: US 11,578,334 B2
(45) Date of Patent: Feb. 14, 2023

(54) TARGETED ENDONUCLEASE ACTIVITY OF THE RNA-GUIDED ENDONUCLEASE CASX IN EUKARYOTES

(71) Applicant: MONSANTO TECHNOLOGY LLC, St. Louis, MO (US)

(72) Inventor: Ervin D. Nagy, Lake St. Louis, MO (US)

(73) Assignee: MONSANTO TECHNOLOGY LLC, St. Louis, MO (US)

( * ) Notice: Subject to any disclaimer, the term of this patent is extended or adjusted under 35 U.S.C. 154(b) by 0 days.

(21) Appl. No.: 16/758,335

(22) PCT Filed: Oct. 24, 2018

(86) PCT No.: PCT/US2018/057325
§ 371 (c)(1),
(2) Date: Apr. 22, 2020

(87) PCT Pub. No.: WO2019/084148
PCT Pub. Date: May 2, 2019

(65) Prior Publication Data
US 2020/0407738 A1  Dec. 31, 2020

Related U.S. Application Data

(60) Provisional application No. 62/577,034, filed on Oct. 25, 2017.

(51) Int. Cl.
*C12N 15/82* (2006.01)

(52) U.S. Cl.
CPC ...... *C12N 15/8213* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | |
|---|---|---|
| 4,897,355 A | 1/1990 | Eppstein et al. |
| 4,946,787 A | 8/1990 | Eppstein et al. |
| 5,049,386 A | 9/1991 | Eppstein et al. |
| 5,106,739 A | 4/1992 | Comai et al. |
| 5,159,135 A | 10/1992 | Umbeck |
| 5,188,958 A | 2/1993 | Moloney et al. |
| 5,322,938 A | 6/1994 | McPherson et al. |
| 5,352,605 A | 10/1994 | Fraley et al. |
| 5,359,142 A | 10/1994 | McPherson et al. |
| 5,378,619 A | 1/1995 | Rogers |
| 5,463,174 A | 10/1995 | Moloney et al. |
| 5,530,196 A | 6/1996 | Fraley et al. |
| 5,538,880 A | 7/1996 | Lundquist et al. |
| 5,550,318 A | 8/1996 | Adams et al. |
| 5,591,616 A | 1/1997 | Hiei et al. |
| 5,641,876 A | 6/1997 | McElroy et al. |
| 5,750,871 A | 5/1998 | Moloney et al. |
| 5,824,877 A | 10/1998 | Hinchee et al. |
| 5,837,848 A | 11/1998 | Ely et al. |
| 5,850,019 A | 12/1998 | Maiti et al. |
| 6,051,753 A | 4/2000 | Comai et al. |
| 6,140,078 A | 10/2000 | Sanders et al. |
| 6,153,812 A | 11/2000 | Fry et al. |
| 6,160,208 A | 12/2000 | Lundquist et al. |
| 6,175,060 B1 | 1/2001 | Lefebvre et al. |
| 6,177,611 B1 | 1/2001 | Rice |
| 6,194,636 B1 | 2/2001 | McElroy et al. |
| 6,232,526 B1 | 5/2001 | McElroy et al. |
| 6,252,138 B1 | 6/2001 | Karimi et al. |
| 6,294,714 B1 | 9/2001 | Matsunaga et al. |
| 6,384,301 B1 | 5/2002 | Martinell et al. |
| 6,399,861 B1 | 6/2002 | Anderson et al. |
| 6,426,446 B1 | 7/2002 | McElroy et al. |
| 6,429,357 B1 | 8/2002 | McElroy et al. |
| 6,429,362 B1 | 8/2002 | Crane |
| 6,433,252 B1 | 8/2002 | Kriz et al. |
| 6,437,217 B1 | 8/2002 | McElroy et al. |
| 6,635,806 B1 | 10/2003 | Kriz et al. |
| 9,116,024 B2 | 8/2015 | Laurent |
| 9,117,424 B2 | 8/2015 | Stem |
| 10,570,415 B2 * | 2/2020 | Doudna ............... C12N 9/1025 |
| 2004/0216189 A1 | 10/2004 | Houmard et al. |
| 2014/0093622 A1 | 4/2014 | Chang |
| 2017/0176529 A1 | 6/2017 | Batra et al. |
| 2017/0198277 A1 | 7/2017 | Kmiec et al. |

(Continued)

FOREIGN PATENT DOCUMENTS

| | | |
|---|---|---|
| WO | WO 91/17424 | 8/2015 |
| WO | WO 2017/147345 A1 | 8/2017 |
| WO | WO 2017/176529 | 10/2017 |
| WO | 2018152418 A1 | 8/2018 |

OTHER PUBLICATIONS

Liu etal 2019 (Nature 566:7743 p. 218-223) (Year: 2019).*
Selkova etal 2020 (RNA Biology 17:10 p. 1472-1479) (Year: 2020).*
Wang etal 2008 (Chinese Science Bulletin 53:20, p. 3185-3190) (Year: 2008).*

(Continued)

*Primary Examiner* — Matthew R Keogh
(74) *Attorney, Agent, or Firm* — Morrison & Foerster LLP

(57) ABSTRACT

This disclosure provides an engineered system comprising: a first nucleic acid molecule encoding a CasX nuclease, and a guide RNA (gRNA) or a second nucleic acid molecule encoding the gRNA, where the first nucleic acid molecule is codon optimized for a eukaryotic cell, and where the gRNA is designed to hybridize with a target site in the eukaryotic cell. Further, this disclosure provides a method of modifying at least one target site in a eukaryotic genome comprising: providing a eukaryotic cell with a CasX nuclease or a first nucleic acid molecule encoding the CasX nuclease, and providing the eukaryotic cell with a guide RNA (gRNA) or a second nucleic acid molecule encoding the gRNA, where the gRNA and the CasX nuclease form a complex, where the gRNA hybridizes to the target site, and where the complex generates a modification at the target site.

7 Claims, 6 Drawing Sheets

Specification includes a Sequence Listing.

(56) References Cited

U.S. PATENT DOCUMENTS

2017/0233756 A1 8/2017 Begemann et al.
2017/0260535 A1* 9/2017 Xu .................... C12N 15/8261

OTHER PUBLICATIONS

Murray et al. 1989 17:2, p. 477-498) (Year: 1989).*
Altschul, et al. "Basic local alignment search tool." *J. Mol. Biol.* 215:403-410 (1990).
Bevan et al., "A chimaeric antibiotic resistance gene as a selectable marker for plant cell transformation," *Nature* 304:184-187, (1983).
Burstein et al. "New CRISPR-Cas systems from uncultivated microbes," *Nature* 542:237-241 (2017).
Chandler et al., "Two regulatory genes of the maize anthocyanin pathway are homologous: isolation of B utilizing R genomic sequences.," The *Plant Cell* 1(12): 1175-1183,(1989).
Chenna et al., "Multiple sequence alignment with the Clustal series of programs," *Nucleic Acids Research* 31: 3497-3500 (2003).
Cook et al., "Copy Number Variation of Multiple Genes at Rhg1 Mediates Nematode Resistance in Soybean," *Science*, 338(6111):1206-1209, (2012).
Depicker et al., "Nopaline synthase: transcript mapping and DNA sequence.," *Journal of Molecular and Applied Genetics*, 1(6): 561-573, (1982).
Ebert et al., "Identification of an essential upstream element in the nopaline synthase promoter by stable and transient assays," *Proceedings of the National Academy of Sciences of the United States*, 84(16):5745-5749 (1987).
Gao et al., "The soybean-Phytophthora resistance locus Rps1-k encompasses coiled coil-nucleotide binding-leucine rich repeat-like genes and repetitive sequences," *BMC Plant Biology*, 8:29 (2008).

International Search Report and Written Opinion, issued in International Patent Application No. PCT/US2018/057325 dated Mar. 1, 2019.
Larkin et al., "Clustal W and Clustal X version 2.0," *Bioinformatics* 23: 2947-48 (2007).
Lawton et al., "Expression of a soybean β-conclycinin gene under the control of the Cauliflower Mosaic Virus 35S and 19S promoters in transformed petunia tissues," *Plant Molecular Biology* 9: 315-324, (1987).
Murray et al., "Codon usage in plant genes," *Nucleic Acids Research*, 17(2):477-98, (1989).
Nakamura et al., "Codon usage tabulated from international DNA sequence databases: status for the year 2000," *Nucleic Acids Research*, 28(1):292 (2000).
Odell et al., "Identification of DNA sequences required for activity of the cauliflower mosaic virus 35S promoter," *Nature*, 313: 810-812, (1985).
Yang et al., "Maize sucrose synthase-1 promoter directs phloem cell-specific expression of Gus gene in transgenic tobacco plants.," *Proceedings of the National Academy of Sciences, USA*, 87(11): 4144-4148, (1990).
Yang et al., "New CRISPR-Cas systems discovered," Cell Res., 27:313-314 (2017).
Begemann, M. B et al. (2017) "Characterization and Validation of a Novel Group of Type V, Class 2 Nucleases for in vivo Genome Editing," bioRxiv, 9 pages, retrieved on Jan. 4, 2022 from https://www.biorxiv.org/content/10.1101/192799v2.
Yang, H. et al. (2019) "CasX: a new and small CRISPR gene-editing protein," Cell Research, 29:345-346.

* cited by examiner

Rhg1 TS3 AND FLANKING SEQUENCE
SEQ ID NO:29

5' TGTCCCACAAAATGAATTTTGCATGTATTCAGTGCTTCCTTCTTCGGGCTTCACTTTTTCTGGCCGGTGCAGCCGGTAACCAGTAGT 3'

*Figure 1A*

INSERTION EVENT 1
SEQ ID NO:30

5' TGTCCCACAAAATGAATTTTGCATGTATTCAGTGCTTCCTTCTTCGGGTAATATAGCGTAACTATAACGGTCCTAAGGTAGC 3'

TARGETED ENDONUCLEASE ACTIVITY OF THE RNA-GUIDED ENDONUCLEASE CASX IN EUKARYOTES

CROSS-REFERENCE TO RELATED APPLICATIONS

This application is a U.S. National Stage of International Application No. PCT/US2018/057325, filed Oct. 24, 2018, which claims the benefit of U.S. Provisional Application No. 62/577,034, filed Oct. 25, 2017, both of which are incorporated by reference in their entireties herein.

FIELD

The present disclosure relates to compositions and methods related to using CasX enzymes in eukaryotic cells.

INCORPORATION OF SEQUENCE LISTING

A sequence listing contained in the file named "P34546US01_Corrected_SEQ.TXT" which is 112,753 bytes (measured in MS-Windows®) and created on Sep. 8, 2020, is filed electronically herewith and incorporated by reference in its entirety.

BACKGROUND

RNA-guided endonucleases can be used as tools for genome editing. However, their versatility is limited by restrictions imposed by several requirements, including short recognition motifs referred to as protospacer-adjacent motifs (PAMs) and the fact that some RNA-guided nucleases either exhibit no functionality or greatly reduced functionality in eukaryotic organisms.

CasX was recently discovered to be able to specifically cut plasmid DNA in the bacteria *Escherichia coli*. See Burstein et al., 2017, *Nature*, 542:237-241. However, it was unknown whether CasX can be reprogrammed to a) function in a eukaryotic cell, and b) whether CasX can cut chromosomal DNA.

The inventors of the present disclosure have discovered that CasX can be modified to successfully edit a eukaryotic genome.

BRIEF DESCRIPTION OF DRAWINGS

FIG. 1, which comprises 1A and 1B, schematically depicts the targeted integration of a short, double-stranded donor oligonucleotide into a target site within Rhg1 locus in the soy genome using an engineered CasX RNA guided endo-nuclease system. FIG. 1A shows the nucleotide sequence of the Rhg1_TS3 locus along with the 5' and 3' flanking regions (SEQ ID NO: 29). The Target site is shown in bold and the PAM site is underlined. FIG. 1B depicts the nucleotide sequence from a portion of the amplicon obtained from Insertion event 1 (SEQ ID NO:30). The genomic sequence is represented by a black bar, and the donor oligo sequence (SEQ ID NO: 21) is represented by a gray bar.

FIG. 6 shows representative amplicons with targeted deletions at the three soy Rhg1 target sites when targeted by DsCasX_Gm and cognate guide RNA. No sequences matching the search criteria were found in negative controls lacking DsCasX_Gm. Underlined sequence denotes PAM. Arrows indicate the position of the 20 bp region downstream of PAM. Nucleotides shown in gray bar indicate the query site (18-24 bp downstream of PAM).

SUMMARY

Figure 2:
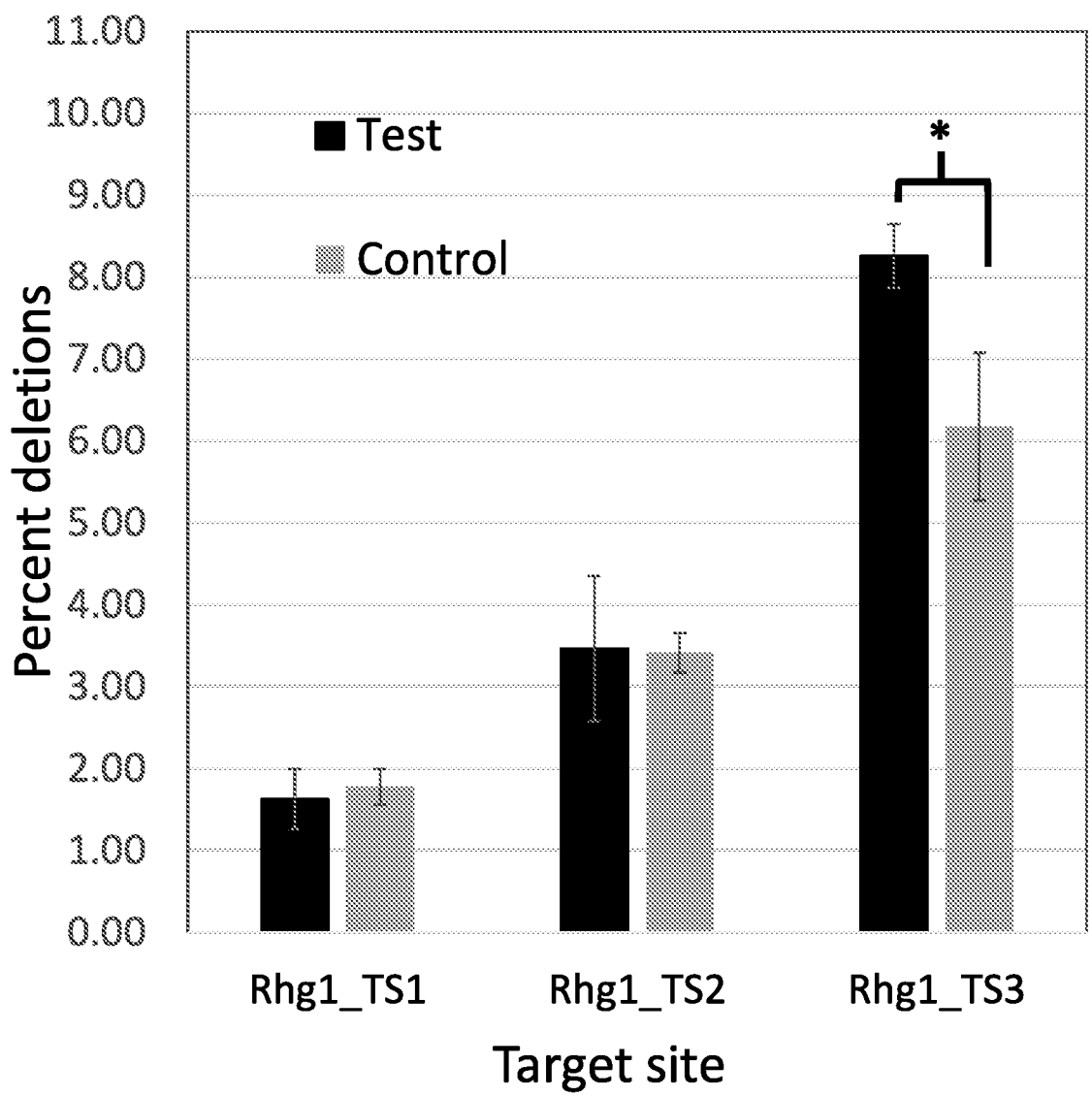
FIG. 2 shows the percentage of targeted deletions induced by DsCasX_Gm at three target sites within the Rhg1 locus in soy as determined by targeted deep sequencing. Test samples were treated with DsCasX_Gm nuclease while the Control samples lacked DsCasX_Gm. Data are represented as the mean of three biological replicates. Error bars represent one standard deviation. Statistical significance was determined using a Student's T-test, and * indicates P<0.05.

In one aspect, this disclosure provides a method of modifying at least one target site in a eukaryotic genome comprising: providing a eukaryotic cell with a CasX nuclease or a first nucleic acid molecule encoding the CasX nuclease, and providing the eukaryotic cell with a guide RNA (gRNA) or a second nucleic acid molecule encoding the gRNA, where the gRNA and the CasX nuclease form a complex, where the gRNA hybridizes to the target site, and where the complex generates a modification at the target site.

In one aspect, this disclosure provides an engineered system comprising: (a) a first nucleic acid molecule encoding a CasX nuclease, and (b) a guide RNA (gRNA) or a second nucleic acid molecule encoding the gRNA, where the first nucleic acid molecule is codon optimized for a eukaryotic cell, and where the gRNA is designed to hybridize with a target site in the eukaryotic cell.

In one aspect, this disclosure provides a plant cell comprising an engineered system comprising: (a) a first nucleic acid molecule encoding a CasX nuclease, and (b) a guide RNA (gRNA) or a second nucleic acid molecule encoding the gRNA, where the first nucleic acid molecule is codon optimized for the plant cell, and where the gRNA is designed to hybridize with a target site in the plant cell.

Several embodiments relate to a method of modifying at least one target site in a eukaryotic genome comprising: providing a eukaryotic cell with a CasX nuclease or a first nucleic acid encoding said CasX nuclease, and providing said eukaryotic cell with a guide RNA (gRNA) or a second nucleic acid encoding said gRNA, wherein said gRNA and said CasX nuclease form a complex in the eukaryotic cell, wherein said gRNA hybridizes to said target site, and wherein said complex generates a modification at said target site. In some embodiments, the gRNA is a single guide RNA (sgRNA). In some embodiments, the first nucleic acid comprises a promoter capable of expressing the nucleic acid molecule encoding the CasX nuclease in the eukaryotic cell. In some embodiments, the second nucleic acid comprises a promoter capable of expressing the nucleic acid molecule encoding the gRNA in the eukaryotic cell. In some embodiments, the CasX nuclease modifies the eukaryotic genome by generating a single-stranded break. In some embodiments, the CasX nuclease modifies the eukaryotic genome by generating a single-stranded break 18-24 nucleotides 3' of a PAM site. In some embodiments, the CasX nuclease modifies the eukaryotic genome by generating a double-stranded break. In some embodiments, the CasX nuclease modifies the eukaryotic genome by generating a double-stranded break 18-24 nucleotides 3' of a PAM site. In some embodiments, the eukaryotic cell is an animal cell. In some embodiments, the eukaryotic cell is a plant cell. In some embodiments, the eukaryotic cell is a plant cell is selected from the group consisting of a corn cell, a cotton cell, a canola cell, a soybean cell, a rice cell, a tomato cell, a wheat cell, an alfalfa cell, a sorghum cell, an *Arabidopsis* cell, a cucumber cell, a potato cell, a *brassica* cell, a monocot cell, a dicot cell, and an algae cell. In some embodiments, the first nucleic acid is codon optimized for expression in a eukaryotic cell. In some embodiments, the first nucleic acid is codon optimized for expression in a plant cell. In some embodiments, the first nucleic acid is codon optimized for expression in a soybean cell. In some embodiments, the first nucleic acid is codon optimized for expression in a corn cell. In some embodiments, the gRNA comprises a crRNA. In some embodiments, the gRNA comprises a tracrRNA. In some embodiments, the gRNA comprises a pentaloop sequence. In some embodiments, the gRNA comprises a variable spacer sequence. In some embodiments, the gRNA comprises a repeat sequence. In some embodiments, the eukaryotic genome comprises at least two, at least three, at least four, at least five, at least six, at least seven, at least eight, at least nine, or at least ten target sites. In some embodiments, the CasX nuclease comprises an amino acid sequence at least 80% identity to SEQ ID NO: 1 or 60. In some embodiments, the CasX nuclease further comprises a nuclear localization signal. In some embodiments, the CasX nuclease is encoded by a nucleic acid comprising at least 80% identity to the sequence of SEQ ID NO: 2 or 61. In some embodiments, the CasX nuclease is encoded by a nucleic acid comprising at least 80% identity to a sequence selected from the group consisting of SEQ ID NO: 3 and 79. In some embodiments, the CasX nuclease is encoded by a nucleic acid comprising at least 80% identity to a sequence selected from the group consisting of SEQ ID NO: 39, 62 and 80. In some embodiments, the CasX nuclease is encoded by a nucleic acid comprising at least 80% identity to a sequence selected from the group consisting of SEQ ID NOs: 9, 44, and 64. In some embodiments, the first nucleic acid encoding the CasX nuclease comprises an intron. In some embodiments, the CasX nuclease is from a bacteria phyla selected from the group consisting of Deltaproteobacteria and Planctomycetes. In some embodiments, the first nucleic acid comprises a promoter selected from the group consisting of a constitutive promoter, a tissue-specific promoter, a tissue-preferred promoter, and an inducible promoter. In some embodiments, the second nucleic acid comprises a promoter selected from the group consisting of a constitutive promoter, a tissue-specific promoter, a tissue-preferred promoter, and an inducible promoter. In some embodiments, the promoter is encoded by a nucleic acid molecule comprising the sequence of SEQ ID NO: 7, or a functional fragment thereof. In some embodiments, the promoter is encoded by a nucleic acid molecule comprising the sequence of SEQ ID NO: 17, or a functional fragment thereof. In some embodiments, the first and/or second nucleic acid comprises a terminator sequence. In some embodiments, a donor molecule is provided to the eukaryotic cell. In some embodiments, the donor molecule is inserted into said target site. In some embodiments, the target site is within 17-25 nucleotides of a protospacer adjacent motif (PAM). In some embodiments, the PAM comprises a sequence of TTCN. In some embodiments, the first and second nucleic acids are provided in a single vector. In some embodiments, the first and second nucleic acids are provided in separate vectors. In some embodiments, the first and second nucleic acids are encoded by a single nucleic acid molecule. In some embodiments, the first and second nucleic acids are encoded by a separate nucleic acid molecules. In some embodiments, the first and second nucleic acids are provided to the eukaryotic cell by *Agrobacterium*-mediated transformation. In some embodiments, the first and second nucleic acids are provided to the eukaryotic cell by polyethylene glycol-mediated transformation. In some embodiments, the CasX nuclease is provided to the eukaryotic cell by biolistic transformation. In some embodiments, the guide RNA is provided to the eukaryotic cell by biolistic transformation. In some embodiments, the CasX nuclease is provided to the eukaryotic cell by particle delivery. In some embodiments, the CasX nuclease is provided to the eukaryotic cell by a delivery vesicle. In some embodiments, the delivery vesicle is selected from the group consisting of an exosome and a liposome. In some embodiments, the first and/or second nucleic acids are provided to the eukaryotic cell by a viral vector. In some embodiments, the viral vector is selected from the group consisting of an adenovirus vector, a lentivirus vector, and an adeno-associated viral vector.

Several embodiments relate to a system comprising: a first nucleic acid encoding a CasX nuclease, and a guide RNA (gRNA) or a second nucleic acid molecule encoding said gRNA, wherein the first nucleic acid molecule is codon optimized for expression in a eukaryotic cell, and wherein said gRNA is designed to hybridize with a target site in the eukaryotic cell. In some embodiments, the gRNA is a sgRNA. In some embodiments, the first nucleic acid comprises a promoter capable of expressing the nucleic acid molecule encoding the CasX nuclease in the eukaryotic cell. In some embodiments, the second nucleic acid comprises a promoter capable of expressing the nucleic acid molecule encoding the gRNA in the eukaryotic cell. In some embodiments, the system generates a single-stranded break in the genome of the eukaryotic cell. In some embodiments, the system generates a single-stranded break 18-24 nucleotides 3' of a PAM site. In some embodiments, the system generates a double-stranded break in the genome of the eukaryotic cell. In some embodiments, the system generates a double-stranded break 18-24 nucleotides 3' of a PAM site. In some embodiments, the PAM comprises a sequence of TTCN. In some embodiments, the eukaryotic cell is an animal cell. In some embodiments, the eukaryotic cell is a plant cell. In some embodiments, the eukaryotic cell is a plant cell is selected from the group consisting of a corn cell, a cotton cell, a canola cell, a soybean cell, a rice cell, a tomato cell, a wheat cell, an alfalfa cell, a sorghum cell, an *Arabidopsis* cell, a cucumber cell, a potato cell, a *brassica* cell, a monocot cell, a dicot cell, and an algae cell. In some embodiments, the first nucleic acid is codon optimized for expression in a eukaryotic cell. In some embodiments, the first nucleic acid is codon optimized for expression in a plant cell. In some embodiments, the first nucleic acid is codon optimized for expression in a soybean cell. In some embodiments, the first nucleic acid is codon optimized for expression in a corn cell. In some embodiments, the gRNA comprises a crRNA. In some embodiments, the gRNA comprises a tracrRNA. In some embodiments, the gRNA comprises a pentaloop sequence. In some embodiments, the gRNA comprises a variable spacer sequence. In some embodiments, the gRNA comprises a repeat sequence. In some embodiments, the first nucleic acid encodes a CasX nuclease comprising an amino acid sequence at least 80% identity to SEQ ID NO: 1 or 60. In some embodiments, the first nucleic acid encodes a CasX nuclease further comprising a nuclear localization signal. In some embodiments, the first nucleic acid comprises a nucleic acid sequence having at least 80% identity to the sequence of SEQ ID NO: 2 or 61. In some embodiments, the first nucleic acid comprises a nucleic acid sequence having at least 80% identity to a sequence selected from the group consisting of SEQ ID NO: 3 and 79. In some embodiments, the first nucleic acid comprises a nucleic acid sequence having at least 80% identity to a sequence selected from the group consisting of SEQ ID NO: 39, 62 and 80. In some embodiments, the first nucleic acid comprises a nucleic acid sequence having at least 80% identity to a sequence selected from the group consisting of SEQ ID NOs: 9, 44, and 64. In some embodiments, the first nucleic acid encoding the CasX nuclease comprises an intron. In some embodiments, the CasX nuclease is from a bacteria phyla selected from the group consisting of Deltaproteobacteria and Planctomycetes. In some embodiments, the first nucleic acid comprises a promoter selected from the group consisting of a constitutive promoter, a tissue-specific promoter, a tissue-preferred promoter, and an inducible promoter. In some embodiments, the second nucleic acid comprises a promoter selected from the group consisting of a constitutive promoter, a tissue-specific promoter, a tissue-preferred promoter, and an inducible promoter. In some embodiments, the promoter is encoded by a nucleic acid molecule comprising the sequence of SEQ ID NO: 7, or a functional fragment thereof. In some embodiments, the promoter is encoded by a nucleic acid molecule comprising the sequence of SEQ ID NO: 17, or a functional fragment thereof. In some embodiments, the first and/or second nucleic acid comprises a terminator sequence. In some embodiments, the system further comprises a donor molecule. In some embodiments, the donor molecule is inserted into the target site. In some embodiments, the target site is within 17-25 nucleotides of a protospacer adjacent motif (PAM). In some embodiments, the PAM comprises a sequence of TTCN. In some embodiments, the first and second nucleic acids are provided in a single vector. In some embodiments, the first and second nucleic acids are provided in separate vectors. In some embodiments, the first and second nucleic acids are encoded by a single nucleic acid molecule. In some embodiments, the first and second nucleic acids are encoded by a separate nucleic acid molecules. In some embodiments, the first and second nucleic acids are provided to the eukaryotic cell by *Agrobacterium*-mediated transformation. In some embodiments, the first and second nucleic acids are provided to the eukaryotic cell by polyethylene glycol-mediated transformation. In some embodiments, the CasX nuclease is provided to the eukaryotic cell by biolistic transformation. In some embodiments, the guide RNA is provided to the eukaryotic cell by biolistic transformation. In some embodiments, the first and/or second nucleic acids are provided to the eukaryotic cell by a viral vector. In some embodiments, the viral vector is selected from the group consisting of an adenovirus vector, a lentivirus vector, and an adeno-associated viral vector.

Several embodiments relate to a system comprising: a CasX nuclease, and a guide RNA (gRNA) or a nucleic acid molecule encoding said gRNA, wherein said gRNA is designed to hybridize with a target site in the eukaryotic cell. In some embodiments, the gRNA is a sgRNA. In some embodiments, the system generates a single-stranded break in the genome of the eukaryotic cell. In some embodiments, the system generates a single-stranded break 18-24 nucleotides 3' of a PAM site. In some embodiments, the system generates a double-stranded break in the genome of the eukaryotic cell. In some embodiments, the system generates a double-stranded break 18-24 nucleotides 3' of a PAM site. In some embodiments, the PAM comprises a sequence of TTCN. In some embodiments, the eukaryotic cell is an animal cell. In some embodiments, the eukaryotic cell is a plant cell. In some embodiments, the eukaryotic cell is a plant cell is selected from the group consisting of a corn cell, a cotton cell, a canola cell, a soybean cell, a rice cell, a tomato cell, a wheat cell, an alfalfa cell, a sorghum cell, an *Arabidopsis* cell, a cucumber cell, a potato cell, a *brassica* cell, a monocot cell, a dicot cell, and an algae cell. In some embodiments, the first nucleic acid is codon optimized for expression in a eukaryotic cell. In some embodiments, the gRNA comprises a crRNA. In some embodiments, the gRNA comprises a tracrRNA. In some embodiments, the gRNA comprises a pentaloop sequence. In some embodiments, the gRNA comprises a variable spacer sequence. In some embodiments, the gRNA comprises a repeat sequence. In some embodiments, the CasX nuclease amino acid sequence has at least 80% identity to SEQ ID NO: 1 or 60. In some embodiments, the CasX nuclease further comprising a nuclear localization signal. In some embodiments, the CasX nuclease is from a bacteria phyla selected from the group consisting of Deltaproteobacteria and Planctomycetes. In some embodiments, the system further comprises a donor molecule. In some embodiments, the donor molecule is inserted into the target site. In some embodiments, the target site is within 17-25 nucleotides of a protospacer adjacent motif (PAM). In some embodiments, the PAM comprises a sequence of TTCN.

Several embodiments relate to a plant cell comprising an engineered system comprising: a first nucleic acid encoding a CasX nuclease, and a guide RNA (gRNA) or a second nucleic acid encoding said gRNA, wherein said first nucleic acid molecule is codon optimized for said plant cell, and wherein said gRNA is designed to hybridize with a target site in said plant cell. In some embodiments, the first nucleic acid comprises a promoter capable of expressing the nucleic acid molecule encoding the CasX nuclease in the plant cell. In some embodiments, the second nucleic acid comprises a promoter capable of expressing the nucleic acid molecule encoding the gRNA in the plant cell. In some embodiments, the system generates a single-stranded break in the genome of the plant cell. In some embodiments, the system generates a single-stranded break 18-24 nucleotides 3' of a PAM site. In some embodiments, the system generates a double-stranded break in the genome of the plant cell. In some embodiments, the system generates a double-stranded break 18-24 nucleotides 3' of a PAM site. In some embodiments, the PAM comprises a sequence of TTCN. In some embodiments, the plant cell is selected from the group consisting of a corn cell, a cotton cell, a canola cell, a soybean cell, a rice cell, a tomato cell, a wheat cell, an alfalfa cell, a sorghum cell, an *Arabidopsis* cell, a cucumber cell, a potato cell, a *brassica* cell, a monocot cell, a dicot cell, and an algae cell. In some embodiments, the first nucleic acid is codon optimized for expression in a soybean cell. In some embodiments, the first nucleic acid is codon optimized for expression in a corn cell. In some embodiments, the gRNA comprises a crRNA. In some embodiments, the gRNA comprises a tracrRNA. In some embodiments, the gRNA comprises a pentaloop sequence. In some embodiments, the gRNA comprises a variable spacer sequence. In some embodiments, the gRNA comprises a repeat sequence. In some embodiments, the first nucleic acid encodes a CasX nuclease comprising an amino acid sequence at least 80% identity to SEQ ID NO: 1 or 60. In some embodiments, the first nucleic acid encodes a CasX nuclease further comprising a nuclear localization signal. In some embodiments, the first nucleic acid comprises a nucleic acid sequence having at least 80% identity to the sequence of SEQ ID NO: 2 or 61. In some embodiments, the first nucleic acid comprises a nucleic acid sequence having at least 80% identity to a sequence selected from the group consisting of SEQ ID NO: 3 and 79. In some embodiments, the first nucleic acid comprises a nucleic acid sequence having at least 80% identity to a sequence selected from the group consisting of SEQ ID NO: 39, 62 and 80. In some embodiments, the first nucleic acid comprises a nucleic acid sequence having at least 80% identity to a sequence selected from the group consisting of SEQ ID NOs: 9, 44, and 64. In some embodiments, the first nucleic acid encoding the CasX nuclease comprises an intron. In some embodiments, the CasX nuclease is from a bacteria phyla selected from the group consisting of Deltaproteobacteria and Planctomycetes. In some embodiments, the first nucleic acid comprises a promoter selected from the group consisting of a constitutive promoter, a tissue-specific promoter, a tissue-preferred promoter, and an inducible promoter. In some embodiments, the second nucleic acid comprises a promoter selected from the group consisting of a constitutive promoter, a tissue-specific promoter, a tissue-preferred promoter, and an inducible promoter. In some embodiments, the promoter is encoded by a nucleic acid molecule comprising the sequence of SEQ ID NO: 7, or a functional fragment thereof. In some embodiments, the promoter is encoded by a nucleic acid molecule comprising the sequence of SEQ ID NO: 17, or a functional fragment thereof. In some embodiments, the first and/or second nucleic acid comprises a terminator sequence. In some embodiments, the system further comprises a donor molecule. In some embodiments, the donor molecule is inserted into the target site. In some embodiments, the target site is within 17-25 nucleotides of a protospacer adjacent motif (PAM). In some embodiments, the PAM comprises a sequence of TTCN. In some embodiments, the first and second nucleic acids are provided in a single vector. In some embodiments, the first and second nucleic acids are provided in separate vectors. In some embodiments, the first and second nucleic acids are encoded by a single nucleic acid molecule. In some embodiments, the first and second nucleic acids are encoded by a separate nucleic acid molecules. In some embodiments, the first and second nucleic acids are provided to the plant cell by *Agrobacterium*-mediated transformation. In some embodiments, the first and second nucleic acids are provided to the plant cell by polyethylene glycol-mediated transformation. In some embodiments, the CasX nuclease is provided to the plant cell by biolistic transformation. In some embodiments, the guide RNA is provided to the plant cell by biolistic transformation. In some embodiments, the first and/or second nucleic acids are provided to the plant cell by a viral vector. In some embodiments, the viral vector is selected from the group consisting of an adenovirus vector, a lentivirus vector, and an adeno-associated viral vector.

Several embodiments relate to a plant cell comprising an engineered system comprising: a CasX nuclease, and a guide RNA (gRNA) or a nucleic acid encoding said gRNA, wherein said first nucleic acid molecule is codon optimized for said plant cell, and wherein said gRNA is designed to hybridize with a target site in said plant cell. In some embodiments, the gRNA is a sgRNA. In some embodiments, the system generates a single-stranded break in the genome of the plant cell. In some embodiments, the system generates a single-stranded break 18-24 nucleotides 3' of a PAM site. In some embodiments, the system generates a double-stranded break in the genome of the plant cell. In some embodiments, the system generates a double-stranded break 18-24 nucleotides 3' of a PAM site. In some embodiments, the PAM comprises a sequence of TTCN. In some embodiments, the plant cell is selected from the group consisting of a corn cell, a cotton cell, a canola cell, a soybean cell, a rice cell, a tomato cell, a wheat cell, an alfalfa cell, a sorghum cell, an *Arabidopsis* cell, a cucumber cell, a potato cell, a *brassica* cell, a monocot cell, a dicot cell, and an algae cell. In some embodiments, the gRNA comprises a crRNA. In some embodiments, the gRNA comprises a tracrRNA. In some embodiments, the gRNA comprises a pentaloop sequence. In some embodiments, the gRNA comprises a variable spacer sequence. In some embodiments, the gRNA comprises a repeat sequence. In some embodiments, the CasX nuclease amino acid sequence has at least 80% identity to SEQ ID NO: 1 or 60. In some embodiments, the CasX nuclease further comprising a nuclear localization signal. In some embodiments, the CasX nuclease is from a bacteria phyla selected from the group consisting of Deltaproteobacteria and Planctomycetes. In some embodiments, the system further comprises a donor molecule. In some embodiments, the donor molecule is inserted into the target site. In some embodiments, the target site is within 17-25 nucleotides of a protospacer adjacent motif (PAM). In some embodiments, the PAM comprises a sequence of TTCN.

DETAILED DESCRIPTION

Unless defined otherwise, all technical and scientific terms used have the same meaning as commonly understood by one of ordinary skill in the art to which this disclosure belongs. Where a term is provided in the singular, the inventors also contemplate aspects of the disclosure described by the plural of that term. Where there are discrepancies in terms and definitions used in references that are incorporated by reference, the terms used in this application shall have the definitions given herein. Other technical terms used have their ordinary meaning in the art in which they are used, as exemplified by various art-specific dictionaries, for example, "The American Heritage® Science Dictionary" (Editors of the American Heritage Dictionaries, 2011, Houghton Mifflin Harcourt, Boston and New York), the "McGraw-Hill Dictionary of Scientific and Technical Terms" (6th edition, 2002, McGraw-Hill, New York), or the "Oxford Dictionary of Biology" (6th edition, 2008, Oxford University Press, Oxford and New York). The inventors do not intend to be limited to a mechanism or mode of action. Reference thereto is provided for illustrative purposes only.

The practice of the compositions and methods described in this disclosure includes, unless otherwise indicated, conventional techniques of biochemistry, chemistry, molecular biology, microbiology, cell biology, plant biology, genomics, biotechnology, and genetics, which are within the skill of the art. See, for example, Green and Sambrook, Molecular Cloning: A Laboratory Manual, 4th edition (2012); Current Protocols In Molecular Biology (F. M. Ausubel, et al. eds., (1987)); Plant Breeding Methodology (N. F. Jensen, Wiley-Interscience (1988)); the series Methods In Enzymology (Academic Press, Inc.): PCR 2: A Practical Approach (M. J. MacPherson, B. D. Hames and G. R. Taylor eds. (1995)); Harlow and Lane, eds. (1988) Antibodies, A Laboratory Manual; Animal Cell Culture (R. I. Freshney, ed. (1987)); Recombinant Protein Purification: Principles And Methods, 18-1142-75, GE Healthcare Life Sciences; C. N. Stewart, A. Touraev, V. Citovsky, T. Tzfira eds. (2011) Plant Transformation Technologies (Wiley-Blackwell); and R. H. Smith (2013) Plant Tissue Culture: Techniques and Experiments (Academic Press, Inc.).

Any references cited herein, including, e.g., all patents, published patent applications, and non-patent publications, are incorporated herein by reference in their entirety.

When a grouping of alternatives is presented, any and all combinations of the members that make up that grouping of alternatives is specifically envisioned. For example, if an item is selected from a group consisting of A, B, C, and D, the inventors specifically envision each alternative individually (e.g., A alone, B alone, etc.), as well as combinations such as A, B, and D; A and C; B and C; etc.

As used herein, terms in the singular and the singular forms "a," "an," and "the," for example, include plural referents unless the content clearly dictates otherwise.

As used herein, a "mutation" refers to an insertion, deletion, substitution, duplication, or inversion of one or more amino acids or nucleotides as compared to a reference amino acid sequence or to a reference nucleotide sequence.

Any composition, nucleic acid molecule, polypeptide, cell, etc. provided herein is envisioned for use with any method provided herein.

CasX is a type of class 2 CRISPR-Cas nuclease that has been identified in the bacterial phyla Deltaproteobacteria and Planctomycetes. Although CasX was previously shown to be able to cleave plasmid DNA in the bacteria *E. coli* (see Burstein et al. *Nature,* 2017, 542:237-241, which is incorporated herein by reference in its entirety), it is unknown whether CasX can function in a eukaryotic cell. Several CRISPR-Cas system nucleases are known to be non-functional in eukaryotic cells. While not being limited by any particular scientific theory, a CasX nuclease forms a complex with a guide RNA (gRNA), which hybridizes with a complementary target site, thereby guiding the CasX nuclease to the target site. In class 2 CRISPR-Cas systems, CRISPR arrays, including spacers, are transcribed during encounters with recognized invasive DNA and are processed into small interfering CRISPR RNAs (crRNAs). The crRNA comprises a repeat sequence which and a spacer sequence which is complementary to a specific protospacer sequence in an invading pathogen. The spacer sequence can be designed to be complementary to target sequences in a eukaryotic genome. Cas endonucleases associate with their respective crRNAs in their active forms. CasX, similar to the class 2 endonuclease Cas9, requires another non-coding RNA component, referred to as a trans-activating crRNA (tracrRNA), to have functional activity. Nucleic acid molecules provided herein can combine a crRNA and a tracrRNA into one nucleic acid molecule in what is herein referred to as a "single guide RNA" (sgRNA). The gRNA guides the active CasX complex to a target site, where CasX can cleave the target site. A prerequisite for cleavage of the target site by a CasX/gRNA complex is the presence of a conserved protospacer adjacent motif (PAM) near the target site, which usually has the sequence 5'-TTCN-3' for CasX. Alternatively, a PAM for CasX can be 5'-TTCA-3' or 5'-TTC-3'.

In an aspect, this disclosure provides a method of modifying at least one target site in a eukaryotic genome comprising: (a) providing a eukaryotic cell with a CasX nuclease, and (b) providing the eukaryotic cell with a single guide RNA (sgRNA), where the sgRNA and the CasX nuclease form a complex, where the sgRNA hybridizes to the target site, and where the complex generates a modification at the target site. In an aspect, a modification comprises a single-stranded break in a eukaryotic genome. In one aspect, a CasX protein provided herein comprises a nuclease domain capable of generating a single-stranded break in a eukaryotic genome. In an aspect, a CasX protein capable of generating a single-stranded break comprises one or more mutations as compared to a protein comprising a sequence selected from the group consisting of SEQ ID NOs: 1 and 60. In another aspect, a CasX protein provided herein comprises a nuclease domain capable of generating a double-stranded break in a eukaryotic genome. In another aspect, a modification comprises a double-stranded break in a eukaryotic genome. In an aspect, a modification provided herein occurs in vivo. In a further aspect, a modification provided herein occurs ex vivo. In another aspect, a modification provided herein occurs in vitro. In an aspect, a modification comprises one or more nucleotide insertions, deletions, or substitutions located about 20 nucleotides from PAM site.

In another aspect, this disclosure provides a method of modifying at least one target site in a eukaryotic genome comprising: (a) providing a eukaryotic cell with a nucleic acid molecule encoding a CasX nuclease, and (b) providing the eukaryotic cell with a nucleic acid molecule encoding a single guide RNA (sgRNA), where the sgRNA and the CasX nuclease form a complex, where the sgRNA hybridizes to said target site, and where the complex generates a modification at the target site.

In another aspect, this disclosure provides a method of modifying at least one target site in a eukaryotic genome comprising: (a) providing a eukaryotic cell with a nucleic acid molecule comprising a first promoter operably linked to a sequence encoding a CasX nuclease, and (b) providing the eukaryotic cell with a nucleic acid molecule comprising a second promoter operably linked to a sequence encoding a single guide RNA (sgRNA), where the sgRNA and the CasX nuclease form a complex, where the sgRNA hybridizes to the target site, and where the complex generates a modification at said target site.

In a further aspect, this disclosure provides a method of modifying at least one target site in a eukaryotic genome comprising: (a) providing a eukaryotic cell with a CasX nuclease or a nucleic acid molecule encoding said CasX nuclease, and (b) providing the eukaryotic cell with a single guide RNA (sgRNA) or a nucleic acid molecule encoding the sgRNA, where the sgRNA and the CasX nuclease form a complex, where the sgRNA hybridizes to the target site, and where the complex generates a modification at said target site.

In an aspect, this disclosure provides a method of modifying at least one target site in a eukaryotic genome comprising: (a) providing a eukaryotic cell with a CasX nuclease, and (b) providing said eukaryotic cell with a guide RNA (gRNA), where the gRNA and the CasX nuclease form a complex, where the gRNA hybridizes to said target site, and where the complex generates a modification at the target site.

In an aspect, this disclosure provides a method of modifying at least one target site in a eukaryotic genome comprising: (a) providing a eukaryotic cell with a nucleic acid molecule encoding a CasX nuclease, and (b) providing the eukaryotic cell with a nucleic acid molecule encoding a guide RNA (gRNA), where the gRNA and the CasX nuclease form a complex, where the gRNA hybridizes to said target site, and where the complex generates a modification at the target site.

In an aspect, this disclosure provides a method of modifying at least one target site in a eukaryotic genome comprising: (a) providing a eukaryotic cell with a nucleic acid molecule comprising a first promoter operably linked to a sequence encoding a CasX nuclease, and (b) providing said eukaryotic cell with a nucleic acid molecule comprising a second promoter operably linked to a sequence encoding a guide RNA (gRNA), where the gRNA and the CasX nuclease form a complex, where the gRNA hybridizes to said target site, and where the complex generates a modification at the target site.

In an aspect, this disclosure provides a method of modifying at least one target site in a eukaryotic genome comprising: (a) providing a eukaryotic cell with a CasX nuclease or a nucleic acid molecule encoding the CasX nuclease, and (b) providing the eukaryotic cell with a guide RNA (gRNA) or a nucleic acid molecule encoding the gRNA, where the gRNA and the CasX nuclease form a complex, where the gRNA hybridizes to the target site, and where the complex generates a modification at the target site.

In a further aspect, this disclosure provides an engineered system comprising: (a) a first nucleic acid molecule encoding a CasX nuclease, and (b) a guide RNA (gRNA) or a second nucleic acid molecule encoding the gRNA, where the first nucleic acid molecule is codon optimized for a eukaryotic cell, and where the gRNA is designed to hybridize with at least one target site in the eukaryotic cell.

In an aspect, this disclosure also provides an engineered system comprising: (a) a first nucleic acid molecule encoding a CasX nuclease, and (b) a single guide RNA (sgRNA) or a second nucleic acid molecule encoding the sgRNA, where the first nucleic acid molecule is codon optimized for a eukaryotic cell, and where the sgRNA is designed to hybridize with at least one target site in said eukaryotic cell.

In an aspect, a first nucleic acid encoding a CasX nuclease and a second nucleic acid encoding a sgRNA are encoded by a single nucleic acid molecule. In an aspect, a first nucleic acid encoding a CasX nuclease and a second nucleic acid encoding a sgRNA are encoded by separate nucleic acid molecules. In an aspect, a first nucleic acid encoding a CasX nuclease and a second nucleic acid encoding a sgRNA are encoded by a single recombinant vector. In an aspect, a first nucleic acid encoding a CasX nuclease and a second nucleic acid encoding a sgRNA are encoded by separate recombinant vectors.

In an aspect, a CasX nuclease is provided to a eukaryotic cell as a protein. In another aspect, a CasX nuclease is provided to a eukaryotic cell as a protein in a complex with a sgRNA. In a further aspect, a nucleic acid molecule encoding a CasX nuclease is provided to a eukaryotic cell.

In an aspect, a CasX protein provided herein can be expressed from a recombinant vector in vivo. In an aspect, a CasX protein provided herein can be expressed from a recombinant vector in vitro. In an aspect, a CasX protein provided herein can be expressed from a recombinant vector ex vivo. In an aspect, a CasX protein provided herein can be expressed from a nucleic acid molecule in vivo. In an aspect, a CasX protein provided herein can be expressed from a nucleic acid molecule in vitro. In an aspect, a CasX protein provided herein can be expressed from a nucleic acid molecule ex vivo. In another aspect, a CasX protein provided herein can be synthetically synthesized.

In an aspect, a sgRNA provided herein can be expressed from a recombinant vector in vivo. In an aspect, a sgRNA provided herein can be expressed from a recombinant vector in vitro. In an aspect, a sgRNA provided herein can be expressed from a recombinant vector ex vivo. In an aspect, a sgRNA provided herein can be expressed from a nucleic acid molecule in vivo. In an aspect, a sgRNA provided herein can be expressed from a nucleic acid molecule in vitro. In an aspect, a sgRNA provided herein can be expressed from a nucleic acid molecule ex vivo. In another aspect, a sgRNA provided herein can be synthetically synthesized.

In an aspect, a guide RNA (gRNA) provided herein can be expressed from a recombinant vector in vivo. In an aspect, a gRNA provided herein can be expressed from a recombinant vector in vitro. In an aspect, a gRNA provided herein can be expressed from a recombinant vector ex vivo. In an aspect, a gRNA provided herein can be expressed from a nucleic acid molecule in vivo. In an aspect, a gRNA provided herein can be expressed from a nucleic acid molecule in vitro. In an aspect, a gRNA provided herein can be expressed from a nucleic acid molecule ex vivo. In another aspect, a gRNA provided herein can be synthetically synthesized.

The use of the term "polynucleotide" or "nucleic acid molecule" is not intended to limit the present disclosure to polynucleotides comprising deoxyribonucleic acid (DNA). For example, ribonucleic acid (RNA) molecules are also envisioned. Those of ordinary skill in the art will recognize that polynucleotides and nucleic acid molecules can comprise ribonucleotides and combinations of ribonucleotides and deoxyribonucleotides. Such deoxyribonucleotides and ribonucleotides include both naturally occurring molecules and synthetic analogues. The polynucleotides of the present disclosure also encompass all forms of sequences including, but not limited to, single-stranded forms, double-stranded forms, hairpins, stem-and-loop structures, and the like. In an aspect, a nucleic acid molecule provided herein is a DNA molecule. In another aspect, a nucleic acid molecule provided herein is an RNA molecule. In an aspect, a nucleic acid molecule provided herein is single-stranded. In another aspect, a nucleic acid molecule provided herein is double-stranded.

As used herein, the term "polypeptide" refers to a chain of at least two covalently linked amino acids. Polypeptides can be encoded by polynucleotides provided herein. An example of a polypeptide is a protein. Proteins provided herein can be encoded by nucleic acid molecules provided herein.

Nucleic acids can be isolated using techniques routine in the art. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides. Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

Without being limiting, nucleic acids can be detected using hybridization. Hybridization between nucleic acids is discussed in detail in Sambrook et al. (1989, Molecular Cloning: A Laboratory Manual, 2nd Ed., Cold Spring Harbor Laboratory Press, Cold Spring Harbor, N.Y.).

Polypeptides can be detected using antibodies. Techniques for detecting polypeptides using antibodies include enzyme linked immunosorbent assays (ELISAs), Western blots, immunoprecipitations and immunofluorescence. An antibody provided herein can be a polyclonal antibody or a monoclonal antibody. An antibody having specific binding affinity for a polypeptide provided herein can be generated using methods well known in the art. An antibody provided herein can be attached to a solid support such as a microtiter plate using methods known in the art.

The terms "percent identity" or "percent identical" as used herein in reference to two or more nucleotide or protein sequences is calculated by (i) comparing two optimally aligned sequences (nucleotide or protein) over a window of comparison, (ii) determining the number of positions at which the identical nucleic acid base (for nucleotide sequences) or amino acid residue (for proteins) occurs in both sequences to yield the number of matched positions, (iii) dividing the number of matched positions by the total number of positions in the window of comparison, and then (iv) multiplying this quotient by 100% to yield the percent identity. If the "percent identity" is being calculated in relation to a reference sequence without a particular comparison window being specified, then the percent identity is determined by dividing the number of matched positions over the region of alignment by the total length of the reference sequence. Accordingly, for purposes of the present application, when two sequences (query and subject) are optimally aligned (with allowance for gaps in their alignment), the "percent identity" for the query sequence is equal to the number of identical positions between the two sequences divided by the total number of positions in the query sequence over its length (or a comparison window), which is then multiplied by 100%. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity can be adjusted upwards to correct for the conservative nature of the substitution. Sequences that differ by such conservative substitutions are said to have "sequence similarity" or "similarity."

For optimal alignment of sequences to calculate their percent identity, various pair-wise or multiple sequence alignment algorithms and programs are known in the art, such as ClustalW or Basic Local Alignment Search Tool® (BLAST), etc., that can be used to compare the sequence identity or similarity between two or more nucleotide or protein sequences. Although other alignment and comparison methods are known in the art, the alignment and percent identity between two sequences (including the percent identity ranges described above) can be as determined by the ClustalW algorithm, see, e.g., Chenna R. et al., "Multiple sequence alignment with the Clustal series of programs," *Nucleic Acids Research* 31: 3497-3500 (2003); Thompson J D et al., "Clustal W: Improving the sensitivity of progressive multiple sequence alignment through sequence weighting, position-specific gap penalties and weight matrix choice," *Nucleic Acids Research* 22: 4673-4680 (1994); Larkin M A et al., "Clustal W and Clustal X version 2.0," *Bioinformatics* 23: 2947-48 (2007); and Altschul, S. F., Gish, W., Miller, W., Myers, E. W. & Lipman, D. J. (1990) "Basic local alignment search tool." *J. Mol. Biol.* 215:403-410 (1990), the entire contents and disclosures of which are incorporated herein by reference.

The terms "percent complementarity" or "percent complementary" as used herein in reference to two nucleotide sequences is similar to the concept of percent identity but refers to the percentage of nucleotides of a query sequence that optimally base-pair or hybridize to nucleotides a subject sequence when the query and subject sequences are linearly arranged and optimally base paired without secondary folding structures, such as loops, stems or hairpins. Such a percent complementarity can be between two DNA strands, two RNA strands, or a DNA strand and a RNA strand. The "percent complementarity" can be calculated by (i) optimally base-pairing or hybridizing the two nucleotide sequences in a linear and fully extended arrangement (i.e., without folding or secondary structures) over a window of comparison, (ii) determining the number of positions that base-pair between the two sequences over the window of comparison to yield the number of complementary positions, (iii) dividing the number of complementary positions by the total number of positions in the window of comparison, and (iv) multiplying this quotient by 100% to yield the percent complementarity of the two sequences. Optimal base pairing of two sequences can be determined based on the known pairings of nucleotide bases, such as G-C, A-T, and A-U, through hydrogen binding. If the "percent complementarity" is being calculated in relation to a reference sequence without specifying a particular comparison window, then the percent identity is determined by dividing the number of complementary positions between the two linear sequences by the total length of the reference sequence. Thus, for purposes of the present application, when two sequences (query and subject) are optimally base-paired (with allowance for mismatches or non-base-paired nucleotides), the "percent complementarity" for the query sequence is equal to the number of base-paired positions between the two sequences divided by the total number of positions in the query sequence over its length, which is then multiplied by 100%.

In an aspect, a CasX nuclease provided herein comprises an amino acid sequence at least 80% identical to SEQ ID NO: 1. In an aspect, a CasX nuclease provided herein comprises an amino acid sequence at least 85% identical to SEQ ID NO: 1. In an aspect, a CasX nuclease provided herein comprises an amino acid sequence at least 90% identical to SEQ ID NO: 1. In an aspect, a CasX nuclease provided herein comprises an amino acid sequence at least 91% identical to SEQ ID NO: 1. In an aspect, a CasX nuclease provided herein comprises an amino acid sequence at least 92% identical to SEQ ID NO: 1. In an aspect, a CasX nuclease provided herein comprises an amino acid sequence at least 93% identical to SEQ ID NO: 1. In an aspect, a CasX nuclease provided herein comprises an amino acid sequence at least 94% identical to SEQ ID NO: 1. In an aspect, a CasX nuclease provided herein comprises an amino acid sequence at least 95% identical to SEQ ID NO: 1. In an aspect, a CasX nuclease provided herein comprises an amino acid sequence at least 96% identical to SEQ ID NO: 1. In an aspect, a CasX nuclease provided herein comprises an amino acid sequence at least 97% identical to SEQ ID NO: 1. In an aspect, a CasX nuclease provided herein comprises an amino acid sequence at least 98% identical to SEQ ID NO: 1. In an aspect, a CasX nuclease provided herein comprises an amino acid sequence at least 99% identical to SEQ ID NO: 1. In an aspect, a CasX nuclease provided herein comprises an amino acid sequence 100% identical to SEQ ID NO: 1.

In an aspect, a CasX nuclease provided herein comprises an amino acid sequence at least 80% similar to SEQ ID NO: 1. In an aspect, a CasX nuclease provided herein comprises an amino acid sequence at least 85% similar to SEQ ID NO: 1. In an aspect, a CasX nuclease provided herein comprises an amino acid sequence at least 90% similar to SEQ ID NO: 1. In an aspect, a CasX nuclease provided herein comprises an amino acid sequence at least 91% similar to SEQ ID NO: 1. In an aspect, a CasX nuclease provided herein comprises an amino acid sequence at least 92% similar to SEQ ID NO: 1. In an aspect, a CasX nuclease provided herein comprises an amino acid sequence at least 93% similar to SEQ ID NO: 1. In an aspect, a CasX nuclease provided herein comprises an amino acid sequence at least 94% similar to SEQ ID NO: 1. In an aspect, a CasX nuclease provided herein comprises an amino acid sequence at least 95% similar to SEQ ID NO: 1. In an aspect, a CasX nuclease provided herein comprises an amino acid sequence at least 96% similar to SEQ ID NO: 1. In an aspect, a CasX nuclease provided herein comprises an amino acid sequence at least 97% similar to SEQ ID NO: 1. In an aspect, a CasX nuclease provided herein comprises an amino acid sequence at least 98% similar to SEQ ID NO: 1. In an aspect, a CasX nuclease provided herein comprises an amino acid sequence at least 99% similar to SEQ ID NO: 1. In an aspect, a CasX nuclease provided herein comprises an amino acid sequence 100% similar to SEQ ID NO: 1.

In an aspect, a nucleic acid molecule provided herein encodes a CasX protein comprising an amino acid sequence at least 80% identical to SEQ ID NO: 1. In an aspect, a nucleic acid molecule provided herein encodes a CasX protein comprising an amino acid sequence at least 85% identical to SEQ ID NO: 1. In an aspect, a nucleic acid molecule provided herein encodes a CasX protein comprising an amino acid sequence at least 90% identical to SEQ ID NO: 1. In an aspect, a nucleic acid molecule provided herein encodes a CasX protein comprising an amino acid sequence at least 91% identical to SEQ ID NO: 1. In an aspect, a nucleic acid molecule provided herein encodes a CasX protein comprising an amino acid sequence at least 92% identical to SEQ ID NO: 1. In an aspect, a nucleic acid molecule provided herein encodes a CasX protein comprising an amino acid sequence at least 93% identical to SEQ ID NO: 1. In an aspect, a nucleic acid molecule provided herein encodes a CasX protein comprising an amino acid sequence at least 94% identical to SEQ ID NO: 1. In an aspect, a nucleic acid molecule provided herein encodes a CasX protein comprising an amino acid sequence at least 95% identical to SEQ ID NO: 1. In an aspect, a nucleic acid molecule provided herein encodes a CasX protein comprising an amino acid sequence at least 96% identical to SEQ ID NO: 1. In an aspect, a nucleic acid molecule provided herein encodes a CasX protein comprising an amino acid sequence at least 97% identical to SEQ ID NO: 1. In an aspect, a nucleic acid molecule provided herein encodes a CasX protein comprising an amino acid sequence at least 98% identical to SEQ ID NO: 1. In an aspect, a nucleic acid molecule provided herein encodes a CasX protein comprising an amino acid sequence at least 99% identical to SEQ ID NO: 1. In an aspect, a nucleic acid molecule provided herein encodes a CasX protein comprising an amino acid sequence 100% identical to SEQ ID NO: 1.

In an aspect, a nucleic acid molecule provided herein encodes a CasX protein comprising an amino acid sequence at least 80% similar to SEQ ID NO: 1. In an aspect, a nucleic acid molecule provided herein encodes a CasX protein comprising an amino acid sequence at least 85% similar to SEQ ID NO: 1. In an aspect, a nucleic acid molecule provided herein encodes a CasX protein comprising an amino acid sequence at least 90% similar to SEQ ID NO: 1. In an aspect, a nucleic acid molecule provided herein encodes a CasX protein comprising an amino acid sequence at least 91% similar to SEQ ID NO: 1. In an aspect, a nucleic acid molecule provided herein encodes a CasX protein comprising an amino acid sequence at least 92% similar to SEQ ID NO: 1. In an aspect, a nucleic acid molecule provided herein encodes a CasX protein comprising an amino acid sequence at least 93% similar to SEQ ID NO: 1. In an aspect, a nucleic acid molecule provided herein encodes a CasX protein comprising an amino acid sequence at least 94% similar to SEQ ID NO: 1. In an aspect, a nucleic acid molecule provided herein encodes a CasX protein comprising an amino acid sequence at least 95% similar to SEQ ID NO: 1. In an aspect, a nucleic acid molecule provided herein encodes a CasX protein comprising an amino acid sequence at least 96% similar to SEQ ID NO: 1. In an aspect, a nucleic acid molecule provided herein encodes a CasX protein comprising an amino acid sequence at least 97% similar to SEQ ID NO: 1. In an aspect, a nucleic acid molecule provided herein encodes a CasX protein comprising an amino acid sequence at least 98% similar to SEQ ID NO: 1. In an aspect, a nucleic acid molecule provided herein encodes a CasX protein comprising an amino acid sequence at least 99% similar to SEQ ID NO: 1. In an aspect, a nucleic acid molecule provided herein encodes a CasX protein comprising an amino acid sequence 100% similar to SEQ ID NO: 1.

In an aspect, a CasX nuclease provided herein comprises an amino acid sequence at least 80% identical to SEQ ID NO: 60. In an aspect, a CasX nuclease provided herein comprises an amino acid sequence at least 85% identical to SEQ ID NO: 60. In an aspect, a CasX nuclease provided herein comprises an amino acid sequence at least 90% identical to SEQ ID NO: 60. In an aspect, a CasX nuclease provided herein comprises an amino acid sequence at least 91% identical to SEQ ID NO: 60. In an aspect, a CasX nuclease provided herein comprises an amino acid sequence at least 92% identical to SEQ ID NO: 60. In an aspect, a CasX nuclease provided herein comprises an amino acid sequence at least 93% identical to SEQ ID NO: 60. In an aspect, a CasX nuclease provided herein comprises an amino acid sequence at least 94% identical to SEQ ID NO: 60. In an aspect, a CasX nuclease provided herein comprises an amino acid sequence at least 95% identical to SEQ ID NO: 60. In an aspect, a CasX nuclease provided herein comprises an amino acid sequence at least 96% identical to SEQ ID NO: 60. In an aspect, a CasX nuclease provided herein comprises an amino acid sequence at least 97% identical to SEQ ID NO: 60. In an aspect, a CasX nuclease provided herein comprises an amino acid sequence at least 98% identical to SEQ ID NO: 60. In an aspect, a CasX nuclease provided herein comprises an amino acid sequence at least 99% identical to SEQ ID NO: 60. In an aspect, a CasX nuclease provided herein comprises an amino acid sequence 100% identical to SEQ ID NO: 60.

In an aspect, a CasX nuclease provided herein comprises an amino acid sequence at least 80% similar to SEQ ID NO: 60. In an aspect, a CasX nuclease provided herein comprises an amino acid sequence at least 85% similar to SEQ ID NO: 60. In an aspect, a CasX nuclease provided herein comprises an amino acid sequence at least 90% similar to SEQ ID NO: 60. In an aspect, a CasX nuclease provided herein comprises an amino acid sequence at least 91% similar to SEQ ID NO: 60. In an aspect, a CasX nuclease provided herein comprises an amino acid sequence at least 92% similar to SEQ ID NO: 60. In an aspect, a CasX nuclease provided herein comprises an amino acid sequence at least 93% similar to SEQ ID NO: 60. In an aspect, a CasX nuclease provided herein comprises an amino acid sequence at least 94% similar to SEQ ID NO: 60. In an aspect, a CasX nuclease provided herein comprises an amino acid sequence at least 95% similar to SEQ ID NO: 60. In an aspect, a CasX nuclease provided herein comprises an amino acid sequence at least 96% similar to SEQ ID NO: 60. In an aspect, a CasX nuclease provided herein comprises an amino acid sequence at least 97% similar to SEQ ID NO: 60. In an aspect, a CasX nuclease provided herein comprises an amino acid sequence at least 98% similar to SEQ ID NO: 60. In an aspect, a CasX nuclease provided herein comprises an amino acid sequence at least 99% similar to SEQ ID NO: 60. In an aspect, a CasX nuclease provided herein comprises an amino acid sequence 100% similar to SEQ ID NO: 60.

In an aspect, a nucleic acid molecule provided herein encodes a CasX protein comprising an amino acid sequence at least 80% identical to SEQ ID NO: 60. In an aspect, a nucleic acid molecule provided herein encodes a CasX protein comprising an amino acid sequence at least 85% identical to SEQ ID NO: 60. In an aspect, a nucleic acid molecule provided herein encodes a CasX protein comprising an amino acid sequence at least 90% identical to SEQ ID NO: 60. In an aspect, a nucleic acid molecule provided herein encodes a CasX protein comprising an amino acid sequence at least 91% identical to SEQ ID NO: 60. In an aspect, a nucleic acid molecule provided herein encodes a CasX protein comprising an amino acid sequence at least 92% identical to SEQ ID NO: 60. In an aspect, a nucleic acid molecule provided herein encodes a CasX protein comprising an amino acid sequence at least 93% identical to SEQ ID NO: 60. In an aspect, a nucleic acid molecule provided herein encodes a CasX protein comprising an amino acid sequence at least 94% identical to SEQ ID NO: 60. In an aspect, a nucleic acid molecule provided herein encodes a CasX protein comprising an amino acid sequence at least 95% identical to SEQ ID NO: 60. In an aspect, a nucleic acid molecule provided herein encodes a CasX protein comprising an amino acid sequence at least 96% identical to SEQ ID NO: 60. In an aspect, a nucleic acid molecule provided herein encodes a CasX protein comprising an amino acid sequence at least 97% identical to SEQ ID NO: 60. In an aspect, a nucleic acid molecule provided herein encodes a CasX protein comprising an amino acid sequence at least 98% identical to SEQ ID NO: 60. In an aspect, a nucleic acid molecule provided herein encodes a CasX protein comprising an amino acid sequence at least 99% identical to SEQ ID NO: 60. In an aspect, a nucleic acid molecule provided herein encodes a CasX protein comprising an amino acid sequence 100% identical to SEQ ID NO: 60.

In an aspect, a nucleic acid molecule provided herein encodes a CasX protein comprising an amino acid sequence at least 80% similar to SEQ ID NO: 60. In an aspect, a nucleic acid molecule provided herein encodes a CasX protein comprising an amino acid sequence at least 85% similar to SEQ ID NO: 60. In an aspect, a nucleic acid molecule provided herein encodes a CasX protein comprising an amino acid sequence at least 90% similar to SEQ ID NO: 60. In an aspect, a nucleic acid molecule provided herein encodes a CasX protein comprising an amino acid sequence at least 91% similar to SEQ ID NO: 60. In an aspect, a nucleic acid molecule provided herein encodes a CasX protein comprising an amino acid sequence at least 92% similar to SEQ ID NO: 60. In an aspect, a nucleic acid molecule provided herein encodes a CasX protein comprising an amino acid sequence at least 93% similar to SEQ ID NO: 60. In an aspect, a nucleic acid molecule provided herein encodes a CasX protein comprising an amino acid sequence at least 94% similar to SEQ ID NO: 60. In an aspect, a nucleic acid molecule provided herein encodes a CasX protein comprising an amino acid sequence at least 95% similar to SEQ ID NO: 60. In an aspect, a nucleic acid molecule provided herein encodes a CasX protein comprising an amino acid sequence at least 96% similar to SEQ ID NO: 60. In an aspect, a nucleic acid molecule provided herein encodes a CasX protein comprising an amino acid sequence at least 97% similar to SEQ ID NO: 60. In an aspect, a nucleic acid molecule provided herein encodes a CasX protein comprising an amino acid sequence at least 98% similar to SEQ ID NO: 60. In an aspect, a nucleic acid molecule provided herein encodes a CasX protein comprising an amino acid sequence at least 99% similar to SEQ ID NO: 60. In an aspect, a nucleic acid molecule provided herein encodes a CasX protein comprising an amino acid sequence 100% similar to SEQ ID NO: 60.

In an aspect, a CasX nuclease provided herein comprises an amino acid sequence that is at least 80% identical or similar to SEQ ID NO: 1 or 60. In an aspect, a CasX nuclease provided herein comprises an amino acid sequence that is at least 85% identical or similar to SEQ ID NO: 1 or 60. In an aspect, a CasX nuclease provided herein comprises an amino acid sequence that is at least 90% identical or similar to SEQ ID NO: 1 or 60. In an aspect, a CasX nuclease provided herein comprises an amino acid sequence that is at least 91% identical or similar to SEQ ID NO: 1 or 60. In an aspect, a CasX nuclease provided herein comprises an amino acid sequence that is at least 92% identical or similar to SEQ ID NO: 1 or 60. In an aspect, a CasX nuclease provided herein comprises an amino acid sequence that is at least 93% identical or similar to SEQ ID NO: 1 or 60. In an aspect, a CasX nuclease provided herein comprises an amino acid sequence that is at least 94% identical or similar to SEQ ID NO: 1 or 60. In an aspect, a CasX nuclease provided herein comprises an amino acid sequence that is at least 95% identical or similar to SEQ ID NO: 1 or 60. In an aspect, a CasX nuclease provided herein comprises an amino acid sequence that is at least 96% identical or similar to SEQ ID NO: 1 or 60. In an aspect, a CasX nuclease provided herein comprises an amino acid sequence that is at least 97% identical or similar to SEQ ID NO: 1 or 60. In an aspect, a CasX nuclease provided herein comprises an amino acid sequence that is at least 98% identical or similar to SEQ ID NO: 1 or 60. In an aspect, a CasX nuclease provided herein comprises an amino acid sequence that is at least 99% identical or similar to SEQ ID NO: 1 or 60. In an aspect, a CasX nuclease provided herein comprises an amino acid sequence that is 100% identical or similar to SEQ ID NO: 1 or 60.

In an aspect, a nucleic acid molecule provided herein encodes a CasX nuclease comprising an amino acid sequence at least 80% identical or similar to SEQ ID NO: 1 or 60. In an aspect, a nucleic acid molecule provided herein encodes a CasX nuclease comprising an amino acid sequence at least 85% identical or similar to SEQ ID NO: 1 or 60. In an aspect, a nucleic acid molecule provided herein encodes a CasX nuclease comprising an amino acid sequence at least 90% identical or similar to SEQ ID NO: 1 or 60. In an aspect, a nucleic acid molecule provided herein encodes a CasX nuclease comprising an amino acid sequence at least 91% identical or similar to SEQ ID NO: 1 or 60. In an aspect, a nucleic acid molecule provided herein encodes a CasX nuclease comprising an amino acid sequence at least 92% identical or similar to SEQ ID NO: 1 or 60. In an aspect, a nucleic acid molecule provided herein encodes a CasX nuclease comprising an amino acid sequence at least 93% identical or similar to SEQ ID NO: 1 or 60. In an aspect, a nucleic acid molecule provided herein encodes a CasX nuclease comprising an amino acid sequence at least 94% identical or similar to SEQ ID NO: 1 or 60. In an aspect, a nucleic acid molecule provided herein encodes a CasX nuclease comprising an amino acid sequence at least 95% identical or similar to SEQ ID NO: 1 or 60. In an aspect, a nucleic acid molecule provided herein encodes a CasX nuclease comprising an amino acid sequence at least 96% identical or similar to SEQ ID NO: 1 or 60. In an aspect, a nucleic acid molecule provided herein encodes a CasX nuclease comprising an amino acid sequence at least 97% identical or similar to SEQ ID NO: 1 or 60. In an aspect, a nucleic acid molecule provided herein encodes a CasX nuclease comprising an amino acid sequence at least 98% identical or similar to SEQ ID NO: 1 or 60. In an aspect, a nucleic acid molecule provided herein encodes a CasX nuclease comprising an amino acid sequence at least 99% identical or similar to SEQ ID NO: 1 or 60. In an aspect, a nucleic acid molecule provided herein encodes a CasX nuclease comprising an amino acid sequence 100% identical or similar to SEQ ID NO: 1 or 60.

In one aspect, a CasX nuclease provided herein is encoded by a nucleic acid molecule comprising a sequence at least 80% identical to SEQ ID NO: 2. In one aspect, a CasX nuclease provided herein is encoded by a nucleic acid molecule comprising a sequence at least 85% identical to SEQ ID NO: 2. In one aspect, a CasX nuclease provided herein is encoded by a nucleic acid molecule comprising a sequence at least 90% identical to SEQ ID NO: 2. In one aspect, a CasX nuclease provided herein is encoded by a nucleic acid molecule comprising a sequence at least 91% identical to SEQ ID NO: 2. In one aspect, a CasX nuclease provided herein is encoded by a nucleic acid molecule comprising a sequence at least 92% identical to SEQ ID NO: 2. In one aspect, a CasX nuclease provided herein is encoded by a nucleic acid molecule comprising a sequence at least 93% identical to SEQ ID NO: 2. In one aspect, a CasX nuclease provided herein is encoded by a nucleic acid molecule comprising a sequence at least 94% identical to SEQ ID NO: 2. In one aspect, a CasX nuclease provided herein is encoded by a nucleic acid molecule comprising a sequence at least 95% identical to SEQ ID NO: 2. In one aspect, a CasX nuclease provided herein is encoded by a nucleic acid molecule comprising a sequence at least 96% identical to SEQ ID NO: 2. In one aspect, a CasX nuclease provided herein is encoded by a nucleic acid molecule comprising a sequence at least 97% identical to SEQ ID NO: 2. In one aspect, a CasX nuclease provided herein is encoded by a nucleic acid molecule comprising a sequence at least 98% identical to SEQ ID NO: 2. In one aspect, a CasX nuclease provided herein is encoded by a nucleic acid molecule comprising a sequence at least 99% identical to SEQ ID NO: 2. In one aspect, a CasX nuclease provided herein is encoded by a nucleic acid molecule comprising a sequence 100% identical to SEQ ID NO: 2.

In one aspect, a CasX nuclease provided herein is encoded by a nucleic acid molecule comprising a sequence at least 80% identical to SEQ ID NO: 61. In one aspect, a CasX nuclease provided herein is encoded by a nucleic acid molecule comprising a sequence at least 85% identical to SEQ ID NO: 61. In one aspect, a CasX nuclease provided herein is encoded by a nucleic acid molecule comprising a sequence at least 90% identical to SEQ ID NO: 61. In one aspect, a CasX nuclease provided herein is encoded by a nucleic acid molecule comprising a sequence at least 91% identical to SEQ ID NO: 61. In one aspect, a CasX nuclease provided herein is encoded by a nucleic acid molecule comprising a sequence at least 92% identical to SEQ ID NO: 61. In one aspect, a CasX nuclease provided herein is encoded by a nucleic acid molecule comprising a sequence at least 93% identical to SEQ ID NO: 61. In one aspect, a CasX nuclease provided herein is encoded by a nucleic acid molecule comprising a sequence at least 94% identical to SEQ ID NO: 61. In one aspect, a CasX nuclease provided herein is encoded by a nucleic acid molecule comprising a sequence at least 95% identical to SEQ ID NO: 61. In one aspect, a CasX nuclease provided herein is encoded by a nucleic acid molecule comprising a sequence at least 96% identical to SEQ ID NO: 61. In one aspect, a CasX nuclease provided herein is encoded by a nucleic acid molecule comprising a sequence at least 97% identical to SEQ ID NO: 61. In one aspect, a CasX nuclease provided herein is encoded by a nucleic acid molecule comprising a sequence at least 98% identical to SEQ ID NO: 61. In one aspect, a CasX nuclease provided herein is encoded by a nucleic acid molecule comprising a sequence at least 99% identical to SEQ ID NO: 61. In one aspect, a CasX nuclease provided herein is encoded by a nucleic acid molecule comprising a sequence 100% identical to SEQ ID NO: 61.

In an aspect, a CasX nuclease provided herein is encoded by a nucleic acid sequence at least 80% identical to SEQ ID NO: 2 or 61. In an aspect, a CasX nuclease provided herein is encoded by a nucleic acid sequence at least 85% identical to SEQ ID NO: 2 or 61. In an aspect, a CasX nuclease provided herein is encoded by a nucleic acid sequence at least 90% identical to SEQ ID NO: 2 or 61. In an aspect, a CasX nuclease provided herein is encoded by a nucleic acid sequence at least 91% identical to SEQ ID NO: 2 or 61. In an aspect, a CasX nuclease provided herein is encoded by a nucleic acid sequence at least 92% identical to SEQ ID NO: 2 or 61. In an aspect, a CasX nuclease provided herein is encoded by a nucleic acid sequence at least 93% identical to SEQ ID NO: 2 or 61. In an aspect, a CasX nuclease provided herein is encoded by a nucleic acid sequence at least 94% identical to SEQ ID NO: 2 or 61. In an aspect, a CasX nuclease provided herein is encoded by a nucleic acid sequence at least 95% identical to SEQ ID NO: 2 or 61. In an aspect, a CasX nuclease provided herein is encoded by a nucleic acid sequence at least 96% identical to SEQ ID NO: 2 or 61. In an aspect, a CasX nuclease provided herein is encoded by a nucleic acid sequence at least 97% identical to SEQ ID NO: 2 or 61. In an aspect, a CasX nuclease provided herein is encoded by a nucleic acid sequence at least 98% identical to SEQ ID NO: 2 or 61. In an aspect, a CasX nuclease provided herein is encoded by a nucleic acid sequence at least 99% identical to SEQ ID NO: 2 or 61. In an aspect, a CasX nuclease provided herein is encoded by a nucleic acid sequence 100% identical to SEQ ID NO: 2 or 61.

In one aspect, a CasX nuclease provided herein is encoded by a nucleic acid molecule comprising a sequence at least 80% identical to SEQ ID NO: 3. In one aspect, a CasX nuclease provided herein is encoded by a nucleic acid molecule comprising a sequence at least 85% identical to SEQ ID NO: 3. In one aspect, a CasX nuclease provided herein is encoded by a nucleic acid molecule comprising a sequence at least 90% identical to SEQ ID NO: 3. In one aspect, a CasX nuclease provided herein is encoded by a nucleic acid molecule comprising a sequence at least 91% identical to SEQ ID NO: 3. In one aspect, a CasX nuclease provided herein is encoded by a nucleic acid molecule comprising a sequence at least 92% identical to SEQ ID NO: 3. In one aspect, a CasX nuclease provided herein is encoded by a nucleic acid molecule comprising a sequence at least 93% identical to SEQ ID NO: 3. In one aspect, a CasX nuclease provided herein is encoded by a nucleic acid molecule comprising a sequence at least 94% identical to SEQ ID NO: 3. In one aspect, a CasX nuclease provided herein is encoded by a nucleic acid molecule comprising a sequence at least 95% identical to SEQ ID NO: 3. In one aspect, a CasX nuclease provided herein is encoded by a nucleic acid molecule comprising a sequence at least 96% identical to SEQ ID NO: 3. In one aspect, a CasX nuclease provided herein is encoded by a nucleic acid molecule comprising a sequence at least 97% identical to SEQ ID NO: 3. In one aspect, a CasX nuclease provided herein is encoded by a nucleic acid molecule comprising a sequence at least 98% identical to SEQ ID NO: 3. In one aspect, a CasX nuclease provided herein is encoded by a nucleic acid molecule comprising a sequence at least 99% identical to SEQ ID NO: 3. In one aspect, a CasX nuclease provided herein is encoded by a nucleic acid molecule comprising a sequence 100% identical to SEQ ID NO: 3.

In one aspect, a CasX nuclease provided herein is encoded by a nucleic acid molecule comprising a sequence at least 80% identical to SEQ ID NO: 39. In one aspect, a CasX nuclease provided herein is encoded by a nucleic acid molecule comprising a sequence at least 85% identical to SEQ ID NO: 39. In one aspect, a CasX nuclease provided herein is encoded by a nucleic acid molecule comprising a sequence at least 90% identical to SEQ ID NO: 39. In one aspect, a CasX nuclease provided herein is encoded by a nucleic acid molecule comprising a sequence at least 91% identical to SEQ ID NO: 39. In one aspect, a CasX nuclease provided herein is encoded by a nucleic acid molecule comprising a sequence at least 92% identical to SEQ ID NO: 39. In one aspect, a CasX nuclease provided herein is encoded by a nucleic acid molecule comprising a sequence at least 93% identical to SEQ ID NO: 39. In one aspect, a CasX nuclease provided herein is encoded by a nucleic acid molecule comprising a sequence at least 94% identical to SEQ ID NO: 39. In one aspect, a CasX nuclease provided herein is encoded by a nucleic acid molecule comprising a sequence at least 95% identical to SEQ ID NO: 39. In one aspect, a CasX nuclease provided herein is encoded by a nucleic acid molecule comprising a sequence at least 96% identical to SEQ ID NO: 39. In one aspect, a CasX nuclease provided herein is encoded by a nucleic acid molecule comprising a sequence at least 97% identical to SEQ ID NO: 39. In one aspect, a CasX nuclease provided herein is encoded by a nucleic acid molecule comprising a sequence at least 98% identical to SEQ ID NO: 39. In one aspect, a CasX nuclease provided herein is encoded by a nucleic acid molecule comprising a sequence at least 99% identical to SEQ ID NO: 39. In one aspect, a CasX nuclease provided herein is encoded by a nucleic acid molecule comprising a sequence 100% identical to SEQ ID NO: 39.

In one aspect, a CasX nuclease provided herein is encoded by a nucleic acid molecule comprising a sequence at least 80% identical to SEQ ID NO: 62. In one aspect, a CasX nuclease provided herein is encoded by a nucleic acid molecule comprising a sequence at least 85% identical to SEQ ID NO: 62. In one aspect, a CasX nuclease provided herein is encoded by a nucleic acid molecule comprising a sequence at least 90% identical to SEQ ID NO: 62. In one aspect, a CasX nuclease provided herein is encoded by a nucleic acid molecule comprising a sequence at least 91% identical to SEQ ID NO: 62. In one aspect, a CasX nuclease provided herein is encoded by a nucleic acid molecule comprising a sequence at least 92% identical to SEQ ID NO: 62. In one aspect, a CasX nuclease provided herein is encoded by a nucleic acid molecule comprising a sequence at least 93% identical to SEQ ID NO: 62. In one aspect, a CasX nuclease provided herein is encoded by a nucleic acid molecule comprising a sequence at least 94% identical to SEQ ID NO: 62. In one aspect, a CasX nuclease provided herein is encoded by a nucleic acid molecule comprising a sequence at least 95% identical to SEQ ID NO: 62. In one aspect, a CasX nuclease provided herein is encoded by a nucleic acid molecule comprising a sequence at least 96% identical to SEQ ID NO: 62. In one aspect, a CasX nuclease provided herein is encoded by a nucleic acid molecule comprising a sequence at least 97% identical to SEQ ID NO: 62. In one aspect, a CasX nuclease provided herein is encoded by a nucleic acid molecule comprising a sequence at least 98% identical to SEQ ID NO: 62. In one aspect, a CasX nuclease provided herein is encoded by a nucleic acid molecule comprising a sequence at least 99% identical to SEQ ID NO: 62. In one aspect, a CasX nuclease provided herein is encoded by a nucleic acid molecule comprising a sequence 100% identical to SEQ ID NO: 62.

In an aspect, a CasX nuclease provided herein is encoded by a nucleic acid sequence at least 80% identical to a sequence selected from the group consisting of SEQ ID NOs: 3, 39, 62, 79 and 80. In an aspect, a CasX nuclease provided herein is encoded by a nucleic acid sequence at least 85% identical to a sequence selected from the group consisting of SEQ ID NOs: 3, 39, 62, 79 and 80. In an aspect, a CasX nuclease provided herein is encoded by a nucleic acid sequence at least 90% identical to a sequence selected from the group consisting of SEQ ID NOs: 3, 39, 62, 79 and 80. In an aspect, a CasX nuclease provided herein is encoded by a nucleic acid sequence at least 91% identical to a sequence selected from the group consisting of SEQ ID NOs: 3, 39, 62, 79 and 80. In an aspect, a CasX nuclease provided herein is encoded by a nucleic acid sequence at least 92% identical to a sequence selected from the group consisting of SEQ ID NOs: 3, 39, 62, 79 and 80. In an aspect, a CasX nuclease provided herein is encoded by a nucleic acid sequence at least 93% identical to a sequence selected from the group consisting of SEQ ID NOs: 3, 39, 62, 79 and 80. In an aspect, a CasX nuclease provided herein is encoded by a nucleic acid sequence at least 94% identical to a sequence selected from the group consisting of SEQ ID NOs: 3, 39, 62, 79 and 80. In an aspect, a CasX nuclease provided herein is encoded by a nucleic acid sequence at least 95% identical to a sequence selected from the group consisting of SEQ ID NOs: 3, 39, 62, 79 and 80. In an aspect, a CasX nuclease provided herein is encoded by a nucleic acid sequence at least 96% identical to a sequence selected from the group consisting of SEQ ID NOs: 3, 39, 62, 79 and 80. In an aspect, a CasX nuclease provided herein is encoded by a nucleic acid sequence at least 97% identical to a sequence selected from the group consisting of SEQ ID NOs: 3, 39, 62, 79 and 80. In an aspect, a CasX nuclease provided herein is encoded by a nucleic acid sequence at least 98% identical to a sequence selected from the group consisting of SEQ ID NOs: 3, 39, 62, 79 and 80. In an aspect, a CasX nuclease provided herein is encoded by a nucleic acid sequence at least 99% identical to a sequence selected from the group consisting of SEQ ID NOs: 3, 39, 62, 79 and 80. In an aspect, a CasX nuclease provided herein is encoded by a nucleic acid sequence 100% identical to a sequence selected from the group consisting of SEQ ID NOs: 3, 39, 62, 79 and 80.

In one aspect, a CasX nuclease provided herein is encoded by a nucleic acid molecule comprising a sequence at least 80% identical to SEQ ID NO: 9. In one aspect, a CasX nuclease provided herein is encoded by a nucleic acid molecule comprising a sequence at least 85% identical to SEQ ID NO: 9. In one aspect, a CasX nuclease provided herein is encoded by a nucleic acid molecule comprising a sequence at least 90% identical to SEQ ID NO: 9. In one aspect, a CasX nuclease provided herein is encoded by a nucleic acid molecule comprising a sequence at least 91% identical to SEQ ID NO: 9. In one aspect, a CasX nuclease provided herein is encoded by a nucleic acid molecule comprising a sequence at least 92% identical to SEQ ID NO: 9. In one aspect, a CasX nuclease provided herein is encoded by a nucleic acid molecule comprising a sequence at least 93% identical to SEQ ID NO: 9. In one aspect, a CasX nuclease provided herein is encoded by a nucleic acid molecule comprising a sequence at least 94% identical to SEQ ID NO: 9. In one aspect, a CasX nuclease provided herein is encoded by a nucleic acid molecule comprising a sequence at least 95% identical to SEQ ID NO: 9. In one aspect, a CasX nuclease provided herein is encoded by a nucleic acid molecule comprising a sequence at least 96% identical to SEQ ID NO: 9. In one aspect, a CasX nuclease provided herein is encoded by a nucleic acid molecule comprising a sequence at least 97% identical to SEQ ID NO: 9. In one aspect, a CasX nuclease provided herein is encoded by a nucleic acid molecule comprising a sequence at least 98% identical to SEQ ID NO: 9. In one aspect, a CasX nuclease provided herein is encoded by a nucleic acid molecule comprising a sequence at least 99% identical to SEQ ID NO: 9. In one aspect, a CasX nuclease provided herein is encoded by a nucleic acid molecule comprising a sequence 100% identical to SEQ ID NO: 9.

In one aspect, a CasX nuclease provided herein is encoded by a nucleic acid molecule comprising a sequence at least 80% identical to SEQ ID NO: 44. In one aspect, a CasX nuclease provided herein is encoded by a nucleic acid molecule comprising a sequence at least 85% identical to SEQ ID NO: 44. In one aspect, a CasX nuclease provided herein is encoded by a nucleic acid molecule comprising a sequence at least 90% identical to SEQ ID NO: 44. In one aspect, a CasX nuclease provided herein is encoded by a nucleic acid molecule comprising a sequence at least 91% identical to SEQ ID NO: 44. In one aspect, a CasX nuclease provided herein is encoded by a nucleic acid molecule comprising a sequence at least 92% identical to SEQ ID NO: 44. In one aspect, a CasX nuclease provided herein is encoded by a nucleic acid molecule comprising a sequence at least 93% identical to SEQ ID NO: 44. In one aspect, a CasX nuclease provided herein is encoded by a nucleic acid molecule comprising a sequence at least 94% identical to SEQ ID NO: 44. In one aspect, a CasX nuclease provided herein is encoded by a nucleic acid molecule comprising a sequence at least 95% identical to SEQ ID NO: 44. In one aspect, a CasX nuclease provided herein is encoded by a nucleic acid molecule comprising a sequence at least 96% identical to SEQ ID NO: 44. In one aspect, a CasX nuclease provided herein is encoded by a nucleic acid molecule comprising a sequence at least 97% identical to SEQ ID NO: 44. In one aspect, a CasX nuclease provided herein is encoded by a nucleic acid molecule comprising a sequence at least 98% identical to SEQ ID NO: 44. In one aspect, a CasX nuclease provided herein is encoded by a nucleic acid molecule comprising a sequence at least 99% identical to SEQ ID NO: 44. In one aspect, a CasX nuclease provided herein is encoded by a nucleic acid molecule comprising a sequence 100% identical to SEQ ID NO: 44.

In one aspect, a CasX nuclease provided herein is encoded by a nucleic acid molecule comprising a sequence at least 80% identical to SEQ ID NO: 64. In one aspect, a CasX nuclease provided herein is encoded by a nucleic acid molecule comprising a sequence at least 85% identical to SEQ ID NO: 64. In one aspect, a CasX nuclease provided herein is encoded by a nucleic acid molecule comprising a sequence at least 90% identical to SEQ ID NO: 64. In one aspect, a CasX nuclease provided herein is encoded by a nucleic acid molecule comprising a sequence at least 91% identical to SEQ ID NO: 64. In one aspect, a CasX nuclease provided herein is encoded by a nucleic acid molecule comprising a sequence at least 92% identical to SEQ ID NO: 64. In one aspect, a CasX nuclease provided herein is encoded by a nucleic acid molecule comprising a sequence at least 93% identical to SEQ ID NO: 64. In one aspect, a CasX nuclease provided herein is encoded by a nucleic acid molecule comprising a sequence at least 94% identical to SEQ ID NO: 64. In one aspect, a CasX nuclease provided herein is encoded by a nucleic acid molecule comprising a sequence at least 95% identical to SEQ ID NO: 64. In one aspect, a CasX nuclease provided herein is encoded by a nucleic acid molecule comprising a sequence at least 96% identical to SEQ ID NO: 64. In one aspect, a CasX nuclease provided herein is encoded by a nucleic acid molecule comprising a sequence at least 97% identical to SEQ ID NO: 64. In one aspect, a CasX nuclease provided herein is encoded by a nucleic acid molecule comprising a sequence at least 98% identical to SEQ ID NO: 64. In one aspect, a CasX nuclease provided herein is encoded by a nucleic acid molecule comprising a sequence at least 99% identical to SEQ ID NO: 64. In one aspect, a CasX nuclease provided herein is encoded by a nucleic acid molecule comprising a sequence 100% identical to SEQ ID NO: 64.

In an aspect, a CasX nuclease provided herein is encoded by a nucleic acid sequence at least 80% identical to a sequence selected from the group consisting of SEQ ID NOs: 9, 44, and 64. In an aspect, a CasX nuclease provided herein is encoded by a nucleic acid sequence at least 85% identical to a sequence selected from the group consisting of SEQ ID NOs: 9, 44, and 64. In an aspect, a CasX nuclease provided herein is encoded by a nucleic acid sequence at least 90% identical to a sequence selected from the group consisting of SEQ ID NOs: 9, 44, and 64. In an aspect, a CasX nuclease provided herein is encoded by a nucleic acid sequence at least 91% identical to a sequence selected from the group consisting of SEQ ID NOs: 9, 44, and 64. In an aspect, a CasX nuclease provided herein is encoded by a nucleic acid sequence at least 92% identical to a sequence selected from the group consisting of SEQ ID NOs: 9, 44, and 64. In an aspect, a CasX nuclease provided herein is encoded by a nucleic acid sequence at least 93% identical to a sequence selected from the group consisting of SEQ ID NOs: 9, 44, and 64. In an aspect, a CasX nuclease provided herein is encoded by a nucleic acid sequence at least 94% identical to a sequence selected from the group consisting of SEQ ID NOs: 9, 44, and 64. In an aspect, a CasX nuclease provided herein is encoded by a nucleic acid sequence at least 95% identical to a sequence selected from the group consisting of SEQ ID NOs: 9, 44, and 64. In an aspect, a CasX nuclease provided herein is encoded by a nucleic acid sequence at least 96% identical to a sequence selected from the group consisting of SEQ ID NOs: 9, 44, and 64. In an aspect, a CasX nuclease provided herein is encoded by a nucleic acid sequence at least 97% identical to a sequence selected from the group consisting of SEQ ID NOs: 9, 44, and 64. In an aspect, a CasX nuclease provided herein is encoded by a nucleic acid sequence at least 98% identical to a sequence selected from the group consisting of SEQ ID NOs: 9, 44, and 64. In an aspect, a CasX nuclease provided herein is encoded by a nucleic acid sequence at least 99% identical to a sequence selected from the group consisting of SEQ ID NOs: 9, 44, and 64. In an aspect, a CasX nuclease provided herein is encoded by a nucleic acid sequence 100% identical to a sequence selected from the group consisting of SEQ ID NOs: 9, 44, and 64.

In one aspect, a CasX nuclease provided herein is encoded by a nucleic acid molecule comprising a sequence at least 80% identical to SEQ ID NO: 80. In one aspect, a CasX nuclease provided herein is encoded by a nucleic acid molecule comprising a sequence at least 85% identical to SEQ ID NO: 80. In one aspect, a CasX nuclease provided herein is encoded by a nucleic acid molecule comprising a sequence at least 90% identical to SEQ ID NO: 80. In one aspect, a CasX nuclease provided herein is encoded by a nucleic acid molecule comprising a sequence at least 91% identical to SEQ ID NO: 80. In one aspect, a CasX nuclease provided herein is encoded by a nucleic acid molecule comprising a sequence at least 92% identical to SEQ ID NO: 80. In one aspect, a CasX nuclease provided herein is encoded by a nucleic acid molecule comprising a sequence at least 93% identical to SEQ ID NO: 80. In one aspect, a CasX nuclease provided herein is encoded by a nucleic acid molecule comprising a sequence at least 94% identical to SEQ ID NO: 80. In one aspect, a CasX nuclease provided herein is encoded by a nucleic acid molecule comprising a sequence at least 95% identical to SEQ ID NO: 80. In one aspect, a CasX nuclease provided herein is encoded by a nucleic acid molecule comprising a sequence at least 96% identical to SEQ ID NO: 80. In one aspect, a CasX nuclease provided herein is encoded by a nucleic acid molecule comprising a sequence at least 97% identical to SEQ ID NO: 80. In one aspect, a CasX nuclease provided herein is encoded by a nucleic acid molecule comprising a sequence at least 98% identical to SEQ ID NO: 80. In one aspect, a CasX nuclease provided herein is encoded by a nucleic acid molecule comprising a sequence at least 99% identical to SEQ ID NO: 80. In one aspect, a CasX nuclease provided herein is encoded by a nucleic acid molecule comprising a sequence 100% identical to SEQ ID NO: 80.

In one aspect, a CasX nuclease provided herein is encoded by a nucleic acid molecule comprising a sequence at least 80% identical to SEQ ID NO: 79. In one aspect, a CasX nuclease provided herein is encoded by a nucleic acid molecule comprising a sequence at least 85% identical to SEQ ID NO: 79. In one aspect, a CasX nuclease provided herein is encoded by a nucleic acid molecule comprising a sequence at least 90% identical to SEQ ID NO: 79. In one aspect, a CasX nuclease provided herein is encoded by a nucleic acid molecule comprising a sequence at least 91% identical to SEQ ID NO: 79. In one aspect, a CasX nuclease provided herein is encoded by a nucleic acid molecule comprising a sequence at least 92% identical to SEQ ID NO: 79. In one aspect, a CasX nuclease provided herein is encoded by a nucleic acid molecule comprising a sequence at least 93% identical to SEQ ID NO: 79. In one aspect, a CasX nuclease provided herein is encoded by a nucleic acid molecule comprising a sequence at least 94% identical to SEQ ID NO: 79. In one aspect, a CasX nuclease provided herein is encoded by a nucleic acid molecule comprising a sequence at least 95% identical to SEQ ID NO: 79. In one aspect, a CasX nuclease provided herein is encoded by a nucleic acid molecule comprising a sequence at least 96% identical to SEQ ID NO: 79. In one aspect, a CasX nuclease provided herein is encoded by a nucleic acid molecule comprising a sequence at least 97% identical to SEQ ID NO: 79. In one aspect, a CasX nuclease provided herein is encoded by a nucleic acid molecule comprising a sequence at least 98% identical to SEQ ID NO: 79. In one aspect, a CasX nuclease provided herein is encoded by a nucleic acid molecule comprising a sequence at least 99% identical to SEQ ID NO: 79. In one aspect, a CasX nuclease provided herein is encoded by a nucleic acid molecule comprising a sequence 100% identical to SEQ ID NO: 79.

In an aspect, a CasX nuclease provided herein is a CasX nuclease from a bacteria in the phylum Deltaproteobacteria. In an aspect, a CasX nuclease provided herein is a CasX nuclease from a bacteria in the phylum Planctomycetes.

In an aspect, one or more intron sequences can be added to a nucleic acid encoding a CasX nuclease. In an aspect, a nucleic acid sequence encoding a CasX nuclease comprises an intron. In an aspect, an intron added to a nucleic acid sequence encoding a CasX nuclease is heterologous to the nucleic sequence encoding the CasX nuclease. As used herein, an "intron" refers to a nucleotide sequence that is removed by RNA splicing as a messenger RNA (mRNA) matures from a mRNA precursor.

The term "operably linked" refers to a functional linkage between a promoter or other regulatory element and an associated transcribable DNA sequence or coding sequence of a gene (or transgene), such that the promoter, etc., operates to initiate, assist, affect, cause, and/or promote the transcription and expression of the associated transcribable DNA sequence or coding sequence, at least in certain tissue(s), developmental stage(s) and/or condition(s). In addition to promoters, regulatory elements include, without being limiting, an enhancer, a leader, a transcription start site (TSS), a linker, 5' and 3' untranslated regions (UTRs), an intron, a polyadenylation signal, and a termination region or sequence, etc., that are suitable, necessary or preferred for regulating or allowing expression of the gene or transcribable DNA sequence in a cell. Such additional regulatory element(s) can be optional and used to enhance or optimize expression of the gene or transcribable DNA sequence.

As commonly understood in the art, the term "promoter" refers to a DNA sequence that contains an RNA polymerase binding site, transcription start site, and/or TATA box and assists or promotes the transcription and expression of an associated transcribable polynucleotide sequence and/or gene (or transgene). A promoter can be synthetically produced, varied or derived from a known or naturally occurring promoter sequence or other promoter sequence. A promoter can also include a chimeric promoter comprising a combination of two or more heterologous sequences. A promoter of the present application can thus include variants of promoter sequences that are similar in composition, but not identical to, other promoter sequence(s) known or provided herein. A promoter can be classified according to a variety of criteria relating to the pattern of expression of an associated coding or transcribable sequence or gene (including a transgene) operably linked to the promoter, such as constitutive, developmental, tissue-specific, inducible, etc. Promoters that drive expression in all or most tissues of the plant are referred to as "constitutive" promoters. Promoters that drive expression during certain periods or stages of development are referred to as "developmental" promoters. Promoters that drive enhanced expression in certain tissues of an organism relative to other tissues of the organism are referred to as "tissue-preferred" promoters. Thus, a "tissue-preferred" promoter causes relatively higher or preferential expression in a specific tissue(s) of a plant, but with lower levels of expression in other tissue(s) of the plant. Promoters that express within a specific tissue(s) of an organism, with little or no expression in other tissues, are referred to as "tissue-specific" promoters. An "inducible" promoter is a promoter that initiates transcription in response to an environmental stimulus such as heat, cold, drought, light, or other stimuli, such as wounding or chemical application. A promoter can also be classified in terms of its origin, such as being heterologous, homologous, chimeric, synthetic, etc.

As used herein, the term "heterologous" in reference to a promoter is a promoter sequence having a different origin relative to its associated transcribable DNA sequence, coding sequence or gene (or transgene), and/or not naturally occurring in the plant species to be transformed. The term "heterologous" can refer more broadly to a combination of two or more DNA molecules or sequences, such as a promoter and an associated transcribable DNA sequence, coding sequence or gene, when such a combination is man-made and not normally found in nature.

In an aspect, a promoter provided herein is a constitutive promoter. In another aspect, a promoter provided herein is a tissue-specific promoter. In a further aspect, a promoter provided herein is a tissue-preferred promoter. In still another aspect, a promoter provided herein is an inducible promoter. In an aspect, a promoter provided herein is selected from the group consisting of a constitutive promoter, a tissue-specific promoter, a tissue-preferred promoter, and an inducible promoter.

RNA polymerase III (Pol III) promoters can be used to drive the expression of non-protein coding RNA molecules. In an aspect, a promoter provided herein is a Pol III promoter. In another aspect, a Pol III promoter provided herein is operably linked to a nucleic acid molecule encoding a non-protein coding RNA. In yet another aspect, a Pol III promoter provided herein is operably linked to a nucleic acid molecule encoding a guide RNA (gRNA). In still another aspect, a Pol III promoter provided herein is operably linked to a nucleic acid molecule encoding a single-guide RNA (sgRNA). In a further aspect, a Pol III promoter provided herein is operably linked to a nucleic acid molecule encoding a CRISPR RNA (crRNA). In another aspect, a Pol III promoter provided herein is operably linked to a nucleic acid molecule encoding a tracer RNA (tracrRNA).

Non-limiting examples of Pol III promoters include a U6 promoter, an H1 promoter, a 5S promoter, an Adenovirus 2 (Ad2) VAI promoter, a tRNA promoter, and a 7SK promoter. See, for example, Schramm and Hernandez, 2002, *Genes & Development*, 16:2593-2620, which is incorporated by reference herein in its entirety. In an aspect, a Pol III promoter provided herein is selected from the group consisting of a U6 promoter, an H1 promoter, a 5S promoter, an Adenovirus 2 (Ad2) VAI promoter, a tRNA promoter, and a 7SK promoter. In another aspect, a guide RNA provided herein is operably linked to a promoter selected from the group consisting of a U6 promoter, an H1 promoter, a 5S promoter, an Adenovirus 2 (Ad2) VAI promoter, a tRNA promoter, and a 7SK promoter. In another aspect, a single-guide RNA provided herein is operably linked to a promoter selected from the group consisting of a U6 promoter, an H1 promoter, a 5S promoter, an Adenovirus 2 (Ad2) VAI promoter, a tRNA promoter, and a 7SK promoter. In another aspect, a CRISPR RNA provided herein is operably linked to a promoter selected from the group consisting of a U6 promoter, an H1 promoter, a 5S promoter, an Adenovirus 2 (Ad2) VAI promoter, a tRNA promoter, and a 7SK promoter. In another aspect, a tracer RNA provided herein is operably linked to a promoter selected from the group consisting of a U6 promoter, an H1 promoter, a 5S promoter, an Adenovirus 2 (Ad2) VAI promoter, a tRNA promoter, and a 7SK promoter.

In an aspect, a promoter provided herein is a Dahlia Mosaic Virus (DaMV) promoter. In another aspect, a promoter provided herein is a U6 promoter. In another aspect, a promoter provided herein is an actin promoter.

Examples describing a promoter that can be used herein include without limitation U.S. Pat. No. 6,437,217 (maize RS81 promoter), U.S. Pat. No. 5,641,876 (rice actin promoter), U.S. Pat. No. 6,426,446 (maize RS324 promoter), U.S. Pat. No. 6,429,362 (maize PR-1 promoter), U.S. Pat. No. 6,232,526 (maize A3 promoter), U.S. Pat. No. 6,177,611 (constitutive maize promoters), U.S. Pat. Nos. 5,322,938, 5,352,605, 5,359,142 and 5,530,196 (35S promoter), U.S. Pat. No. 6,433,252 (maize L3 oleosin promoter), U.S. Pat. No. 6,429,357 (rice actin 2 promoter as well as a rice actin 2 intron), U.S. Pat. No. 5,837,848 (root specific promoter), U.S. Pat. No. 6,294,714 (light inducible promoters), U.S. Pat. No. 6,140,078 (salt inducible promoters), U.S. Pat. No. 6,252,138 (pathogen inducible promoters), U.S. Pat. No. 6,175,060 (phosphorus deficiency inducible promoters), U.S. Pat. No. 6,635,806 (gamma-coixin promoter), and U.S. patent application Ser. No. 09/757,089 (maize chloroplast aldolase promoter). Additional promoters that can find use are a nopaline synthase (NOS) promoter (Ebert et al., 1987), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., *Plant Molecular Biology* (1987) 9:315-324), the CaMV 35S promoter (Odell et al., *Nature* (1985) 313: 810-812), the figwort mosaic virus 35S-promoter (U.S. Pat. Nos. 6,051,753; 5,378,619), the sucrose synthase promoter (Yang and Russell, Proceedings of the National Academy of Sciences, USA (1990) 87: 4144-4148), the R gene complex promoter (Chandler et al., *Plant Cell* (1989) 1: 1175-1183), and the chlorophyll a/b binding protein gene promoter, PC1SV (U.S. Pat. No. 5,850, 019), and AGRtu.nos (GenBank Accession V00087; Depicker et al., *Journal of Molecular and Applied Genetics* (1982) 1: 561-573; Bevan et al., 1983) promoters.

Promoter hybrids can also be used and constructed to enhance transcriptional activity (see U.S. Pat. No. 5,106, 739), or to combine desired transcriptional activity, inducibility and tissue specificity or developmental specificity. Promoters that function in plants include but are not limited to promoters that are inducible, viral, synthetic, constitutive, temporally regulated, spatially regulated, and spatio-temporally regulated. Other promoters that are tissue-enhanced, tissue-specific, or developmentally regulated are also known in the art and envisioned to have utility in the practice of this disclosure.

It is appreciated in the art that a fragment of a promoter sequence can function to drive transcription of an operably linked nucleic acid molecule. For example, without being limiting, if a 1000 bp promoter is truncated to 500 bp, and the 500 bp fragment is capable of driving transcription, the 500 bp fragment is referred to as a "functional fragment."

In one aspect, a promoter provided herein comprises at least 80% identity to SEQ ID NO: 7 or a functional fragment thereof. In one aspect, a promoter provided herein comprises at least 85% identity to SEQ ID NO: 7 or a functional fragment thereof. In one aspect, a promoter provided herein comprises at least 85% identity to SEQ ID NO: 7 or a functional fragment thereof. In one aspect, a promoter provided herein comprises at least 90% identity to SEQ ID NO: 7 or a functional fragment thereof. In one aspect, a promoter provided herein comprises at least 95% identity to SEQ ID NO: 7 or a functional fragment thereof. In one aspect, a promoter provided herein comprises at least 96% identity to SEQ ID NO: 7 or a functional fragment thereof. In one aspect, a promoter provided herein comprises at least 97% identity to SEQ ID NO: 7 or a functional fragment thereof. In one aspect, a promoter provided herein comprises at least 98% identity to SEQ ID NO: 7 or a functional fragment thereof. In one aspect, a promoter provided herein comprises at least 99% identity to SEQ ID NO: 7 or a functional fragment thereof. In one aspect, a promoter provided herein comprises 100% identity to SEQ ID NO: 7 or a functional fragment thereof.

In one aspect, a promoter provided herein comprises at least 80% identity to SEQ ID NO: 17 or a functional fragment thereof. In one aspect, a promoter provided herein comprises at least 85% identity to SEQ ID NO: 17 or a functional fragment thereof. In one aspect, a promoter provided herein comprises at least 85% identity to SEQ ID NO: 17 or a functional fragment thereof. In one aspect, a promoter provided herein comprises at least 90% identity to SEQ ID NO: 17 or a functional fragment thereof. In one aspect, a promoter provided herein comprises at least 95% identity to SEQ ID NO: 17 or a functional fragment thereof. In one aspect, a promoter provided herein comprises at least 96% identity to SEQ ID NO: 17 or a functional fragment thereof. In one aspect, a promoter provided herein comprises at least 97% identity to SEQ ID NO: 17 or a functional fragment thereof. In one aspect, a promoter provided herein comprises at least 98% identity to SEQ ID NO: 17 or a functional fragment thereof. In one aspect, a promoter provided herein comprises at least 99% identity to SEQ ID NO: 17 or a functional fragment thereof. In one aspect, a promoter provided herein comprises 100% identity to SEQ ID NO: 17 or a functional fragment thereof.

As used herein, a "nuclear localization signal" refers to an amino acid sequence that "tags" a protein for import into the nucleus of a cell. In an aspect, a nucleic acid molecule provided herein encodes a nuclear localization signal. In another aspect, a nucleic acid molecule provided herein encodes two or more nuclear localization signals. In an aspect, a CasX nuclease provided herein comprises a nuclear localization signal. In an aspect, a nuclear localization signal is positioned on the N-terminal end of a CasX nuclease. In a further aspect, a nuclear localization signal is positioned on the C-terminal end of a CasX nuclease. In yet another aspect, a nuclear localization signal is positioned on both the N-terminal end and the C-terminal end of a CasX nuclease. In one aspect, a nuclear localization signal provided herein is encoded by SEQ ID NO: 10.

As used herein, a "terminator sequence" refers to any nucleic acid sequence that marks the end of a gene during transcription. In an aspect, a nucleic acid molecule provided herein comprises a terminator sequence. In an aspect, a terminator sequence provided herein is a terminator sequence from a hypothetical protein from *Medicago truncatula*. In another aspect, a terminator provided herein comprises SEQ ID NO: 4.

In addition, the term "recombinant" in reference to a polynucleotide (DNA or RNA) molecule, protein, construct, vector, etc., refers to a polynucleotide or protein molecule or sequence that is man-made and not normally found in nature, and/or is present in a context in which it is not normally found in nature, including a polynucleotide (DNA or RNA) molecule, protein, construct, etc., comprising a combination of polynucleotide or protein sequences that would not naturally occur contiguously or in close proximity together without human intervention, and/or a polynucleotide molecule, protein, construct, etc., comprising at least two polynucleotide or protein sequences that are heterologous with respect to each other. A recombinant polynucleotide or protein molecule, construct, etc., can comprise polynucleotide or protein sequence(s) that is/are (i) separated from other polynucleotide or protein sequence(s) that exist in proximity to each other in nature, and/or (ii) adjacent to (or contiguous with) other polynucleotide or protein sequence(s) that are not naturally in proximity with each other. Such a recombinant polynucleotide molecule, protein, construct, etc., can also refer to a polynucleotide or protein molecule or sequence that has been genetically engineered and/or constructed outside of a cell. For example, a recombinant DNA molecule can comprise any suitable plasmid, vector, etc., and can include a linear or circular DNA molecule. Such plasmids, vectors, etc., can contain various maintenance elements including a prokaryotic origin of replication and selectable marker, as well as one or more transgenes or expression cassettes perhaps in addition to a plant selectable marker gene, etc.

In an aspect, a nucleic acid molecule provided herein comprises a selectable marker gene. A selectable marker can be used to assist in the selection of transformed cells or tissue due to the presence of a selection agent, such as an antibiotic or herbicide, where the selectable marker gene provides tolerance or resistance to the selection agent. Thus, the selection agent can bias or favor the survival, development, growth, proliferation, etc., of transformed cells expressing the selectable marker gene. Commonly used selectable marker genes include, without being limiting, those conferring tolerance or resistance to antibiotics, such as kanamycin and paromomycin (nptII), hygromycin B (aph IV), streptomycin or spectinomycin (aadA) and gentamycin (aac3 and aacC4), or those conferring tolerance or resistance to herbicides such as glufosinate (bar orpat), dicamba (DMO) and glyphosate (aroA or Cp4-EPSPS). Selectable marker genes, which provide an ability to visually screen for transformants, can also be used. Non-limiting examples include luciferase or green fluorescent protein (GFP), or a gene expressing a beta glucuronidase or uidA gene (GUS) for which various chromogenic substrates are known. In one aspect, a nucleic acid molecule provided herein comprises a selectable marker gene selected from the group consisting of nptII, aph IV, aadA, aac3, aacC4, bar, pat, DMO, EPSPS, aroA, luciferase, GFP, and GUS.

In an aspect, a cell provided herein is a eukaryotic cell. As used herein, a "eukaryotic cell" refers to a cell comprising a nucleus and membrane-bound organelles. In an aspect, a eukaryotic cell provided herein is selected from the group consisting of an animal cell, a plant cell, and a fungal cell. In another aspect, an animal cell provided herein is selected from the group consisting of a vertebrate cell and an invertebrate cell. In a further aspect, a vertebrate cell is selected from the group consisting of a mammal cell, a reptile cell, an amphibian cell, a bird cell, and a fish cell. In yet another aspect, an invertebrate cell provided herein is selected from the group consisting of an annelid cell, a mollusk cell, a nematode cell, an insect cell, and an arachnid cell.

In an aspect, a cell provided herein is a plant cell. In an aspect, a plant cell provided herein is an angiosperm plant cell. In another aspect, a plant cell provided herein is a gymnosperm plant cell. In an aspect, a plant cell provided herein is a monocotyledonous plant cell. In a further aspect, a plant cell provided herein is a dicotyledonous plant cell. In an aspect, a plant cell provided herein is a corn cell. In an aspect, a plant cell provided herein is a soybean cell. In an aspect, a plant cell provided herein is a canola cell. In an aspect, a plant cell provided herein is a cotton cell. In an aspect, a plant cell provided herein is a wheat cell. In an aspect, a plant cell provided herein is a sorghum cell. In an aspect, a plant cell provided herein is an alfalfa cell. In an aspect, a plant cell provided herein is a sugarcane cell. In an aspect, a plant cell provided herein is an *Arabidopsis* cell. In an aspect, a plant cell provided herein is a rice cell. In an aspect, a plant cell provided herein is a tomato cell. In an aspect, a plant cell provided herein is a cucumber cell. In an aspect, a plant cell provided herein is a potato cell. In an aspect, a plant cell provided herein is an algae cell.

In an aspect, a eukaryotic genome provided herein is a nuclear genome. In another aspect, a eukaryotic genome provided herein is a mitochondrial genome. In another aspect, a eukaryotic genome provided herein is a chloroplast genome. In an aspect, a eukaryotic genome provided herein is selected from the group consisting of an animal genome, a plant genome, and a fungal genome. In another aspect, an animal cell provided herein is selected from the group consisting of a vertebrate genome and an invertebrate genome. In a further aspect, a vertebrate genome is selected from the group consisting of a mammal genome, a reptile genome, an amphibian genome, a bird genome, and a fish genome. In yet another aspect, an invertebrate genome provided herein is selected from the group consisting of an annelid genome, a mollusk genome, a nematode genome, an insect genome, and an arachnid genome. In an aspect, a eukaryotic genome provided herein is a yeast genome.

In an aspect, a genome provided herein is a plant genome. In an aspect, a plant genome provided herein is an angiosperm plant genome. In another aspect, a plant genome provided herein is a gymnosperm plant genome. In an aspect, a plant genome provided herein is a monocotyledonous plant genome. In a further aspect, a plant genome provided herein is a dicotyledonous plant genome. In an aspect, a plant genome provided herein is a corn genome. In an aspect, a plant genome provided herein is a soybean genome. In an aspect, a plant genome provided herein is a canola genome. In an aspect, a plant genome provided herein is a cotton genome. In an aspect, a plant genome provided herein is a wheat genome. In an aspect, a plant genome provided herein is a sorghum genome. In an aspect, a plant genome provided herein is an alfalfa genome. In an aspect, a plant genome provided herein is a sugarcane genome. In an aspect, a plant genome provided herein is an *Arabidopsis* genome. In an aspect, a plant genome provided herein is a rice genome. In an aspect, a plant genome provided herein is a tomato genome. In an aspect, a plant genome provided herein is a cucumber genome. In an aspect, a plant genome provided herein is a potato genome. In an aspect, a plant genome provided herein is an algae genome.

As used herein, a "monocot" or "monocotyledonous" plant refers to an angiosperm whose seeds typically comprise one embryonic leaf (cotyledon). Non-limiting examples of monocots include the Orders Acorales, Alismatales, Asparagales, Dioscoreales, Liliales, Pandanales, Petrosaviales, Arecales, Commelinales, Poales, and Zingiberales. As used herein, a "dicot" or "dicotyledonous" plant refers to angiosperms whose seeds typically comprise two embryonic leaves. Non-limiting examples of dicots include the Orders Ranunculales, Fabales, Rosales, Cucurbitales, Brassicales, Asterales, and Solanales. As used herein, "angiosperm" refers to plant species that comprise flowers, endosperms within the seed, and production of fruits that comprise seeds. As used herein, "gymnosperm" refers to non-flowering plants such as, without being limiting, the Orders Cycadales, Ginkgoales, and Pinales.

As used herein, "plant" refers to a whole plant. A cell or tissue culture derived from a plant can comprise any plant components or plant organs (e.g., leaves, stems, roots, etc.), plant tissues, seeds, plant cells, and/or progeny of the same. A progeny plant can be from any filial generation, e.g., $F_1$, $F_2$, $F_3$, $F_4$, $F_5$, $F_6$, $F_7$, etc. A plant cell is a biological cell of a plant, taken from a plant or derived through culture from a cell taken from a plant.

In one aspect, a plant component provided herein includes, but is not limited to, a leaf, a stem, a root, a seed, a flower, pollen, an anther, an ovule, a pedicel, a fruit, a meristem, a cotyledon, a hypocotyl, a pod, an embryo, endosperm, an explant, a callus, a tissue culture, a shoot, a cell, and a protoplast. In further aspects, this disclosure provides plant cells, tissues, and organs that are not reproductive material and do not mediate the natural reproduction of the plant. In another aspect, this disclosure also provides plant cells, tissues, and organs that are reproductive material and mediate the natural reproduction of the plant. In another aspect, this disclosure provides plant cells, tissues, and organs that cannot maintain themselves via photosynthesis. In another aspect, this disclosure provides somatic plant cells. Somatic cells, contrary to germline cells, do not mediate plant reproduction.

Provided cells, tissues and organs can be from seed, fruit, leaf, cotyledon, hypocotyl, meristem, embryos, endosperm, root, shoot, stem, pod, flower, inflorescence, stalk, pedicel, style, stigma, receptacle, petal, sepal, pollen, anther, filament, ovary, ovule, pericarp, phloem, and vascular tissue. In another aspect, this disclosure provides a plant chloroplast. In a further aspect, this disclosure provides an epidermal cell, a stomata cell, a trichome cell, a root hair, or a storage root. In another aspect, this disclosure provides a protoplast.

In one aspect, methods and compositions provided herein comprise a vector. As used herein, the terms "vector" or "plasmid" are used interchangeably and refer to a circular, double-stranded DNA molecule that is physically separate from chromosomal DNA. In one aspect, a plasmid or vector used herein is capable of replication in vivo. A "transformation vector," as used herein, is a plasmid that is capable of transforming a plant cell. In an aspect, a plasmid provided herein is a bacterial plasmid. In another aspect, a plasmid provided herein is an *Agrobacterium* Ti plasmid or derived from an *Agrobacterium* Ti plasmid.

In one aspect, a plasmid or vector provided herein is a recombinant vector. As used herein, the term "recombinant vector" refers to a vector formed by laboratory methods of genetic recombination, such as molecular cloning. In another aspect, a plasmid provided herein is a synthetic plasmid. As used herein, a "synthetic plasmid" is an artificially created plasmid that is capable of the same functions (e.g., replication) as a natural plasmid (e.g., Ti plasmid). Without being limited, one skilled in the art can create a synthetic plasmid de novo via synthesizing a plasmid by individual nucleotides, or by splicing together nucleic acid molecules from different pre-existing plasmids.

As used herein, "modified," in the context of eukaryotic cells, eukaryotic genomes, and eukaryotic organisms, refers to a state containing changes or variations from their natural or native state. For instance, a "native transcript" of a gene refers to an RNA transcript that is generated from an unmodified gene. Typically, a native transcript is a sense transcript. Modified cells contain molecular changes in their genetic materials, including either genetic or epigenetic modifications. Typically, modified cells have been subjected to mutagenesis, genome editing (e.g., without being limiting, via methods using a CasX nuclease), genetic transformation (e.g., without being limiting, via methods of *Agrobacterium* transformation or microprojectile bombardment), or a combination thereof.

In an aspect, this disclosure provides a plant regenerated from a plant cell modified by a CasX nuclease. In another aspect, this disclosure provides a plant cell comprising a CasX nuclease. In a further aspect, this disclosure provides a plant cell comprising a nucleic acid molecule encoding a CasX nuclease.

In an aspect, this disclosure provides a eukaryotic cell derived from a eukaryotic cell modified by a CasX nuclease. In an aspect, this disclosure provides a eukaryotic cell comprising a CasX nuclease. In a further aspect, this disclosure provides a eukaryotic cell comprising a nucleic acid molecule encoding a CasX nuclease.

In an aspect, this disclosure provides a plant cell comprising an engineered system comprising: (a) a first nucleic acid molecule encoding a CasX nuclease, and (b) a guide RNA (gRNA) or a second nucleic acid molecule encoding the gRNA, where the first nucleic acid molecule is codon optimized for the plant cell, and where the gRNA is designed to hybridize with at least one target site in the plant cell. In another aspect, this disclosure provides a plant cell comprising an engineered system comprising: (a) a first nucleic acid molecule encoding a CasX nuclease, and (b) a single guide RNA (sgRNA) or a second nucleic acid molecule encoding the sgRNA, where the first nucleic acid molecule is codon optimized for the plant cell, and where the sgRNA is designed to hybridize with at least one target site in the plant cell.

In an aspect, this disclosure provides a eukaryotic cell comprising an engineered system comprising: (a) a first nucleic acid molecule encoding a CasX nuclease, and (b) a guide RNA (gRNA) or a second nucleic acid molecule encoding the gRNA, where the first nucleic acid molecule is codon optimized for the eukaryotic cell, and where the gRNA is designed to hybridize with at least one target site in the eukaryotic cell. In another aspect, this disclosure provides a eukaryotic cell comprising an engineered system comprising: (a) a first nucleic acid molecule encoding a CasX nuclease, and (b) a single guide RNA (sgRNA) or a second nucleic acid molecule encoding the sgRNA, where the first nucleic acid molecule is codon optimized for the eukaryotic cell, and where the sgRNA is designed to hybridize with at least one target site in the eukaryotic cell.

As used herein, a "locus" refers to a specific position on a chromosome or other nucleic acid molecule. Without being limiting, a locus can comprise a polynucleotide that encodes a protein or an RNA. A locus can also comprise a non-coding RNA. A locus can comprise a gene. A locus can comprise a promoter, a 5'-untranslated region (UTR), an exon, an intron, a 3'-UTR, or any combination thereof. A locus can comprise a coding region.

As used herein, a "gene" refers to a polynucleotide that can produce a functional unit (e.g., without being limiting, for example, a protein, or a non-coding RNA molecule). A gene can comprise a promoter, an enhancer sequence, a leader sequence, a transcriptional start site, a transcriptional stop site, a polyadenylation site, one or more exons, one or more introns, a 5'-UTR, a 3'-UTR, or any combination thereof. A "gene sequence" can comprise a polynucleotide sequence encoding a promoter, an enhancer sequence, a leader sequence, a transcriptional start site, a transcriptional stop site, a polyadenylation site, one or more exons, one or more introns, a 5'-UTR, a 3'-UTR, or any combination thereof. In one aspect, a gene encodes a non-protein-coding RNA molecule or a precursor thereof. In another aspect, a gene encodes a protein.

Non-limiting examples of a non-protein-coding RNA molecule include a microRNA (miRNA), a miRNA precursor (pre-miRNA), a small interfering RNA (siRNA), a small RNA (18-26 nt in length) and precursor encoding same, a heterochromatic siRNA (hc-siRNA), a Piwi-interacting RNA (piRNA), a hairpin double strand RNA (hairpin dsRNA), a trans-acting siRNA (ta-siRNA), a naturally occurring antisense siRNA (nat-siRNA), a CRISPR RNA (crRNA), a tracer RNA (tracrRNA), a guide RNA (gRNA), and a single guide RNA (sgRNA).

Genome editing, modification of a eukaryotic genome, or targeted editing can be effected via the use of a CasX nuclease. A CasX nuclease can induce a double-stranded break (DSB) at a target site of a genome sequence that is then repaired by the natural processes of either homologous recombination (HR) or non-homologous end-joining (NHEJ). Sequence modifications, such as insertions, deletions, can occur at the DSB locations via NHEJ repair. If two DSBs flanking one target region are created, the breaks can be repaired via NHEJ by reversing the orientation of the targeted DNA (also referred to as an "inversion"). HR can be used to integrate a donor nucleic acid sequence into a target site. In one aspect, a double-stranded break provided herein is repaired by NHEJ. In another aspect, a double-stranded break provided herein is repaired by HR.

As used herein a "donor molecule" is defined as a nucleic acid sequence that has been selected for targeted insertion into a eukaryotic genome at a cleavage generated by a CasX nuclease. In an aspect, a donor molecule comprises a "donor sequence." In an aspect, a donor sequence comprises a sequence that encodes a protein. In another aspect, a donor sequence comprises a sequence that encodes an RNA. In another aspect, a donor sequence comprises a sequence that encodes a non-protein-encoding RNA. In an aspect, a donor sequence can comprise a transgene or construct. In another aspect, a donor sequence is at least 99%, at least 98%, at least 97%, at least 96%, at least 95%, at least 94%, at least 93%, at least 92%, at least 91%, at least 90%, at least 85%, or at least 80% identical to the endogenous nucleic acid sequence at the target site. In an aspect, a donor molecule can comprise one or two homology arms to promote the targeted insertion event through homologous recombination and/or homology-directed repair. In an aspect, a modification provided herein comprises the insertion of a donor molecule into a target site. In an aspect, a method provided herein comprises providing at least one donor molecule to a eukaryotic cell.

As used herein, the term "homology arm" refers to a polynucleotide sequence that has at least 80%, at least 85%, at least 90%, at least 91%, at least 92%, at least 93%, at least 94%, at least 95%, at least 96%, at least 97%, at least 98%, at least 99% or 100% sequence identity to a target sequence in a eukaryotic genome or eukaryotic cell. A homology arm can comprise at least 5, at least 10, at least 15, at least 20, at least 25, at least 30, at least 40, at least 50, at least 100, at least 150, at least 200, at least 250, at least 300, at least 350, at least 400, at least 450, at least 500, at least 500, at least 550, at least 600, at least 650, at least 700, at least, 750, at least 800, at least 850, at least 900, at least 950, at least 1000, or at least 2500 nucleotides. Without being limited by any theory, homology arms allow a donor molecule to undergo homologous recombination with an endogenous locus, which allows the insertion of the donor molecule at a target site.

As used herein, a "target site" refers to a location of a polynucleotide sequence that is capable of being bound to and cleaved by a CasX/gRNA complex or a CasX/sgRNA complex, introducing a single-stranded break or a double stranded break into the nucleic acid backbone. In an aspect, a target site can comprise both the nucleic acid sequence bound by a sgRNA as well as at least 15, at least 16, at least 17, at least 18, at least 19, at least 20, at least 21, at least 22, at least 23, at least 24, or at least 25 nucleotides on each side of the sequence bound by a sgRNA. In an aspect, a target site can comprise both the nucleic acid sequence bound by a gRNA as well as at least 15, at least 16, at least 17, at least 18, at least 19, at least 20, at least 21, at least 22, at least 23, at least 24, or at least 25 nucleotides on each side of the sequence bound by a gRNA. In an aspect, a target site can comprise both the nucleic acid sequence bound by a crRNA as well as at least 15, at least 16, at least 17, at least 18, at least 19, at least 20, at least 21, at least 22, at least 23, at least 24, or at least 25 nucleotides on each side of the sequence bound by a crRNA. In an aspect, a target site comprises at least 30, at least 40, at least 50, at least 60, at least 70, at least 80, at least 90, at least 100, at least 125, at least 150, at least 175, or at least 200 nucleotides.

In one aspect, a gRNA provided herein is capable of targeting a single target site. In a further aspect, a gRNA provided herein is capable of targeting at least two, at least three, at least four, at least five, at least six, at least seven, at least eight, at least nine, or at least ten target sites. In another aspect, a sgRNA provided herein is capable of targeting a single target site. In a further aspect, a sgRNA provided herein is capable of targeting at least two, at least three, at least four, at least five, at least six, at least seven, at least eight, at least nine, or at least ten target sites.

In an aspect, a method or composition provided herein is capable of modifying at least one target site. In another aspect, a method or composition provided herein is capable of modifying at least two target sites. In another aspect, a method or composition provided herein is capable of modifying at least three target sites. In another aspect, a method or composition provided herein is capable of modifying at least four target sites. In another aspect, a method or composition provided herein is capable of modifying at least five target sites. In another aspect, a method or composition provided herein is capable of modifying at least six target sites. In another aspect, a method or composition provided herein is capable of modifying at least seven target sites. In another aspect, a method or composition provided herein is capable of modifying at least eight target sites. In another aspect, a method or composition provided herein is capable of modifying at least nine target sites. In another aspect, a method or composition provided herein is capable of modifying at least ten target sites.

In another aspect, a target site provided herein can comprise a protospacer adjacent motif (PAM). In an aspect, a PAM sequence provided herein comprises the nucleotide sequence 5'-TTCN-3'. In an aspect, a PAM sequence provided herein comprises the nucleotide sequence 5'-TTCA-3'. In another aspect, a PAM sequence provided herein comprises the nucleotide sequence 5'-TTC-3'.

As used herein, a "guide RNA" refers to any RNA molecule capable of forming a complex with a CasX nuclease to guide the CasX nuclease to a target site. In an aspect, a gRNA provided herein is a single guide RNA (sgRNA).

In an aspect, this disclosure provides a gRNA or a nucleic acid molecule encoding a gRNA. In one aspect, a gRNA provided herein is capable of forming a complex with a CasX nuclease. In another aspect, a gRNA provided herein comprises a nucleotide sequence that is identical or complementary to a target site. In an aspect, a gRNA provided herein comprises a crRNA. In another aspect, a gRNA provided herein comprises a tracrRNA. In a further aspect, a sgRNA provided herein comprises a pentaloop sequence. In another aspect, a gRNA provided herein comprise a tetraloop sequence. In still a further aspect, a gRNA provided herein comprises a variable spacer sequence. In yet a further aspect, a gRNA provided herein comprises a repeat sequence. In one aspect, a gRNA provided herein comprises a crRNA and a tracrRNA. In a further aspect, a gRNA provided herein comprises a crRNA, a tracrRNA, and a pentaloop sequence. In an aspect, a nucleic acid sequence encoding a gRNA is operably linked to a promoter. In another aspect, a nucleic acid sequence encoding a gRNA is located on a recombinant DNA vector.

In an aspect, a gRNA provided herein comprises a tracrRNA and a crRNA that are assembled into a single guide RNA in vitro. In an aspect, a gRNA provided herein comprises a tracrRNA and a crRNA that are assembled into a single guide RNA in vivo. In an aspect, a gRNA provided herein comprises a tracrRNA and a crRNA that are assembled into a single guide RNA ex vivo.

In an aspect, this disclosure provides a sgRNA or a nucleic acid molecule encoding a sgRNA. In one aspect, a sgRNA provided herein is capable of forming a complex with a CasX nuclease. In another aspect, a sgRNA provided herein comprises a nucleotide sequence that is identical or complementary to a target site. In an aspect, a sgRNA provided herein comprises a crRNA wherein the crRNA comprises a repeat and a variable spacer. In another aspect, a sgRNA provided herein comprises a tracrRNA. In a further aspect, a sgRNA provided herein comprises a pentaloop sequence. In another aspect, a sgRNA provided herein comprise a tetraloop sequence. In still a further aspect, a sgRNA provided herein comprises a repeat sequence. In still a further aspect, a sgRNA provided herein comprises a variable spacer sequence. In one aspect, a sgRNA provided herein comprises a crRNA and a tracrRNA. In a further aspect, a sgRNA provided herein comprises a crRNA, a tracrRNA, and a pentaloop sequence. In an aspect, a nucleic acid sequence encoding a sgRNA is operably linked to a promoter. In another aspect, a nucleic acid sequence encoding a sgRNA is located on a recombinant DNA vector.

As used herein, "pentaloop" refers to a five nucleotide long nucleic acid sequence useful as a spacer sequence between a crRNA and a tracrRNA. As used herein, "tetraloop" refers to a four nucleotide long nucleic acid sequence useful as a spacer sequence between a crRNA and a tracrRNA. As used herein, a crRNA comprises a repeat sequence and a variable spacer sequence. As used herein, "repeat sequence" refers to a sequence that can hybridize to a tracrRNA. As used herein, a "variable spacer sequence" refers to a sequence that can hybridize to a target site.

In an aspect, a repeat sequence provided herein comprises at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, or at least 50 nucleotides. In another aspect, a repeat sequence provided herein comprises at least 10 nucleotides. In another aspect, a repeat sequence provided herein comprises at least 15 nucleotides. In another aspect, a repeat sequence provided herein comprises at least 16 nucleotides. In another aspect, a repeat sequence provided herein comprises at least 17 nucleotides. In another aspect, a repeat sequence provided herein comprises at least 18 nucleotides. In another aspect, a repeat sequence provided herein comprises at least 19 nucleotides. In another aspect, a repeat sequence provided herein comprises at least 20 nucleotides. In another aspect, a repeat sequence provided herein comprises at least 21 nucleotides. In another aspect, a repeat sequence provided herein comprises at least 22 nucleotides. In another aspect, a repeat sequence provided herein comprises at least 23 nucleotides. In another aspect, a repeat sequence provided herein comprises at least 24 nucleotides. In another aspect, a repeat sequence provided herein comprises at least 25 nucleotides. In another aspect, a repeat sequence provided herein comprises at least 26 nucleotides. In another aspect, a repeat sequence provided herein comprises at least 27 nucleotides. In another aspect, a repeat sequence provided herein comprises at least 28 nucleotides. In another aspect, a repeat sequence provided herein comprises at least 29 nucleotides. In another aspect, a repeat sequence provided herein comprises at least 30 nucleotides. In another aspect, a repeat sequence provided herein comprises at least 35 nucleotides. In another aspect, a repeat sequence provided herein comprises at least 40 nucleotides. In another aspect, a repeat sequence provided herein comprises at least 50 nucleotides.

In an aspect, a variable spacer sequence provided herein comprises at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, or at least 50 nucleotides. In another aspect, a variable spacer sequence provided herein comprises at least 15 nucleotides. In another aspect, a variable spacer sequence provided herein comprises at least 16 nucleotides. In another aspect, a variable spacer sequence provided herein comprises at least 17 nucleotides. In another aspect, a variable spacer sequence provided herein comprises at least 18 nucleotides. In another aspect, a variable spacer sequence provided herein comprises at least 19 nucleotides. In another aspect, a variable spacer sequence provided herein comprises at least 20 nucleotides. In another aspect, a variable spacer sequence provided herein comprises at least 21 nucleotides. In another aspect, a variable spacer sequence provided herein comprises at least 22 nucleotides. In another aspect, a variable spacer sequence provided herein comprises at least 23 nucleotides. In another aspect, a variable spacer sequence provided herein comprises at least 24 nucleotides. In another aspect, a variable spacer sequence provided herein comprises at least 25 nucleotides. In another aspect, a variable spacer sequence provided herein comprises at least 26 nucleotides. In another aspect, a variable spacer sequence provided herein comprises at least 27 nucleotides. In another aspect, a variable spacer sequence provided herein comprises at least 28 nucleotides. In another aspect, a variable spacer sequence provided herein comprises at least 29 nucleotides. In another aspect, a variable spacer sequence provided herein comprises at least 30 nucleotides. In another aspect, a variable spacer sequence provided herein comprises at least 31 nucleotides. In another aspect, a variable spacer sequence provided herein comprises at least 32 nucleotides. In another aspect, a variable spacer sequence provided herein comprises at least 33 nucleotides. In another aspect, a variable spacer sequence provided herein comprises at least 34 nucleotides. In another aspect, a variable spacer sequence provided herein comprises at least 35 nucleotides. In another aspect, a variable spacer sequence provided herein comprises at least 36 nucleotides. In another aspect, a variable spacer sequence provided herein comprises at least 37 nucleotides. In another aspect, a variable spacer sequence provided herein comprises at least 38 nucleotides. In another aspect, a variable spacer sequence provided herein comprises at least 39 nucleotides. In another aspect, a variable spacer sequence provided herein comprises at least 40 nucleotides. In another aspect, a variable spacer sequence provided herein comprises at least 45 nucleotides. In another aspect, a variable spacer sequence provided herein comprises at least 50 nucleotides.

In an aspect, a tracrRNA provided herein comprises at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 45, at least 50, at least 55, at least 60, at least 65, at least 70, at least 75, at least 80, at least 85, at least 90, at least 95, or at least 100 nucleotides. In another aspect, a crRNA provided herein comprises at least 15 nucleotides. In another aspect, a crRNA provided herein comprises at least 16 nucleotides. In another aspect, a crRNA provided herein comprises at least 17 nucleotides. In another aspect, a crRNA provided herein comprises at least 18 nucleotides. In another aspect, a crRNA provided herein comprises at least 19 nucleotides. In another aspect, a crRNA provided herein comprises at least 20 nucleotides. In another aspect, a crRNA provided herein comprises at least 21 nucleotides. In another aspect, a crRNA provided herein comprises at least 22 nucleotides. In another aspect, a crRNA provided herein comprises at least 23 nucleotides. In another aspect, a crRNA provided herein comprises at least 24 nucleotides. In another aspect, a crRNA provided herein comprises at least 25 nucleotides. In another aspect, a crRNA provided herein comprises at least 26 nucleotides. In another aspect, a crRNA provided herein comprises at least 27 nucleotides. In another aspect, a crRNA provided herein comprises at least 28 nucleotides. In another aspect, a crRNA provided herein comprises at least 29 nucleotides. In another aspect, a crRNA provided herein comprises at least 30 nucleotides. In another aspect, a crRNA provided herein comprises at least 31 nucleotides. In another aspect, a crRNA provided herein comprises at least 32 nucleotides. In another aspect, a crRNA provided herein comprises at least 33 nucleotides. In another aspect, a crRNA provided herein comprises at least 34 nucleotides. In another aspect, a crRNA provided herein comprises at least 35 nucleotides. In another aspect, a crRNA provided herein comprises at least 36 nucleotides. In another aspect, a crRNA provided herein comprises at least 37 nucleotides. In another aspect, a crRNA provided herein comprises at least 38 nucleotides. In another aspect, a crRNA provided herein comprises at least 39 nucleotides. In another aspect, a crRNA provided herein comprises at least 40 nucleotides. In another aspect, a crRNA provided herein comprises at least 45 nucleotides. In another aspect, a crRNA provided herein comprises at least 50 nucleotides. In another aspect, a crRNA provided herein comprises at least 60 nucleotides. In another aspect, a crRNA provided herein comprises at least 70 nucleotides. In another aspect, a crRNA provided herein comprises at least 80 nucleotides. In another aspect, a crRNA provided herein comprises at least 90 nucleotides. In another aspect, a crRNA provided herein comprises at least 100 nucleotides.

In an aspect, a tracrRNA provided herein comprises at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 45, at least 50, at least 55, at least 60, at least 65, at least 70, at least 75, at least 80, at least 85, at least 90, at least 95, or at least 100 nucleotides. In another aspect, a tracrRNA provided herein comprises at least 15 nucleotides. In another aspect, a tracrRNA provided herein comprises at least 16 nucleotides. In another aspect, a tracrRNA provided herein comprises at least 17 nucleotides. In another aspect, a tracrRNA provided herein comprises at least 18 nucleotides. In another aspect, a tracrRNA provided herein comprises at least 19 nucleotides. In another aspect, a tracrRNA provided herein comprises at least 20 nucleotides. In another aspect, a tracrRNA provided herein comprises at least 21 nucleotides. In another aspect, a tracrRNA provided herein comprises at least 22 nucleotides. In another aspect, a tracrRNA provided herein comprises at least 23 nucleotides. In another aspect, a tracrRNA provided herein comprises at least 24 nucleotides. In another aspect, a tracrRNA provided herein comprises at least 25 nucleotides. In another aspect, a tracrRNA provided herein comprises at least 26 nucleotides. In another aspect, a tracrRNA provided herein comprises at least 27 nucleotides. In another aspect, a tracrRNA provided herein comprises at least 28 nucleotides. In another aspect, a tracrRNA provided herein comprises at least 29 nucleotides. In another aspect, a tracrRNA provided herein comprises at least 30 nucleotides. In another aspect, a tracrRNA provided herein comprises at least 31 nucleotides. In another aspect, a tracrRNA provided herein comprises at least 32 nucleotides. In another aspect, a tracrRNA provided herein comprises at least 33 nucleotides. In another aspect, a tracrRNA provided herein comprises at least 34 nucleotides. In another aspect, a tracrRNA provided herein comprises at least 35 nucleotides. In another aspect, a tracrRNA provided herein comprises at least 36 nucleotides. In another aspect, a tracrRNA provided herein comprises at least 37 nucleotides. In another aspect, a tracrRNA provided herein comprises at least 38 nucleotides. In another aspect, a tracrRNA provided herein comprises at least 39 nucleotides. In another aspect, a tracrRNA provided herein comprises at least 40 nucleotides. In another aspect, a tracrRNA provided herein comprises at least 45 nucleotides. In another aspect, a tracrRNA provided herein comprises at least 50 nucleotides. In another aspect, a tracrRNA provided herein comprises at least 60 nucleotides. In another aspect, a tracrRNA provided herein comprises at least 70 nucleotides. In another aspect, a tracrRNA provided herein comprises at least 80 nucleotides. In another aspect, a tracrRNA provided herein comprises at least 90 nucleotides. In another aspect, a tracrRNA provided herein comprises at least 100 nucleotides.

In an aspect, a gRNA provided herein comprises at least 5, at least 10, at least 15, at least 20, at least 25, at least 30, at least 35, at least 40, at least 50, at least 60, at least 70, at least 80, at least 90, at least 100, at least 110, at least 120, at least 130, at least 140, at least 150, at least 160, at least 170, or at least 180 nucleotides. In another aspect, a gRNA provided herein comprises at least 20 nucleotides. In another aspect, a gRNA provided herein comprises at least 30 nucleotides. In another aspect, a gRNA provided herein comprises at least 40 nucleotides. In another aspect, a gRNA provided herein comprises at least 50 nucleotides. In another aspect, a gRNA provided herein comprises at least 60 nucleotides. In another aspect, a gRNA provided herein comprises at least 70 nucleotides. In another aspect, a gRNA provided herein comprises at least 80 nucleotides. In another aspect, a gRNA provided herein comprises at least 90 nucleotides. In another aspect, a gRNA provided herein comprises at least 100 nucleotides. In another aspect, a gRNA provided herein comprises at least 110 nucleotides. In another aspect, a gRNA provided herein comprises at least 120 nucleotides. In another aspect, a gRNA provided herein comprises at least 130 nucleotides. In another aspect, a gRNA provided herein comprises at least 140 nucleotides. In another aspect, a gRNA provided herein comprises at least 150 nucleotides. In another aspect, a gRNA provided herein comprises at least 160 nucleotides. In another aspect, a gRNA provided herein comprises at least 170 nucleotides. In another aspect, a gRNA provided herein comprises at least 180 nucleotides. In another aspect, a gRNA provided herein comprises at least 190 nucleotides. In another aspect, a gRNA provided herein comprises at least 200 nucleotides.

In an aspect, a sgRNA provided herein comprises at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 50, at least 60, at least 70, at least 80, at least 90, at least 100, at least 110, at least 120, at least 130, at least 140, at least 150, at least 160, at least 170, or at least 180 nucleotides. In another aspect, a sgRNA provided herein comprises at least 20 nucleotides. In another aspect, a sgRNA provided herein comprises at least 30 nucleotides. In another aspect, a sgRNA provided herein comprises at least 40 nucleotides. In another aspect, a sgRNA provided herein comprises at least 50 nucleotides. In another aspect, a sgRNA provided herein comprises at least 60 nucleotides. In another aspect, a sgRNA provided herein comprises at least 70 nucleotides. In another aspect, a sgRNA provided herein comprises at least 80 nucleotides. In another aspect, a sgRNA provided herein comprises at least 90 nucleotides. In another aspect, a sgRNA provided herein comprises at least 100 nucleotides. In another aspect, a sgRNA provided herein comprises at least 110 nucleotides. In another aspect, a sgRNA provided herein comprises at least 120 nucleotides. In another aspect, a sgRNA provided herein comprises at least 130 nucleotides. In another aspect, a sgRNA provided herein comprises at least 140 nucleotides. In another aspect, a sgRNA provided herein comprises at least 150 nucleotides. In another aspect, a sgRNA provided herein comprises at least 160 nucleotides. In another aspect, a sgRNA provided herein comprises at least 170 nucleotides. In another aspect, a sgRNA provided herein comprises at least 180 nucleotides. In another aspect, a sgRNA provided herein comprises at least 190 nucleotides. In another aspect, a sgRNA provided herein comprises at least 200 nucleotides.

In an aspect, a sgRNA provided herein comprises SEQ ID NO: 18. In another aspect, a sgRNA provided herein comprises SEQ ID NO: 19. In another aspect, a sgRNA provided herein comprises SEQ ID NO: 20. In an aspect, a gRNA provided herein comprises SEQ ID NO: 18. In another aspect, a gRNA provided herein comprises SEQ ID NO: 19. In another aspect, a gRNA provided herein comprises SEQ ID NO: 20.

In an aspect, a crRNA provided herein comprises at least 10, at least 20, at least 30, at least 40, at least 50, or at least 60 nucleotides. In another aspect, a tracrRNA provided herein comprises at least 10, at least 20, at least 30, at least 40, at least 50, at least 60, at least 70, at least 80, at least 90, at least 100, at least 110, at least 120, at least 130, at least 140, or at least 150 nucleotides.

In an aspect, a gRNA provided herein comprises a sequence that is 100% identical or complementary to a target site. In another aspect, a gRNA provided herein comprises a sequence that is at least 80% identical or complementary to a target site. In another aspect, a gRNA provided herein comprises a sequence that is at least 85% identical or complementary to a target site. In another aspect, a gRNA provided herein comprises a sequence that is at least 90% identical or complementary to a target site. In another aspect, a gRNA provided herein comprises a sequence that is at least 95% identical or complementary to a target site. In another aspect, a gRNA provided herein comprises a sequence that is at least 96% identical or complementary to a target site. In another aspect, a gRNA provided herein comprises a sequence that is at least 97% identical or complementary to a target site. In another aspect, a gRNA provided herein comprises a sequence that is at least 98% identical or complementary to a target site. In another aspect, a gRNA provided herein comprises a sequence that is at least 99% identical or complementary to a target site.

In an aspect, a sgRNA provided herein comprises a sequence that is 100% identical or complementary to a target site. In another aspect, a sgRNA provided herein comprises a sequence that is at least 80% identical or complementary to a target site. In another aspect, a sgRNA provided herein comprises a sequence that is at least 85% identical or complementary to a target site. In another aspect, a sgRNA provided herein comprises a sequence that is at least 90% identical or complementary to a target site. In another aspect, a sgRNA provided herein comprises a sequence that is at least 95% identical or complementary to a target site. In another aspect, a sgRNA provided herein comprises a sequence that is at least 96% identical or complementary to a target site. In another aspect, a sgRNA provided herein comprises a sequence that is at least 97% identical or complementary to a target site. In another aspect, a sgRNA provided herein comprises a sequence that is at least 98% identical or complementary to a target site. In another aspect, a sgRNA provided herein comprises a sequence that is at least 99% identical or complementary to a target site.

In an aspect, a crRNA provided herein comprises a sequence that is 100% identical or complementary to a target site. In another aspect, a crRNA provided herein comprises a sequence that is at least 80% identical or complementary to a target site. In another aspect, a crRNA provided herein comprises a sequence that is at least 85% identical or complementary to a target site. In another aspect, a crRNA provided herein comprises a sequence that is at least 90% identical or complementary to a target site. In another aspect, a crRNA provided herein comprises a sequence that is at least 95% identical or complementary to a target site. In another aspect, a crRNA provided herein comprises a sequence that is at least 96% identical or complementary to a target site. In another aspect, a crRNA provided herein comprises a sequence that is at least 97% identical or complementary to a target site. In another aspect, a crRNA provided herein comprises a sequence that is at least 98% identical or complementary to a target site. In another aspect, a crRNA provided herein comprises a sequence that is at least 99% identical or complementary to a target site.

A target site can be positioned in a polynucleotide sequence encoding a leader, an enhancer, a transcriptional start site, a promoter, a 5'-UTR, an exon, an intron, a 3'-UTR, a polyadenylation site, or a termination sequence. It will be appreciated that a target site can be also be positioned upstream or downstream of a sequence encoding a leader, an enhancer, a transcriptional start site, a promoter, a 5'-UTR, an exon, an intron, a 3'-UTR, a polyadenylation site, or a termination sequence. In one aspect, a target site is positioned within 10, within 20, within 30, within 40, within 50, within 75, within 100, within 125, within 150, within 200, within 250, within 300, within 400, within 500, within 600, within 700, within 800, within 900, within 1000, within 1250, within 1500, within 2000, within 2500, within 5000, within 10,000, or within 25,000 nucleotides of a polynucleotide encoding a leader, an enhancer, a transcriptional start site, a promoter, a 5'-UTR, an exon, an intron, a 3'-UTR, a polyadenylation site, a gene, or a termination sequence.

Polynucleotides encoding multiple gRNAs or sgRNAs can be produced to form complexes with CasX proteins and target multiple target sites at the same time. In an aspect, a polynucleotide provided herein encodes one gRNA. In another aspect, a polynucleotide provided herein encodes at least one, at least two, at least three, at least four, at least five, at least six, at least seven, at least eight, at least nine, or at least ten gRNAs. In an aspect, a polynucleotide provided herein encodes a gRNA array. As used herein, a "gRNA array" comprises at least two discrete guide RNAs that are capable of binding to the same or different target sites. One of skill in the art would recognize that a guide RNA array can contain any number of discrete gRNAs, including at least three, at least four, at least five, at least six, at least seven, at least eight, at least nine, or at least ten gRNAs.

In an aspect, a polynucleotide provided herein encodes one sgRNA. In another aspect, a polynucleotide provided herein encodes at least one, at least two, at least three, at least four, at least five, at least six, at least seven, at least eight, at least nine, or at least ten sgRNAs. In an aspect, a polynucleotide provided herein encodes a sgRNA array. As used herein, a "sgRNA array" comprises at least two sgRNAs that are capable of binding to the same or different target sites. One of skill in the art would recognize that a guide RNA array can contain any number of discrete sg RNAs, including at least three, at least four, at least five, at least six, at least seven, at least eight, at least nine, or at least ten sgRNAs.

According to an aspect of the present application, methods for transforming a eukaryotic cell with a recombinant DNA molecule or construct can further include site-directed or targeted integration using CasX. According to these methods, a portion of a recombinant DNA donor molecule (e.g., an insertion sequence) can be inserted or integrated at a target site within a genome.

The screening and selection of modified cells can be through any methodologies known to those having ordinary skill in the art. Examples of screening and selection methodologies include, but are not limited to, Southern analysis, PCR amplification for detection of a polynucleotide, Northern blots, RNase protection, primer-extension, RT-PCR amplification for detecting RNA transcripts, Sanger sequencing, Next Generation sequencing technologies (e.g., Illumina, PacBio, Ion Torrent, 454) enzymatic assays for detecting enzyme or ribozyme activity of polypeptides and polynucleotides, and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known.

Any method provided herein can involve transient transfection or stable transformation of a eukaryotic cell of interest (e.g., a plant cell). In an aspect, a nucleic acid molecule encoding a CasX nuclease is stably transformed. In another aspect, a nucleic acid molecule encoding a CasX nuclease is transiently transfected. In an aspect, a nucleic acid molecule encoding a gRNA is stably transformed. In another aspect, a nucleic acid molecule encoding a gRNA is transiently transfected. In an aspect, a nucleic acid molecule encoding a sgRNA is stably transformed. In another aspect, a nucleic acid molecule encoding a sgRNA is transiently transfected.

Numerous methods for transforming chromosomes or plastids in a plant cell with a recombinant DNA molecule or construct are known in the art, which can be used according to methods of the present application to produce a transgenic plant cell and plant. Any suitable method or technique for transformation of a plant cell known in the art can be used according to present methods. Effective methods for transformation of plants include bacterially mediated transformation, such as *Agrobacterium*-mediated or *Rhizobium*-mediated transformation and microprojectile bombardment-mediated transformation. A variety of methods are known in the art for transforming explants with a transformation vector via bacterially mediated transformation or microprojectile bombardment and then subsequently culturing, etc., those explants to regenerate or develop transgenic plants. Other methods for plant transformation, such as microinjection, electroporation, vacuum infiltration, pressure, sonication, silicon carbide fiber agitation, PEG-mediated transformation, etc., are also known in the art. Transgenic plants produced by these transformation methods can be chimeric or non-chimeric for the transformation event depending on the methods and explants used.

Methods of transforming plant cells are well known by persons of ordinary skill in the art. For instance, specific instructions for transforming plant cells by microprojectile bombardment with particles coated with recombinant DNA (e.g., biolistic transformation) are found in U.S. Pat. Nos. 5,550,318; 5,538,880 6,160,208; 6,399,861; and 6,153,812 and *Agrobacterium*-mediated transformation is described in U.S. Pat. Nos. 5,159,135; 5,824,877; 5,591,616; 6,384,301; 5,750,871; 5,463,174; and 5,188,958, all of which are incorporated herein by reference. Additional methods for transforming plants can be found in, for example, Compendium of Transgenic Crop Plants (2009) Blackwell Publishing. Any appropriate method known to those skilled in the art can be used to transform a plant cell with any of the nucleic acid molecules provided herein.

In an aspect, a method of providing a nucleic acid molecule to a cell comprises *Agrobacterium*-mediated transformation. In another aspect, a method of providing a nucleic acid molecule to a cell comprises polyethylene glycol (PEG)-mediated transformation. In another aspect, a method of providing a nucleic acid molecule to a cell comprises biolistic transformation. In another aspect, a method of providing a nucleic acid molecule to a cell comprises liposome-mediated transfection (lipofection). In another aspect, a method of providing a nucleic acid molecule to a cell comprises lentiviral transfection.

Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g. in vitro or ex vivo administration) or target tissues (e.g. in vivo administration).

Delivery vehicles, vectors, particles, nanoparticles, formulations and components thereof for expression of one or more elements of a nucleic acid molecule or a protein are as used in WO 2014/093622 (PCT/US2013/074667). In an aspect, a method of providing a nucleic acid molecule or a protein to a cell comprises delivery via a delivery particle. In an aspect, a method of providing a nucleic acid molecule or a protein to a cell comprises delivery via a delivery vesicle. In an aspect, a delivery vesicle is selected from the group consisting of an exosome and a liposome. In an aspect, a method of providing a nucleic acid molecule or a protein to a cell comprises delivery via a viral vector. In an aspect, a viral vector is selected from the group consisting of an adenovirus vector, a lentivirus vector, and an adeno-associated viral vector. In another aspect, a method providing a nucleic acid molecule or a protein to a cell comprises delivery via a nanoparticle. In an aspect, a method providing a nucleic acid molecule or a protein to a cell comprises microinjection. In an aspect, a method providing a nucleic acid molecule or a protein to a cell comprises polycations. In an aspect, a method providing a nucleic acid molecule or a protein to a cell comprises a cationic oligopeptide.

Recipient cell or explant targets for transformation include, but are not limited to, a seed cell, a fruit cell, a leaf cell, a cotyledon cell, a hypocotyl cell, a meristem cell, an embryo cell, an endosperm cell, a root cell, a shoot cell, a stem cell, a pod cell, a flower cell, an inflorescence cell, a stalk cell, a pedicel cell, a style cell, a stigma cell, a receptacle cell, a petal cell, a sepal cell, a pollen cell, an anther cell, a filament cell, an ovary cell, an ovule cell, a pericarp cell, a phloem cell, a bud cell, or a vascular tissue cell. In another aspect, this disclosure provides a plant chloroplast. In a further aspect, this disclosure provides an epidermal cell, a stomata cell, a trichome cell, a root hair cell, a storage root cell, or a tuber cell. In another aspect, this disclosure provides a protoplast. In another aspect, this disclosure provides a plant callus cell. Any cell from which a fertile plant can be regenerated is contemplated as a useful recipient cell for practice of this disclosure. Callus can be initiated from various tissue sources, including, but not limited to, immature embryos or parts of embryos, seedling apical meristems, microspores, and the like. Those cells which are capable of proliferating as callus can serve as recipient cells for transformation. Practical transformation methods and materials for making transgenic plants of this disclosure (e.g., various media and recipient target cells, transformation of immature embryos, and subsequent regeneration of fertile transgenic plants) are disclosed, for example, in U.S. Pat. Nos. 6,194,636 and 6,232,526 and U. S. Patent Application Publication 2004/0216189, all of which are incorporated herein by reference. Transformed explants, cells or tissues can be subjected to additional culturing steps, such as callus induction, selection, regeneration, etc., as known in the art. Transformed cells, tissues or explants containing a recombinant DNA insertion can be grown, developed or regenerated into transgenic plants in culture, plugs or soil according to methods known in the art. In one aspect, this disclosure provides plant cells that are not reproductive material and do not mediate the natural reproduction of the plant. In another aspect, this disclosure also provides plant cells that are reproductive material and mediate the natural reproduction of the plant. In another aspect, this disclosure provides plant cells that cannot maintain themselves via photosynthesis. In another aspect, this disclosure provides somatic plant cells. Somatic cells, contrary to germline cells, do not mediate plant reproduction. In one aspect, this disclosure provides a non-reproductive plant cell.

As used herein, "codon optimization" refers to a process of modifying a nucleic acid sequence for enhanced expression in a host cell of interest by replacing at least one codon (e.g., at least 1, 2, 3, 4, 5, 10, 15, 20, 25, 50, or more codons) of a sequence with codons that are more frequently or most frequently used in the genes of the host cell while maintaining the original amino acid sequence (e.g., introducing silent mutations). Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www[dot]kazusa[dot]or[dot]jp[forwards slash] codon and these tables can be adapted in a number of ways. See Nakamura et al., 2000, *Nucl. Acids Res.* 28:292. Computer algorithms for codon optimizing a particular sequence for expression in a particular host cell are also available, such as Gene Forge (Aptagen; Jacobus, Pa.), are also available. In some embodiments, one or more codons (e.g., 1, 2, 3, 4, 5, 10, 15, 20, 25, 50, or more, or all codons) in a sequence encoding a CasX nuclease correspond to the most frequently used codon for a particular amino acid. As to codon usage in plants, including algae, reference is made to Campbell and Gowri, 1990, *Plant Physiol.*, 92: 1-11; and Murray et al., 1989, *Nucleic Acids Res.*, 17:477-98, each of which is incorporated herein by reference in their entireties.

In one aspect, a nucleic acid molecule provided herein encodes a CasX nuclease that is codon optimized for a eukaryotic cell. In an aspect, a nucleic acid molecule provided herein is codon optimized for an animal cell. In an aspect, a nucleic acid molecule provided herein is codon optimized for a fungus cell. In another aspect, a nucleic acid molecule provided herein encodes a CasX nuclease that is codon optimized for a plant cell. In another aspect, a nucleic acid molecule provided herein encodes a CasX nuclease that is codon optimized for a monocotyledonous plant species. In another aspect, a protein-coding nucleic acid molecule is codon optimized for a dicotyledonous plant species. In a further aspect, a nucleic acid molecule provided herein encodes a CasX nuclease that is codon optimized for a gymnosperm plant species. In a further aspect, a nucleic acid molecule provided herein encodes a CasX nuclease that is codon optimized for an angiosperm plant species. In a further aspect, a nucleic acid molecule provided herein encodes a CasX nuclease that is codon optimized for a corn cell. In a further aspect, a nucleic acid molecule provided herein encodes a CasX nuclease that is codon optimized for a soybean cell. In a further aspect, a nucleic acid molecule provided herein encodes a CasX nuclease that is codon optimized for a rice cell. In a further aspect, a nucleic acid molecule provided herein encodes a CasX nuclease that is codon optimized for a wheat cell. In a further aspect, a nucleic acid molecule provided herein encodes a CasX nuclease that is codon optimized for a cotton cell. In a further aspect, a nucleic acid molecule provided herein encodes a CasX nuclease that is codon optimized for a sorghum cell. In a further aspect, a nucleic acid molecule provided herein encodes a CasX nuclease that is codon optimized for an alfalfa cell. In a further aspect, a nucleic acid molecule provided herein encodes a CasX nuclease that is codon optimized for a sugar cane cell. In a further aspect, a nucleic acid molecule provided herein encodes a CasX nuclease that is codon optimized for an *Arabidopsis* cell. In a further aspect, a nucleic acid molecule provided herein encodes a CasX nuclease that is codon optimized for a tomato cell. In a further aspect, a nucleic acid molecule provided herein encodes a CasX nuclease that is codon optimized for a cucumber cell. In a further aspect, a nucleic acid molecule provided herein encodes a CasX nuclease that is codon optimized for a potato cell. In a further aspect, a nucleic acid molecule provided herein encodes a CasX nuclease that is codon optimized for an algae cell.

EXAMPLES

Example 1. Engineering a Programmable, RNA-Guided CasX Endonuclease to Introduce Modifications at a Specific Target Site within the Soybean Genome The Deltaproteobacteria CasX protein (SEQ ID NO:1) was shown to be a functional DNA targeting, RNA-guided CRISPR-associated protein in prokaryotic systems (see Burstein et al.). It remains unknown if the CasX protein is functional in eukaryotic systems. An assay was successfully performed to show that the CasX protein can be engineered to function as a programmable RNA-guided endonuclease in eukaryotic cells, specifically in soybean (*Glycine max*) cells. The experimental details are described below.

Construction and Design of a Plant Vector for the Expression of Codon-Optimized Cas X Protein:

As a first step, the nucleotide sequence of Deltaproteobacteria CasX disclosed by Burstein et. al. (SEQ ID NO:2) was analyzed and the open reading frame was codon-optimized for optimal expression in soybean. The codon optimized variant, referred to as DsCasX_Gm (Deltaproteobacteria sp. CasX_Gm) (SEQ ID NO:3), was introduced into a plant expression vector. The T-DNA vector comprised two expression cassettes between left border (LB) and right border (RB) sequences. The first expression cassette (SEQ ID NO: 5) comprised the DsCasX_Gm cassette (SEQ ID NO:9) operably linked to a Dahlia Mosaic virus promoter cassette (SEQ ID NOs:6-8) and a *Medicago truncatula* transcription terminator sequence (SEQ ID NO:4). The DsCasX_Gm cassette sequence comprised N- and C-terminal nuclear localization signals (SEQ ID NO: 10) and an intron (SEQ ID NO: 12) that divided the DsCasX_Gm open reading frame into a 5'-portion (SEQ ID NO: 11) and 3'-portion (SEQ ID NO: 13).

The second expression cassette comprised an *Arabidopsis thaliana* actin promoter operably linked to an *E. coli* adenylyltransferase gene (aadA). The aadA gene provides resistance against spectinomycin and served as a selectable marker.

Selection of Target Sites in the Soy Genome:

Three target sites were selected within the Soybean Cyst Nematode (SCN) resistance locus, Rhg1 (see Cook et al., 2012, *Science*, 338:1206-1209, which is incorporated herein by reference in its entirety). Without being limiting, the CasX protein shows a preference for the PAM sequence 5'-TTCN-3' at the 5' end of the target site. Therefore, target sites were chosen based on the occurrence of the appropriate PAM site at the 5' end (see Table 1). The Rhg1 locus comprises 3 distinct genes that contribute to SCN resistance. The target site Rhg1_TS1 (SEQ ID NO:14) is located within the 5' UTR of one of the genes that encodes a protein homologous to alpha-soluble NSF attachment proteins. Rhg1_TS2 (SEQ ID NO:15) is located within the first exon of the same gene. Rhg1_TS3 (SEQ ID NO:16) is positioned within the promoter region of a second gene that encodes a protein belonging to the PLAC8 metal transporter superfamily.

TABLE 1

Annotated sequences of the target sites and guide RNAs.

| SEQ ID NO: | Description | Nucleic acid or protein | Sequence |
|---|---|---|---|
| 14 | Rhg1_TS1 (Target site 1 within the Rhg1 locus) from *Glycine max*. The PAM sequence is underlined. | DNA | TTCTGAATTTGCGGGTTTTGGATT |
| 15 | Rhg1_TS2 (Target site 2 within the Rhg1 locus) from *Glycine max*. The PAM sequence is underlined. | DNA | TTCGATAAAGCCGCCAATTGCTTC |
| 16 | Rhg1_TS3 (Target site 3 within the Rhg1 locus) from *Glycine max*. The PAM sequence is underlined. | DNA | TTCAGTGCTTCCTTCTTCGGCTTC |
| 18 | sgRNA_TS1. Targets the Rhg1_TS1 site. The tracrRNA sequence (underlined) is fused to the crRNA sequence via a pentaloop (italics). The crRNA comprises a repeat sequence (double underlined) and a spacer sequence (shown in bold). | DNA | GATTACATCTGGCGCGTTTATTCC ATTACTTTGGAGCCAGTCCCAGCG ACTATGTCGTATGGACGAAGCGCT TATTTATCGGAGAGAAAACCGATA AGTAAAACGCATCAAAGGAATTT GCGGGTTTTGGATTtttttttt |
| 19 | sgRNA_TS2. Targets the Rhg1_TS2 site. The tracrRNA sequence (underlined) is fused to the crRNA sequence via a pentaloop (italics). The crRNA comprises a repeat sequence (double underlined) and a spacer sequence (shown in bold). | DNA | GATTACATCTGGCGCGTTTATTCC ATTACTTTGGAGCCAGTCCCAGCG ACTATGTCGTATGGACGAAGCGCT TATTTATCGGAGAGAAAACCGATA AGTAAAACGCATCAAAGATAAAG CCGCCAATTGCTTCtttttttt |
| 20 | sgRNA_TS3. Targets the Rhg1_TS3 site. The tracrRNA sequence (underlined) is fused to the crRNA sequence via a pentaloop (italics). The crRNA comprises a repeat sequence (double underlined) and a spacer sequence (shown in bold). | DNA | GATTACATCTGGCGCGTTTATTCC ATTACTTTGGAGCCAGTCCCAGCG ACTATGTCGTATGGACGAAGCGCT TATTTATCGGAGAGAAAACCGATA AGTAAAACGCATCAAAGGTGCTT CCTTCTTCGGCTTCtttttttt |

TABLE 1-continued

Annotated sequences of the target sites and guide RNAs.

| SEQ ID NO: | Description | Nucleic acid or protein | Sequence |
|---|---|---|---|
| 47 | Rp1-TS1 (Target site 1 within the Rp1_locus) from *Zea mays*. The PAM sequence is underlined. | DNA | <u>TTCCC</u>ACAACCACATCACTTCCCA |
| 48 | Rp1-TS2 (Target site 1 within the Rp1_locus) from *Zea mays*. The PAM sequence is underlined. | DNA | <u>TTCTG</u>AATTGCCTACATCATTATG |
| 49 | Rp1-TS3 (Target site 1 within the Rp1_locus) from *Zea mays*. The PAM sequence is underlined. | DNA | <u>TTCCC</u>AACATTGGCAAGCTTACTT |
| 51 | sgRNA_TS4. Targets the Rp1_TS1 site. The tracrRNA sequence (underlined) is fused to the crRNA sequence via a pentaloop (italics). The crRNA comprises a repeat sequence (double underlined) and a spacer sequence (shown in bold). | DNA | GATTACATCTGGCGCGTTTATTCC ATTACTTTGGAGCCAGTCCCAGCG ACTATGTCGTATGGACGAAGCGCT TATTTATCGGAGA*GAAAA*CCGATA AGTAAAACGCATCAAAGCACAAC CACATCACTTCCCAtttttttt |
| 52 | sgRNA_TS5. Targets the Rp1_TS2 site. The tracrRNA sequence (underlined) is fused to the crRNA sequence (double underlined) via a pentaloop (italics). The crRNA comprises a repeat sequence (double underlined) and a spacer sequence (shown in bold). | DNA | GATTACATCTGGCGCGTTTATTCC ATTACTTTGGAGCCAGTCCCAGCG ACTATGTCGTATGGACGAAGCGCT TATTTATCGGAGA*GAAAA*CCGATA AGTAAAACGCATCAAAGGAATTG CCTACATCATTATGtttttttt |
| 53 | sgRNA_TS6. Targets the Rp1_TS3 site. The tracrRNA sequence (underlined) is fused to the crRNA sequence via a pentaloop (italics). The crRNA comprises a repeat sequence (double underlined) and a spacer sequence (shown in bold). | DNA | GATTACATCTGGCGCGTTTATTCC ATTACTTTGGAGCCAGTCCCAGCG ACTATGTCGTATGGACGAAGCGCT TATTTATCGGAGA*GAAAA*CCGATA AGTAAAACGCATCAAAGCAACAT TGGCAAGCTTACTTtttttttt |

Construct and Design of Single-Guide RNA Constructs:

CasX is a dual-RNA guided nuclease and requires a CRISPR RNA (crRNA) and trans-activating CRISPR RNA (tracrRNA) for RNA-guided DNA cleavage. For this experiment, the tracrRNA was fused with the crRNA using a pentaloop (GAAAA) to form a single-guide RNA (sgRNA). Three sgRNA constructs were designed to guide the CasX protein to the three selected target sites within Rhg1. Each sgRNA construct comprised the tracrRNA sequence, the pentaloop sequence and the crRNA sequence. The crRNA sequence further comprised a repeat sequence and a variable spacer sequence. All guide RNA sequences were operably linked to the Soy U6 promoter cassette (SEQ ID NO:17) and a polyT$_8$ terminator sequence. sgRNA_TS1 (SEQ ID NO. 18) was designed to guide the CasX protein to the Rhg1_TS1 site. sgRNA_TS2 (SEQ ID NO. 19) was designed to guide the CasX protein to the Rhg1_TS2 site. sgRNA_TS3 (SEQ ID NO. 20) was designed to guide the CasX protein to the Rhg1_TS3 site (See Table 1).

A short, double-stranded, blunt-ended DNA donor-oligonucleotide (SEQ ID NO: 21) was designed to test integration of donor DNA into the double-stranded breaks created by the engineered DsCasX_Gm at the target-sites.

Design of a Positive Control for the Oligo-into-Chromosome (OinC) Assay:

The Cas9 CRISPR-Cas nuclease system was used as a positive control. Two plant expression vectors were created for this purpose. The first was a T-DNA vector comprising a cassette comprising a soy codon-optimized Cas9 gene under the control of a Dahlia Mosaic virus promoter cassette. The vector also comprised a cassette for the aadA marker gene. The second vector comprised an expression cassette for sgRNA_TS4, a single-guide RNA designed to guide a Cas9 nuclease to a target site within the soy Rps1 (Resistance to *Phytophtora sojae* 1) gene locus (see Gao and Bhattacharyya, 2008, *BMC Plant Biol.*, 8:29).

Protoplast Transformation for Oligo-into-Chromosome Assay:

This assay tested the integration of the double-stranded oligonucleotide donor molecule into a double stranded break (DSB) generated by the DsCasX_Gm protein at the chosen target sites in the soy genome. The engineered nuclease and guide-RNA expression vectors were co-delivered into soy protoplasts (A3555 germplasm) together with the dsDNA donor oligonucleotide using standard polyethylene glycol (PEG) mediated transformation. For quantifying transformation frequency, a vector comprising a GFP expression cassette was also co-delivered. Briefly, approximately 3.2× $10^5$ protoplasts were transformed using PEG with 0.8 pmol of the DsCasX_Gm vector, 1.6 pmol of the single-guide RNA vector, 1 pmol of the GFP vector and 50 pmol of the dsDNA donor oligonucleotide. Protoplast samples transformed with the dsDNA fragment but lacking either the sgRNA vector or nuclease vector, were used as negative controls. The experimental design is described in Table 2. Each assay was performed in triplicate. Following transformation, the protoplasts were incubated in the dark in incubation buffer (0.6 M mannitol, 4 mM MES (pH5.7), 2 mM KCL) and harvested after 48 hours. Genomic DNA was isolated and assayed for integration of the dsDNA donor oligo fragment.

Testing for Oligo Integration:

Integration of the dsDNA fragment into the genomic DNA was detected using standard PCR and agarose gel electrophoresis to assess PCR amplicons. The dsDNA fragment may have integrated in either a 5' or 3' orientation with respect to the 5'- and 3'-ends of the DSB. Therefore, two PCR experiments were performed for each target site where the primer sets contained a primer specific to the dsDNA oligo fragment (SEQ ID NO:22), and a primer specific to either the 5' side or the 3' side of the DSB. The primer pairs (SEQ ID NO:22-28) used for each assay are described in Table 2.

The PCR amplicons were separated using standard agarose gel electrophoresis, and the size of each amplicon was confirmed by comparison to a molecular weight marker. As shown in Table 2, a band of the expected size was detected for the positive control (Table 2, Assay number 1) indicating efficient site-directed integration of oligo at the Rps1 target site following Cas9-mediated dsDNA cleavage. A band of expected size was also observed at the Rhg1-TS3 target region (Table 2, Assay number 4) indicating site-directed integration of the donor oligo at the Rhg1-TS3 site following DsCasX_Gm-mediated dsDNA cleavage. DNA samples from protoplasts transformed with the negative controls lacked PCR amplicons (Table 2, Assay numbers 5-10).

To further confirm oligo integration, the gel separated PCR amplicons were isolated, cloned via Zero blunt-end Topo cloning (Life Technologies), sequenced and compared to the reference sequence (SEQ ID NO:29). As shown in FIG. 1, an integration event (SEQ ID NO:30) was identified where the donor oligonucleotide integrated within the Rhg1_TS3 locus at a locus downstream of the PAM site, thereby confirming site-specific integration of the dsDNA donor oligo fragment at the Rhg1_TS3 locus. The results presented here demonstrate that the CasX nuclease can be optimized for expression in eukaryotic cells and can be reprogrammed to function as an RNA-guided endonuclease that promotes cleavage at a selected locus within a eukaryotic genome.

TABLE 2

Experimental design of the DsCasX_Gm mediated Oligo-into-Chromosome assay

| Assay Number | Assay | Nuclease | Target site | sg RNA | Donor oligonucleotide | Primers used (in conjunction with primer TM2R) | Expected band amplified? |
|---|---|---|---|---|---|---|---|
| 1 | Positive Control | Cas9 | Rps1 | sgRNA_TS4 | + | EN1866, EN1871 | Yes |
| 2 | Test 1 | DsCasX_Gm | Rhg1_TS1 | sgRNA_TS1 | + | EN2410, EN2411 | No |
| 3 | Test 2 | DsCasX_Gm | Rhg1_TS2 | sgRNA_TS2 | + | EN2410, EN2411 | No |
| 4 | Test 3 | DsCasX_Gm | Rhg1_TS3 | sgRNA_TS3 | + | EN2412, EN2413 | Yes |
| 5 | Negative Control 1 | – | Rps1 | sgRNA_TS4 | + | EN1866, EN1871 | No |
| 6 | Negative Control 2 | – | Rhg1_TS1 | sgRNA_TS1 | + | EN2410, EN2411 | No |
| 7 | Negative Control 3 | – | Rhg1_TS2 | sgRNA_TS2 | + | EN2410, EN2411 | No |
| 8 | Negative Control 4 | – | Rhg1_TS3 | sgRNA_TS3 | + | EN2412, EN2413 | No |
| 9 | Negative Control 5 | Cas9 | Rps1 | sgRNA_TS4 | – | EN1866, EN1871 | No |
| 10 | Negative Control 6 | DsCasX_Gm | Rhg_TS3 | sgRNA_TS3 | – | EN2412, EN2413 | No |

Example 2. Quantification of DsCasX_Gm Mediated Genome Edits by Targeted Deep Sequencing The mutation efficiency of DsCasX_Gm was measured by targeted deep sequencing of amplicons derived from soy genomic DNA treated with the CasX nuclease. The amplicons were generated from genomic DNA extracted from select samples from the OinC assay described in Example 1. The chosen samples are shown in Table 3.

The test samples were protoplasts transformed with expression vectors encoding the DsCasX_Gm engineered nuclease, the sgRNAs targeting either Soy Rhg1_TS1, Rhg1_TS2 or Rhg1_TS3 target site, the dsDNA donor oligonucleotide and the GFP vector (Table 3, Test samples). The control samples were protoplasts that were transformed with the sgRNA, the dsDNA donor oligonucleotide and the GFP vector but not DsCasX_Gm nuclease (Table 3, Control). As noted in Example 1, each assay was performed in triplicate. Forty-eight hours post transformation, GFP expression was analyzed using the Operetta High-Content Imaging System (PerkinElmer). Transformation frequencies (TFs) were calculated by dividing GFP positive cell counts by total cell counts. The isolated genomic DNA was assessed for mutations via targeted deep sequencing of amplicons spanning the target sites.

TABLE 3

Targeted deep sequencing assay to determine mutation rates induced by DsCasX_Gm

| Target site | Corresponding assay number from Table 2 | Assay type | DsCasX_Gm | sg RNA | Donor oligonucleotide | SEQ ID NOs of Primers used to generate amplicons |
|---|---|---|---|---|---|---|
| Rhg1_TS1 | 2 | Test | + | sgRNA_TS1 | + | 31 and 32 |
|  | 6 | Control | − | sgRNA_TS1 | + | 31 and 32 |
| Rhg1_TS2 | 3 | Test | + | sgRNA_TS2 | + | 33 and 34 |
|  | 7 | Control | − | sgRNA_TS2 | + | 33 and 34 |
| Rhg1_TS3 | 4 | Test | + | sgRNA_TS3 | + | 35 and 36 |
|  | 8 | Control | − | sgRNA_TS3 | + | 35 and 36 |

Amplicon Generation and Sample Processing for Deep Sequencing:

Samples were processed using a two-step PCR process. Genomic DNA was used as a template to PCR amplify a DNA fragment containing the target site using unique primers flanking the target site and having overhangs complementary to the Illumina sequencing adapters. Primers of SEQ ID NOs: 31 and 32 were used to amplify the Rhg1_TS1 site, primers of SEQ ID NOs: 33 and 34 were used to amplify Rhg1_TS2 site, and primers of SEQ ID NOs:35 and 36 were used to amplify the Rhg1_TS3 site. The PCR products were cleaned using SeqPure PCR purification kit (BioChain) and used as a template for a second round of PCR to add Illumina barcoded adapters (SEQ ID NO:33 and 34). The PCR products were cleaned using SeqPure PCR purification kit (BioChain). The quality of the DNA was confirmed using High Sensitivity DNA analysis (Agilent), quantified using PicoGreen (ThermoFisher Scientific) and sequenced on an Illumina 2X300 MiSeq platform using the manufacturers recommended procedure.

Sequenced Data Analysis:

After obtaining the raw reads, Trimmomatic (Version 0.36) (see Bolger et. al., 2014, *Bioinformatics*, 30:2114-2120) was used to trim adaptors and filter out low quality reads. CRISPResso tool (see Pinello et al, 2016, *Nature Bitechnology.* 34: 695-697) was used to merge paired-end reads and map the reads to amplicon sequences. However, CRISPResso was developed to call edits for Cas9-mediated genome editing and was not suitable for determining CasX-mediated edits. Therefore, a customized Python script was developed to identify CasX-mediated edits. This script was used to align the reads to reference amplicon sequences and compare alignment to identify substitutions, insertions, and deletions. In most targeted mutagenesis studies described in the art, the point mutations observed at the target site were predominantly deletions. Similarly, targeted deletions were expected to be the predominant form of mutations for CasX in this study too. The target genes in these experiments in soy and also in corn as shown below have multiple copies. Some of these copies have sequence variations in or around the target sites. These natural sequence variants were only substitutions, not insertions or deletions within the amplicon sequenced. To avoid potential confusion coming from these sequence variations, we ignored all substitutions and counted only deletions when considering targeted point mutations. Targeted deletion rates were normalized by transformation frequencies and calculated using the formula:

$$D\% = 100*(D/(T*TF)),$$

where D % is the percent of targeted deletions within each target site, D is the count of reads with deletions in the target site of interest, T is the total read count, TF is the transformation frequency.

As shown in FIG. 2, the percentage of targeted deletions observed within the Rhg1_TS3 amplicons in the DsCasX_Gm treated samples was significantly higher than the background rates observed in nuclease-free samples. This confirms that DsCasX_Gm can successfully induce cleavage and subsequent edits at a targeted locus within the soy genome.

Example 3. Engineering DsCasX to Promote Targeted Genome Editing in Corn

After confirming that CasX can be reprogrammed as a functional site-specific nuclease in eukaryotic cells, specifically soy, an assay was carried out to test its functionality in corn cells. The experimental details are described below.

Construction and Design of a Plant Vector for the Expression of Codon-Optimized Cas X Protein in *Zea mays* (Corn):

The nucleotide sequence of Deltaproteobacteria CasX (SEQ ID NO:2) was analyzed, and the open reading frame was codon-optimized for optimal expression in corn. The codon optimized variant, referred to as DsCasX_Zm (SEQ ID NO:39), was introduced into a plant expression vector. The T-DNA vector comprises two expression cassettes between left border (LB) and right border (RB) sequences. The first expression cassette (SEQ ID NO: 41) comprised the DsCasX_Zm open reading frame operably linked to a Dahlia Mosaic virus promoter cassette (SEQ ID NO: 42, which comprises SEQ ID NOs: 7, 8, and 43) and a transcription terminator (SEQ ID NO: 40). The DsCasX_Zm cassette (SEQ ID NO: 44) comprises N- and C-terminal nuclear localization signals (SEQ ID NO: 10) and an intron (SEQ ID NO: 12) that divides the DsCasX_Zm open reading frame into a 5'-portion (SEQ ID NO: 45) and 3'-portion (SEQ ID NO: 46).

The second expression cassette was a selectable marker cassette that provides resistance against the herbicide glyphosate.

Selection of Target Sites in the Corn Genome:

Four Rp1 gene paralogs in the corn LH244 germplasm were chosen as the target sites for gene editing with DsCasX_Zm. Rp1 genes provide resistance to rust (see Smith et al., 2004, *Genetics*, 167:1939-1947). Rp1_TS1 (SEQ ID NO: 47) and Rp1_TS2 (SEQ ID NO: 48) are located within the exon sequences of one paralog. Rp1_TS3 (SEQ ID NO: 49) is located within the exon of a second paralog. All three target sites contained the 5'-TTCN-3' PAM sequence at the 5' end of the target site (See Table 1).

Construct and Design of Single-Guide RNA Constructs:

Three sgRNA constructs were designed to guide the DsCasX_Zm protein to the three selected target sites within the Rp1 loci. Each sgRNA construct comprised the tracrRNA sequence, the pentaloop sequence and the crRNA sequence. The crRNA sequence comprised a repeat sequence and a variable spacer sequence. All guide RNA sequences were operably linked to the Corn U6 promoter cassette (SEQ ID NO: 50) and a polyT$_7$ terminator sequence. sgRNA_TS4 (SEQ ID NO: 51) was designed to guide the CasX protein to the Rp1_TS1 site. sgRNA_TS5 (SEQ ID NO: 52) was designed to guide the CasX protein to the Rp1_TS2 site. sgRNA_TS6 (SEQ ID NO: 53) was designed to guide the CasX protein to the Rp1_TS3 site (See Table 1).

Protoplast Transformation:

Expression vector encoding the DsCasX_Zm engineered nuclease and the corresponding sgRNAs along with a dsDNA donor oligonucleotide (SEQ ID NO:21) were transformed into corn LH244 protoplasts using standard polyethylene glycol (PEG) mediated transformation (see Table 4, Test samples). For quantifying transformation frequency, a vector containing a GFP expression cassette was also co-delivered. As controls, protoplasts were transformed with the sgRNA, donor oligonucleotide and the GFP vector, but not the DsCasX_Zm nuclease (Table 4, Control samples). Each assay was performed in triplicate. Following transformation, the protoplasts were incubated in the dark in incubation buffer and harvested after 48 hours. Transformation efficiency was calculated by quantifying GFP expression as described in Example 2. Genomic DNA was isolated and assessed for oligo integration and targeted mutations.

Assessing Target Site Mutations Via Deep Sequencing:

Samples were processed using a two-step PCR process as described in Example 2. Genomic DNA was used as a template to PCR amplify a DNA fragment containing the target site. Primers of SEQ ID NOs: 54 and 55 were used to amplify the Rp1_TS1 site, primers of SEQ ID NOs: 56 and 57 were used to amplify Rp1_TS2 site, and primers of SEQ ID NOs: 58 and 59 were used to amplify the Rp1_TS3 site. The PCR products were cleaned and used as a template for a second round of PCR to add Illumina barcoded adapters (SEQ ID NOs: 33 and 34). The PCR products were cleaned, quality-checked, quantified and sequenced on an Illumina 2X300 MiSeq platform.

Figure 3:
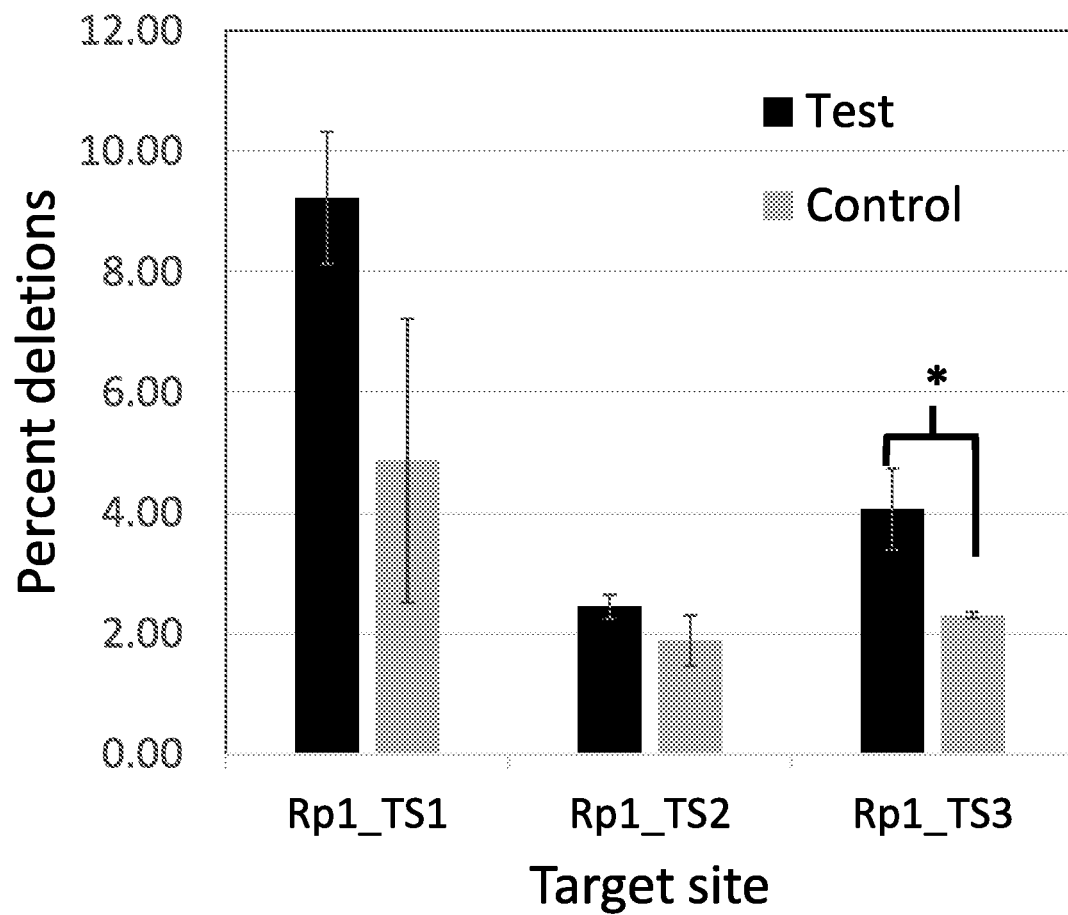
FIG. 3 shows the percentage of targeted deletions induced by DsCasX_Zm at three target sites within the Rp1 locus in corn as determined by targeted deep sequencing. Test samples were treated with DsCasX_Zm nuclease while the Control samples lacked DsCasX_Zm. Data are represented as the mean of three biological replicates. Error bars represent one standard deviation. Statistical significance was determined using a Student's T-test, and * indicates P<0.05.

As described in Example 2, after obtaining the raw reads, Trimmomatic was used to trim adaptors and filter out low quality reads. CRISPResso tool was used to merge paired-end reads and map the reads to amplicon sequences. A customized Python script was used to align the reads to a reference amplicon and analyze edits. Only deletions were used to calculate mutation rates. As described in Example 2, the data were normalized for transformation frequency and used to determine mutation rates at each of the target sites. As shown in FIG. 3, the percentage of targeted deletions observed within the Rp1_TS3 amplicons in the DsCasX_Zm treated samples was significantly higher than the background rates observed in the nuclease-free samples. This confirms that the engineered DsCasX_Zm can successfully induce cleavage at a selected locus within the corn genome.

Example 4. Engineering PsCasX to Promote Targeted Genome Editing in Corn

The CasX protein was identified in two organisms belonging to two different phyla—Deltaproteobacteria and Planctomycete. There is 68% protein sequence identity between the CasX proteins from these two phyla. Furthermore, the CRISPR arrays associated with each CasX have highly similar repeats, spacers, and tracrRNAs. Burstein et. al. have shown that the CasX protein from Planctomycete species (PsCasX) (SEQ ID NO: 60) is also a functional DNA targeting, RNA-guided CRISPR-associated protein in pro-

TABLE 4

Targeted deep sequencing to determine mutation rates induced by DsCasX_Zm.

| Target site | Assay | DsCasX_Zm | sg RNA | Donor oligonucleotide | SEQ ID NOs of Primers used to generate amplicons |
|---|---|---|---|---|---|
| Rp1_TS1 | Test | + | sgRNA_TS4 | + | 54 and 55 |
|  | Control | − | sgRNA_TS4 | + | 54 and 55 |
| Rp1_TS2 | Test | + | sgRNA_TS5 | + | 56 and 57 |
|  | Control | − | sgRNA_TS5 | + | 56 and 57 |
| Rp1_TS3 | Test | + | sgRNA_TS6 | + | 58 and 59 |
|  | Control | − | sgRNA_TS6 | + | 58 and 59 |

Testing for Oligo Integration:

The extracted genomic DNA was tested for integration of the dsDNA donor oligo fragment in the target sites via flank PCR assays similar to the process described in Example 1. Two PCR reactions were run for each target site and each primer set contained a primer specific to the dsDNA oligo fragment and a primer specific to either the 5' side or the 3' side of the target site. The PCR amplicons were separated using standard agarose gel electrophoresis. PCR bands of the expected size were not detected.

karyotic systems. However, it was unknown if the PsCasX protein is functional in eukaryotic systems. An experiment was performed to determine if the PsCasX protein could function as a programmable RNA-guided endonuclease in eukaryotic cells, specifically in corn (*Zea mays*). The experimental details are described below.

Construction and Design of a Plant Vector for the Expression of Codon-Optimized PsCasX Protein in *Zea mays* (Corn):

The nucleotide sequence of Planctomycete CasX disclosed by Burstein et al. (SEQ ID NO: 61) was analyzed and the open reading frame was codon-optimized for optimal expression in corn. The codon optimized variant, referred to as PsCasX_Zm (SEQ ID NO: 62), was introduced into a plant expression vector. The T-DNA vector comprises two expression cassettes between left border (LB) and right border (RB) sequences. The first expression cassette (SEQ ID NO:63) comprises the PsCasX_Zm open reading frame operably linked to a Dahlia Mosaic virus promoter cassette (SEQ ID NO: 42, which comprises SEQ ID NOs: 7, 8, and 43) and a transcription terminator (SEQ ID NO: 40). The PsCasX_Zm cassette (SEQ ID NO: 64) further comprises N- and C-terminal nuclear localization signals (SEQ ID NO: 10) and an intron (SEQ ID NO: 12) that divide the PsCasX_Zm open reading frame into a 5'-portion (SEQ ID NO: 65) and 3'-portion (SEQ ID NO: 66).

The second expression cassette was a selectable marker cassette that provides resistance against the herbicide glyphosate.

Selection of Target Sites and Design of Guide RNAs:

The target sites and guide RNAs are essentially those described in Example 3. Briefly, the chosen target sites were Rp1_TS1 (SEQ ID NO:47), Rp1_TS2 (SEQ ID NO: 48) and Rp1_TS3 (SEQ ID NO: 49) (see Table 1). The corresponding guide RNAs were sgRNA_TS4 (SEQ ID NO: 51), designed to target the Rp1_TS1 site; sgRNA_TS5, (SEQ ID NO: 52) designed to target the Rp1_TS2 site; and sgRNA_TS6 (SEQ ID NO: 53), designed to target the Rp1_TS3 site (see Table 1).

Protoplast Transformation:

Expression vectors encoding the PsCasX_Zm engineered nuclease and the corresponding sgRNAs along with the dsDNA donor oligonucleotide were transformed into corn LH244 protoplasts using standard polyethylene glycol (PEG) mediated transformation (see Table 5, Test samples). For quantifying transformation frequency, a vector containing a GFP expression cassette was co-delivered. As controls, protoplasts were transformed with the sgRNA, donor oligonucleotide and the GFP vector, but not the PsCasX_Zm nuclease (see Table 5, Control samples). Each assay was performed in triplicate. Following transformation, the protoplasts were incubated in the dark in incubation buffer and harvested after 48 hours. Transformation efficiency was calculated by quantifying GFP expression. Genomic DNA was isolated and assessed for oligo integration as well as target site mutations.

Testing for Oligo Integration:

The extracted genomic DNA was tested for integration of the dsDNA donor oligo fragment in the target sites via flank PCR assays similar to the process described in Example 1. Two PCR reactions were run for each target site and each primer set contained a primer specific to the dsDNA oligo fragment and a primer specific to either the 5' side or the 3' side of the target site. The PCR amplicons were separated using standard agarose gel electrophoresis. PCR amplicons of the expected size were not detected.

Assessing Target Site Mutations Via Deep Sequencing:

Samples were processed using a two-step PCR process as described in Example 2. Genomic DNA was used to PCR amplify a DNA fragment containing the target site using unique primers. The primer pairs used for the three target sites were the same as those used for DsCasX_Zm experiment and described in Example 3. Following a second round of PCR to add Illumina barcoded adapters, the PCR products were cleaned, quality-checked, quantified and sequenced on an Illumina 2X300 MiSeq platform.

Figure 4:
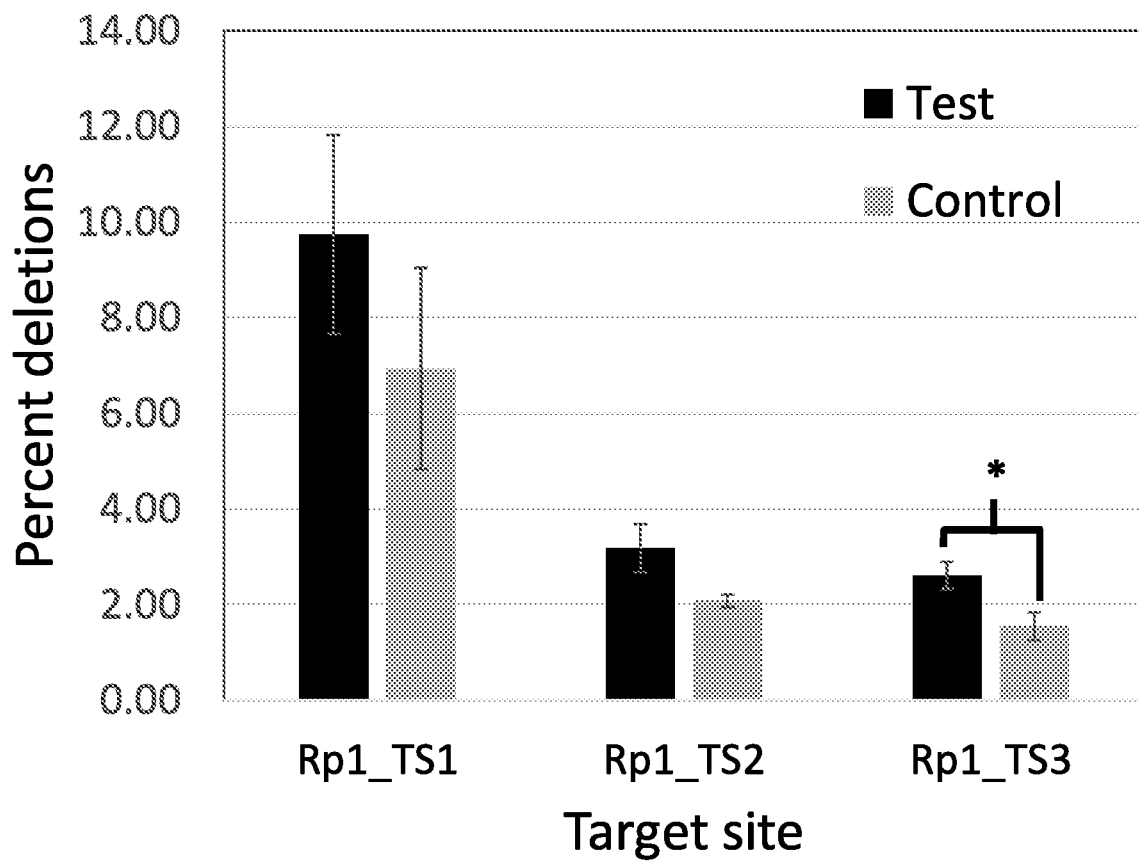
FIG. 4 shows the percentage of targeted deletions induced by PsCasX_Zm at three target sites within the Rp1 locus in corn as determined by targeted deep sequencing. Test samples were treated with PsCasX_Zm nuclease while the Control samples lacked PsCasX_Zm. Data are represented as the mean of three biological replicates. Error bars represent one standard deviation. Statistical significance was determined using a Student's T-test, and * indicates P<0.05.

As described in Example 2, after obtaining the raw reads, Trimmomatic was used to trim adaptors and filter out low quality reads. CRISPResso tool was used to merge paired-end reads and map the reads to amplicon sequences. A customized Python script was used to align the reads to a reference amplicon and analyze the reads to identify PsCasX mediated edits. Only deletions were used to calculate mutation rates. The data were normalized for transformation frequency as described in Example 2 and the normalized data used to determine mutation rates at each of the target sites. As shown in FIG. 4, the percentage of targeted deletions observed within the Rp1_TS3 amplicons in the PsCasX_Zm treated samples was significantly higher than the background rates observed in the nuclease-free samples. This confirms that the engineered PsCasX_Zm can successfully induce cleavage at a selected locus within the corn genome.

TABLE 5

Targeted deep sequencing to determine mutation rates induced by PsCasX_Zm.

| Target site | Assay | PsDasX_Gm | sg RNA | Donor oligonucleotide | SEQ ID NOs of Primers used to generate amplicons |
|---|---|---|---|---|---|
| Rp1_TS1 | Test | + | sgRNA_TS4 | + | 54 and 55 |
|  | Control | − | sgRNA_TS4 | + | 54 and 55 |
| Rp1_TS2 | Test | + | sgRNA_TS5 | + | 56 and 57 |
|  | Control | − | sgRNA_TS5 | + | 56 and 57 |
| Rp1_TS3 | Test | + | sgRNA_TS6 | + | 58 and 59 |
|  | Control | − | sgRNA_TS6 | + | 58 and 59 |

Example 5. Analysis of Query Sequence within Amplicons Generated from Deep Sequencing Assays The deep sequencing analysis described in Examples 2-4 took the entire 20 bp region downstream of PAM into consideration while identifying deletions. A second analysis was carried out where the search for deletions was narrowed down to a query region spanning 18 to 24 bps downstream of the PAM site for assaying deletions induced following targeted cleavage by CasX. Only deletions that were 2 bp and larger were considered for the second analysis.

Figure 5:
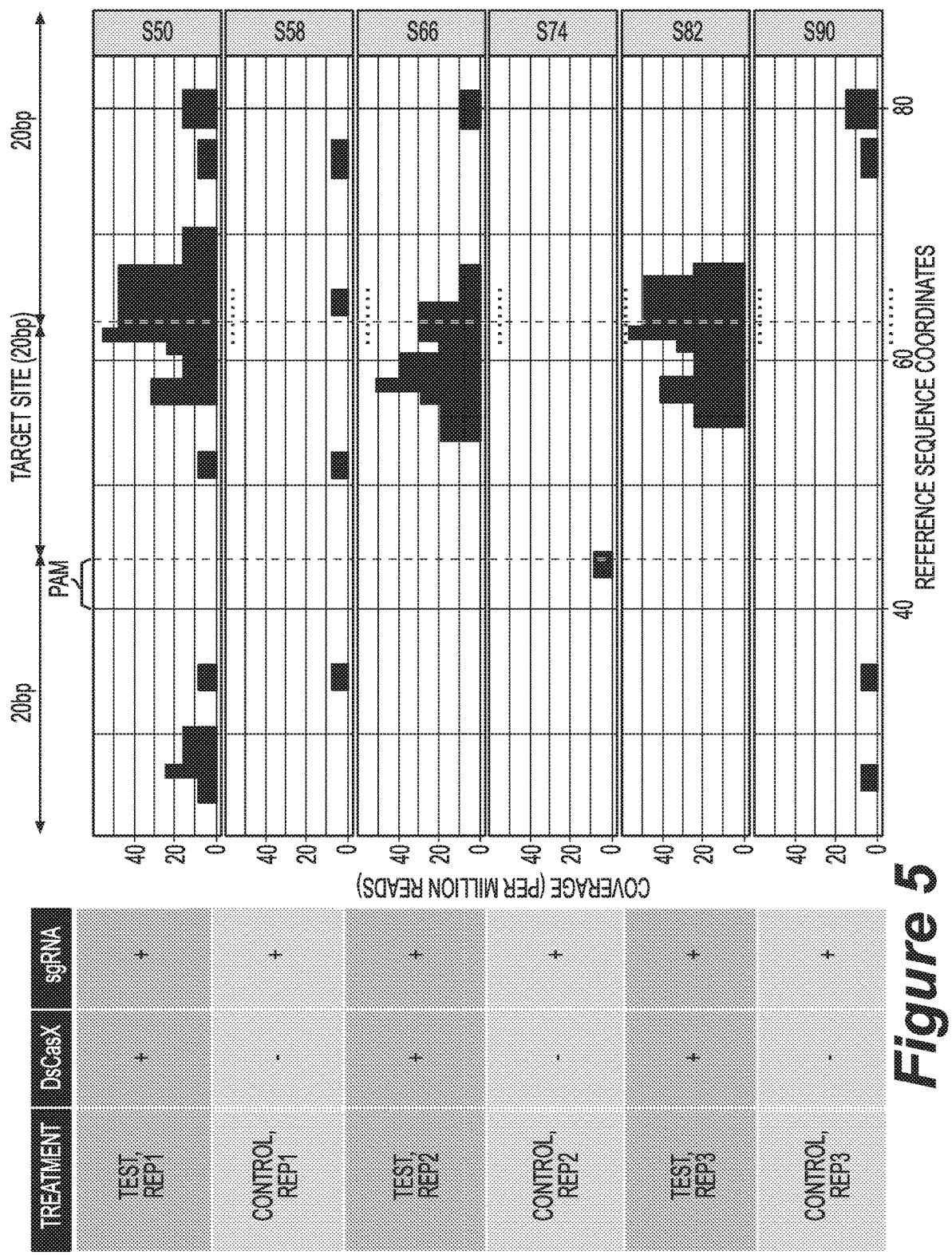
FIG. 5 shows occurrence of deletions at each base-pair within a 60 bp region in soy Rhg1_TS1 amplicons. In each test treatment, deletions accumulated around the Query Sequence (18 bp-24 bp downstream of PAM) while these mutations were largely absent in the negative controls lacking the DsCasX enzyme. Dotted lines beneath each graph represent the Query Sequence.

Validating the query region: Prior to initiating the second analysis, the query region was validated. The sample data set used for validation comprised the amplicons generated from deep sequencing assays investigating the activity of DsCasX_Gm in soy. The generation of the amplicons is described in Example 2. The test assay comprised soy protoplasts treated with DsCasX_Gm and sgRNA targeting Rhg_TS1 site (Table 3, Assay 2). The control assay comprised treatments lacking the nuclease (Table 3, Assay 6). Within each amplicon, a 60 bp region comprising the 20 bp CasX Rhg1_TS1 sequence downstream of the PAM site and 20 bps upstream and downstream of this site was chosen for analysis (nucleotide positions 24 to 83 in SEQ ID NO: 67). The deletion rate at every base-pair within this ~60 bp region was scored. As shown in FIG. 5, in the three technical replicates representing the test samples, mutations clustered at and around the query region spanning 18 to 24 bp downstream of the PAM site. Amplicons from the control assays did not harbor similar rates of mutations and did not cluster around the query site.

Results from the Second Analysis:

The second sequence analysis was applied to amplicons generated from assays described in Examples 2, 3, and 4. Briefly, Example 2 describes generation of amplicons from test and control assays investigating the DsCasX_Gm nuclease activity on the three Rhg1 target sites in soy genome. Example 3 describes generation of amplicons from test and control assays investigating the DsCasX_Zm nuclease activity on the three Rp1 target sites in corn genome. Example 4 describes generation of amplicons from test and control assays investigating the PsCasX_Zm nuclease activity on the three Rp1 target sites in corn. Based on the new analysis criteria, targeted deletions were detected at all three soy Rhg1 query sequences from amplicons generated from test samples in Example 2 (See FIG. 6). A total of 15 unique Rhg1_TS1 amplicons, 2 unique Rhg1_TS2 amplicons, and 4 unique Rhg1_TS3 amplicons with deletions meeting the selection criteria were identified in the test samples. No mutations matching the selection criteria were found in the negative controls. The mutant reads were low in number and unequally represented in biological replicates, which prevented quantification. Their presence in tests and absence in negative controls provided another qualitative confirmation of DsCasX-mediated targeted cleavage of soy chromosomes at Rhg_TS3 and de novo qualitative evidence for cleavage activity at the other two target sites Rhg1_TS1 and Rhg_TS2 (FIG. 6).

The second sequence analysis failed to identify sequences meeting the selection criteria in test and control assays generated from amplicons described in Examples 3 and 4. While some sequences at the corn Rp1_TS1 and Rp1_TS2 matched the analysis criteria, they were identical in both tests and negative controls, suggesting that they represented native paralogs of the target sites rather than de novo mutations. The Rp1 gene chosen for this experiment as a target site is known to have multiple variable paralogs in corn (Smith et al., 2004, *Genetics*, 167:1939-1947).

Example 6: Design of Additional Codon-Optimized CasX Sequences

The nucleotide sequence of Deltaproteobacteria CasX disclosed by Burstein et. al. (SEQ ID NO:2) (2017, *Nature*, 542:237-241) was modified through algorithmic methods, partly based on soy codon preference, to design DsCasX_Gm2 (SEQ ID NO:79). SEQ ID NO:2 was also modified through algorithmic means partly based on monocot codon preference to design DsCasX_M1 (SEQ ID NO: 80). The new codon optimized variants were introduced into expression cassettes in plant T-DNA expression vectors.

The DsCasX_Gm2 expression cassette comprised SEQ ID:79, lacking the terminal 3 nucleotides fused to a sequence encoding a plant NLS (SEQ ID NO: 81) at the 5' end and an NLS sequence from a tomato Heat shock transcription factor (SEQ ID NO: 82) at the 3' end followed by a 3 bp nucleotide sequence encoding a termination codon. The NLS-DsCasx_Gm2-NLS sequence was operably linked to an *Arabidopsis* Ubiquitin 3 promoter sequence (Gen Bank Accession ID: L05363.1) and a *Medicago truncatula* PSII terminator sequence (SEQ ID NO:83). The DsCasX_M1 expression cassette was essentially similar to that described above except that the DsCasX_Gm2 sequence was replaced by DsCasX_M1 sequence.

Example 7: Testing in Planta Cutting Activity of Codon-Optimized DsCasX Nuclease Sequences The in planta nuclease activities of the codon-optimized variants DsCasX_Gm, DsCasX_Gm2 and DsCasX_M1 are tested in soy. Expression vectors with encoding the codon-optimized CasX nucleases and gRNAs targeting a soy chromosomal regions Rhg1_TS1, Rhg1_TS2, Thg1_TS3 are transformed into soy embryos or explants using standard *Agrobacterium*-mediated transformation methods. Rates of mutagenesis at the target sites will be determined in R0 plants. For this, genomic DNA is subjected to a PCR reaction with primers flanking the target sites to generate amplicons. The amplicons fragment length is then compared to a wild type amplicon to identify mutants. PCR reactions are carried out using 5' FAM-labeled primer, a standard primer and Phusion™ polymerase (New England Biolabs, MA) according to the manufacturer's instructions to generate 200 to 500 bp PCR fragments. 0.5 ul PCR product is combined with 0.5 ul GeneScan 1200 LIZ Size Standard (Thermo Fisher, MA), 9 ul formamide and run on ABI sequencer (Thermo Fisher, MA). The FLA reactions are subsequently analyzed for fragment length variation to identify plants with mutations/indels at the target sites. Select mutants will be validated by Sanger sequencing.

The invention claimed is:

1. A method of modifying at least one target site in a soybean genome comprising:
   (a) providing a soybean cell with a first nucleic acid comprising SEQ ID NO: 3 and a nuclear localization signal, and
   (b) providing said soybean cell with a second nucleic acid comprising a guide RNA (gRNA) or encoding said gRNA,
   wherein said gRNA and said CasX nuclease encoded by SEQ ID NO: 3 form a complex,
   wherein said gRNA hybridizes to said target site, and
   wherein said complex generates a modification at said target site in the soybean genome.

2. The method of claim 1, wherein said gRNA is a single guide RNA (sgRNA).

3. The method of claim 1, wherein said method further comprises providing a donor nucleic acid to said soybean cell and said donor nucleic acid is inserted into said target site.

4. The method of claim 1, wherein said first nucleic acid and the second nucleic acid encoding a gRNA are provided in a single vector.

5. The method of claim 1, wherein said first nucleic acid and the second nucleic acid encoding a gRNA are provided in separate vectors.

6. A plant soybean cell comprising an engineered system comprising:
   (a) a first nucleic acid comprising SEQ ID NO:3 and a nuclear localization signal, and
   (b) a second nucleic acid comprising a guide RNA (gRNA) or encoding said gRNA,
   wherein said gRNA is designed to hybridize with a target site in said soybean cell.

7. The soybean cell of claim 6, wherein said gRNA is a sgRNA.

* * * * *

SEQUENCE LISTING

<160> NUMBER OF SEQ ID NOS: 88

<210> SEQ ID NO 1
<211> LENGTH: 986
<212> TYPE: PRT
<213> ORGANISM: Unknown
<220> FEATURE:
<223> OTHER INFORMATION: Deltaproteobacteria

<400> SEQUENCE: 1

Met Glu Lys Arg Ile Asn Lys Ile Arg Lys Lys Leu Ser Ala Asp Asn
1               5                   10                  15

Ala Thr Lys Pro Val Ser Arg Ser Gly Pro Met Lys Thr Leu Leu Val
            20                  25                  30

-continued

```
Arg Val Met Thr Asp Asp Leu Lys Lys Arg Leu Glu Lys Arg Arg Lys
         35                  40                  45

Lys Pro Glu Val Met Pro Gln Val Ile Ser Asn Asn Ala Ala Asn Asn
 50                  55                  60

Leu Arg Met Leu Leu Asp Asp Tyr Thr Lys Met Lys Glu Ala Ile Leu
 65                  70                  75                  80

Gln Val Tyr Trp Gln Glu Phe Lys Asp Asp His Val Gly Leu Met Cys
                 85                  90                  95

Lys Phe Ala Gln Pro Ala Ser Lys Lys Ile Asp Gln Asn Lys Leu Lys
                100                 105                 110

Pro Glu Met Asp Glu Lys Gly Asn Leu Thr Thr Ala Gly Phe Ala Cys
            115                 120                 125

Ser Gln Cys Gly Gln Pro Leu Phe Val Tyr Lys Leu Glu Gln Val Ser
130                 135                 140

Glu Lys Gly Lys Ala Tyr Thr Asn Tyr Phe Gly Arg Cys Asn Val Ala
145                 150                 155                 160

Glu His Glu Lys Leu Ile Leu Leu Ala Gln Leu Lys Pro Glu Lys Asp
                165                 170                 175

Ser Asp Glu Ala Val Thr Tyr Ser Leu Gly Lys Phe Gly Gln Arg Ala
            180                 185                 190

Leu Asp Phe Tyr Ser Ile His Val Thr Lys Glu Ser Thr His Pro Val
        195                 200                 205

Lys Pro Leu Ala Gln Ile Ala Gly Asn Arg Tyr Ala Ser Gly Pro Val
    210                 215                 220

Gly Lys Ala Leu Ser Asp Ala Cys Met Gly Thr Ile Ala Ser Phe Leu
225                 230                 235                 240

Ser Lys Tyr Gln Asp Ile Ile Glu His Gln Lys Val Val Lys Gly
                245                 250                 255

Asn Gln Lys Arg Leu Glu Ser Leu Arg Glu Leu Ala Gly Lys Glu Asn
            260                 265                 270

Leu Glu Tyr Pro Ser Val Thr Leu Pro Pro Gln Pro His Thr Lys Glu
        275                 280                 285

Gly Val Asp Ala Tyr Asn Glu Val Ile Ala Arg Val Arg Met Trp Val
    290                 295                 300

Asn Leu Asn Leu Trp Gln Lys Leu Lys Leu Ser Arg Asp Asp Ala Lys
305                 310                 315                 320

Pro Leu Leu Arg Leu Lys Gly Phe Pro Ser Phe Pro Val Val Glu Arg
                325                 330                 335

Arg Glu Asn Glu Val Asp Trp Trp Asn Thr Ile Asn Glu Val Lys Lys
            340                 345                 350

Leu Ile Asp Ala Lys Arg Asp Met Gly Arg Val Phe Trp Ser Gly Val
        355                 360                 365

Thr Ala Glu Lys Arg Asn Thr Ile Leu Glu Gly Tyr Asn Tyr Leu Pro
    370                 375                 380

Asn Glu Asn Asp His Lys Lys Arg Glu Gly Ser Leu Glu Asn Pro Lys
385                 390                 395                 400

Lys Pro Ala Lys Arg Gln Phe Gly Asp Leu Leu Leu Tyr Leu Glu Lys
                405                 410                 415

Lys Tyr Ala Gly Asp Trp Gly Lys Val Phe Asp Glu Ala Trp Glu Arg
            420                 425                 430

Ile Asp Lys Lys Ile Ala Gly Leu Thr Ser His Ile Glu Arg Glu Glu
        435                 440                 445
```

```
Ala Arg Asn Ala Glu Asp Ala Gln Ser Lys Ala Val Leu Thr Asp Trp
450                 455                 460

Leu Arg Ala Lys Ala Ser Phe Val Leu Glu Arg Leu Lys Glu Met Asp
465                 470                 475                 480

Glu Lys Glu Phe Tyr Ala Cys Glu Ile Gln Leu Gln Lys Trp Tyr Gly
                485                 490                 495

Asp Leu Arg Gly Asn Pro Phe Ala Val Glu Ala Glu Asn Arg Val Val
            500                 505                 510

Asp Ile Ser Gly Phe Ser Ile Gly Ser Asp Gly His Ser Ile Gln Tyr
        515                 520                 525

Arg Asn Leu Leu Ala Trp Lys Tyr Leu Glu Asn Gly Lys Arg Glu Phe
530                 535                 540

Tyr Leu Leu Met Asn Tyr Gly Lys Lys Gly Arg Ile Arg Phe Thr Asp
545                 550                 555                 560

Gly Thr Asp Ile Lys Lys Ser Gly Lys Trp Gln Gly Leu Leu Tyr Gly
                565                 570                 575

Gly Gly Lys Ala Lys Val Ile Asp Leu Thr Phe Asp Pro Asp Asp Glu
            580                 585                 590

Gln Leu Ile Ile Leu Pro Leu Ala Phe Gly Thr Arg Gln Gly Arg Glu
        595                 600                 605

Phe Ile Trp Asn Asp Leu Leu Ser Leu Glu Thr Gly Leu Ile Lys Leu
610                 615                 620

Ala Asn Gly Arg Val Ile Glu Lys Thr Ile Tyr Asn Lys Lys Ile Gly
625                 630                 635                 640

Arg Asp Glu Pro Ala Leu Phe Val Ala Leu Thr Phe Glu Arg Arg Glu
                645                 650                 655

Val Val Asp Pro Ser Asn Ile Lys Pro Val Asn Leu Ile Gly Val Asp
            660                 665                 670

Arg Gly Glu Asn Ile Pro Ala Val Ile Ala Leu Thr Asp Pro Glu Gly
        675                 680                 685

Cys Pro Leu Pro Glu Phe Lys Asp Ser Ser Gly Gly Pro Thr Asp Ile
690                 695                 700

Leu Arg Ile Gly Glu Gly Tyr Lys Glu Lys Gln Arg Ala Ile Gln Ala
705                 710                 715                 720

Ala Lys Glu Val Glu Gln Arg Ala Gly Gly Tyr Ser Arg Lys Phe
                725                 730                 735

Ala Ser Lys Ser Arg Asn Leu Ala Asp Asp Met Val Arg Asn Ser Ala
            740                 745                 750

Arg Asp Leu Phe Tyr His Ala Val Thr His Asp Ala Val Leu Val Phe
        755                 760                 765

Glu Asn Leu Ser Arg Gly Phe Gly Arg Gln Gly Lys Arg Thr Phe Met
770                 775                 780

Thr Glu Arg Gln Tyr Thr Lys Met Glu Asp Trp Leu Thr Ala Lys Leu
785                 790                 795                 800

Ala Tyr Glu Gly Leu Thr Ser Lys Thr Tyr Leu Ser Lys Thr Leu Ala
                805                 810                 815

Gln Tyr Thr Ser Lys Thr Cys Ser Asn Cys Gly Phe Thr Ile Thr Thr
            820                 825                 830

Ala Asp Tyr Asp Gly Met Leu Val Arg Leu Lys Lys Thr Ser Asp Gly
        835                 840                 845

Trp Ala Thr Thr Leu Asn Asn Lys Glu Leu Lys Ala Glu Gly Gln Ile
850                 855                 860
```

```
Thr Tyr Tyr Asn Arg Tyr Lys Arg Gln Thr Val Glu Lys Glu Leu Ser
865                 870                 875                 880

Ala Glu Leu Asp Arg Leu Ser Glu Glu Ser Gly Asn Asn Asp Ile Ser
                885                 890                 895

Lys Trp Thr Lys Gly Arg Arg Asp Glu Ala Leu Phe Leu Leu Lys Lys
            900                 905                 910

Arg Phe Ser His Arg Pro Val Gln Glu Gln Phe Val Cys Leu Asp Cys
        915                 920                 925

Gly His Glu Val His Ala Asp Glu Gln Ala Ala Leu Asn Ile Ala Arg
    930                 935                 940

Ser Trp Leu Phe Leu Asn Ser Asn Ser Thr Glu Phe Lys Ser Tyr Lys
945                 950                 955                 960

Ser Gly Lys Gln Pro Phe Val Gly Ala Trp Gln Ala Phe Tyr Lys Arg
                965                 970                 975

Arg Leu Lys Glu Val Trp Lys Pro Asn Ala
            980                 985

<210> SEQ ID NO 2
<211> LENGTH: 2961
<212> TYPE: DNA
<213> ORGANISM: Unknown
<220> FEATURE:
<223> OTHER INFORMATION: Deltaproteobacteria

<400> SEQUENCE: 2
atggaaaaac gcattaacaa aattcgcaaa aaactgagcg cggataacgc gaccaaaccg      60
gtgagccgca gcggcccgat gaaaaccctg ctggtgcgcg tgatgaccga tgatctgaaa     120
aaacgcctgg aaaaacgccg caaaaaaccg aagtgatgc cgcaggtgat tagcaacaac     180
gcggcgaaca acctgcgcat gctgctggat gattatacca aaatgaaaga agcgattctg     240
caggtgtatt ggcaggaatt taaagatgat catgtgggcc tgatgtgcaa atttgcgcag     300
ccggcgagca aaaaaattga tcagaacaaa ctgaaccgg aatggatga aaaaggcaac     360
ctgaccaccg cgggctttgc gtgcagccag tgcggccagc cgctgtttgt gtataaactg     420
gaacaggtga cgaaaaaagg caaagcgtat accaactatt ttggccgctg caacgtggcg     480
gaacatgaaa aactgattct gctggcgcag ctgaaaccgg aaaagatag cgatgaagcg     540
gtgacctata gcctgggcaa atttggccag cgcgcgctgg attttatag cattcatgtg     600
accaaagaaa gcacccatcc ggtgaaaccg ctggcgcaga ttgcgggcaa ccgctatgcg     660
agcggcccgg tggcaaagc gctgagcgat gcgtgcatgg gcaccattgc gagctttctg     720
agcaaatatc aggatattat tattgaacat cagaaagtgg tgaaaggcaa ccagaaacgc     780
ctggaaagcc tgcgcgaact ggcgggcaaa gaaaacctgg aatatccgag cgtgaccctg     840
ccgccgcagc cgcataccaa agaaggcgtg gatgcgtata cgaagtgat tgcgcgcgtg     900
cgcatgtggg tgaacctgaa cctgtggcag aaactgaaac tgagccgcga tgatgcgaaa     960
ccgctgctgc cgctgaaagg cttttccgagc tttccggtgg tgaacgcccg cgaaaacgaa    1020
gtggattggt ggaacaccat taacgaagtg aaaaaactga ttgatgcgaa acgcgatatg    1080
ggccgcgtgt ttggagcgg cgtgaccgcg gaaaaacgca caccattct ggaaggctat    1140
aactatctgc cgaacgaaaa cgatcataaa aaacgcgaag cagcctgga aacccgaaa    1200
aaaccggcga acgccagtt tggcgatctg ctgctgtatc tggaaaaaaa atatgcgggc    1260
gattgggca agtgtttga tgaagcgtgg gaacgcattg ataaaaaaat tgcgggcctg    1320
accagccata ttgaacgcga agaagcgcgc aacgcggaag atgcgcagag caaagcggtg    1380
```

```
ctgaccgatt ggctgcgcgc gaaagcgagc tttgtgctgg aacgcctgaa agaaatggat    1440
gaaaaagaat tttatgcgtg cgaaattcag ctgcagaaat ggtatggcga tctgcgcggc    1500
aacccgtttg cggtggaagc ggaaaaccgc gtggtggata ttagcggctt tagcattggc    1560
agcgatggcc atagcattca gtatcgcaac ctgctggcgt ggaaatatct ggaaaacggc    1620
aaacgcgaat tttatctgct gatgaactat ggcaaaaaag ccgcattcg ctttaccgat     1680 ggcaccgata ttaaaaaaag cggcaaatgg cagggcctgc tgtatggcgg cggcaaagcg    1740
aaagtgattg atctgacctt tgatccggat gatgaacagc tgattattct gccgctggcg    1800
tttggcaccc gccagggccg cgaatttatt tggaacgatc tgctgagcct ggaaaccggc    1860
ctgattaaac tggcgaacgg ccgcgtgatt gaaaaaacca tttataacaa aaaaattggc    1920
cgcgatgaac cggcgctgtt tgtggcgctg acctttgaac gccgcgaagt ggtggatccg    1980
agcaacatta accggtgaa cctgattggc gtggatcgcg gcgaaaacat tccggcggtg     2040
attgcgctga ccgatccgga aggctgcccg ctgccggaat ttaaagatag cagcggcggc    2100
ccgaccgata ttctgcgcat tggcgaaggc tataaagaaa acagcgcgc gattcaggcg     2160 gcgaaagaag tggaacagcg ccgcgcgggc ggctatagcc gcaaatttgc gagcaaaagc    2220
cgcaacctgg cggatgatat ggtgcgcaac agcgcgcgcg atctgtttta tcatgcggtg    2280
acccatgatg cggtgctggt gtttgaaaaa ctgagccgcg gctttggccg ccagggcaaa    2340
cgcaccttta tgaccgaacg ccagtatacc aaaatggaag attggctgac cgcgaaactg    2400
gcgtatgaag gcctgaccag caaaaccctat ctgagcaaaa ccctggcgca gtataccagc    2460
aaaacctgca gcaactgcgg ctttaccatt accaccgcgg attatgatgg catgctggtg    2520
cgcctgaaaa aaccagcga tggctgggcg accaccctga caacaaaga actgaaagcg     2580 gaaggccaga ttacctatta taccgctat aaacgccaga ccgtgaaaaa agaactgagc      2640
gcggaactgg atcgcctgag cgaagaaagc ggcaacaacg atattagcaa atggaccaaa    2700
ggccgccgcg atgaagcgct gtttctgctg aaaaaacgct ttagccatcg cccggtgcag    2760
gaacagtttg tgtgcctgga ttgcggccat gaagtgcatg cggatgaaca ggcggcgctg    2820
aacattgcgc gcagctggct gtttctgaac agcaacagca ccgaatttaa aagctataaa    2880
agcggcaaac agccgtttgt gggcgcgtgg caggcgtttt ataaacgccg cctgaaagaa    2940
gtgtggaaac cgaacgcgta a                                              2961
```

<210> SEQ ID NO 3
<211> LENGTH: 2961
<212> TYPE: DNA
<213> ORGANISM: Artificial
<220> FEATURE:
<223> OTHER INFORMATION: Synthetic polynucleotide. DsCasX_Gm
     (Deltaproteobacteria sp.CasX codon optimized for Soy)

<400> SEQUENCE: 3

```
atggagaaga ggattaacaa gattaggaag aaattatccg ctgataacgc aaccaaacca     60
gtttcccgaa gcggcccaat gaagactctg ctcgttagag tgatgacaga cgatcttaag    120
aaaagactcg agaagcgtag aaagaagccg gaggttatgc cccaggtgat ttctaataac    180
gcagcaaaca atcttcgaat gttgttggac gattatacta aaatgaagga agccatcctt    240
caggtgtact ggcaggaatt taaagatgac cacgtgggtc ttatgtgcaa attcgcgcag    300
cccgcaagca gaagattga ccagaataaa ctcaagccag atgtgacga aagggcaat      360 ttgaccactg cagggttcgc ttgttctcaa tgtggacagc cgttgttcgt ttataagctc    420
```

```
gaacaggtga gtgagaaagg aaaggcgtat accaattact ttgggagatg taatgtggct    480
gagcatgaga agttaattct tctcgctcaa ttgaagcctg agaaagacag tgatgaggct    540
gtgacatact ctttgggtaa atttgggcaa cgggcattag atttttattc catccacgtg    600
actaaagaat caacccaccc agtgaagcct ctagctcaaa tcgctgggaa caggtacgcc    660
tcaggcccag taggaaaagc gctgtcagac gcatgtatgg gcactatcgc atccttcttg    720
agtaagtatc aggatattat catagagcac cagaaagtcg tgaagggtaa tcagaagaga    780
ttagaaagtc tcagagaatt agcgggtaaa gagaatttag aatacccatc agttacattg    840
ccaccgcagc cacatactaa ggagggcgtg gatgcctata acgaggtaat cgcaagggtt    900
cggatgtggg ttaacctaaa tttatggcaa aaacttaaac tgagtaggga cgatgctaag    960
cccttactcc gattgaaggg gtttccatct tttcctgtgg tagaacgccg cgagaatgag   1020
gtcgattggt ggaatacaat aaacgaggta agaagctga ttgatgcaaa gcgcgatatg   1080
ggtcgagtgt tctggtctgg ggtgacggcc gagaagcgca ataccatatt agagggttac   1140
aactatttgc caaacgaaaa tgatcacaaa aaacgtgagg gttccttgga gaatcccaaa   1200
aagcctgcca agcgtcaatt cggggatttg ttgttgtatc tagagaaaaa atatgcagga   1260
gactggggaa aagtcttcga cgaggcctgg gaacggatcg acaaaaaaat agcagggctt   1320
acttcacata ttgaaaggga agaagctaga acgcggagg acgctcaatc aaaggcagtg   1380
cttaccgatt ggctcagagc aaaggcatca ttcgttttag aacgattgaa ggaaatggac   1440
gagaaggaat tttacgcttg cgaaattcaa ttacaaaagt ggtacggtga cctccgtggt   1500
aaccccttg ctgtggaggc agagaacagg gttgtagata tctctggatt ttctattggt   1560
agtgatggtc acagtattca gtataggaat ttactagcat ggaaatacct tgagaacggc   1620
aagagagagt tctacttact aatgaattac ggcaagaaag gcaggattcg ctttaccgat   1680
ggaactgata ttaaaagag tggcaaatgg caagggcttc tatatggagg gggtaaggct   1740
aaagtgattg atttaacctt tgatcctgac gacgaacaac taattattct gcctctagcg   1800
tttggaactc gccaaggaag agaatttatc tggaacgact tgttgtcctt agagaccgga   1860
ctcatcaagc ttgcaaacgg cagagtaata gaaaagacaa tatataacaa aaagattggg   1920
agagatgaac cggctctctt cgttgcatta acattcgaga ggcgggaggt ggtggatcca   1980
tctaacataa agccggtaaa cttaattggc gtggatcgtg gtgaaaatat tccagctgtc   2040
atcgcattga cagacccaga gggttgccca ctgcctgaat tcaaagactc ttcaggtgga   2100
cccacagata ttctccgaat aggggagggt tacaaggaga agcagcgtgc tattcaagct   2160
gctaaagagg ttgagcagag gagggccggg ggttactccc gtaaattcgc ctctaaatct   2220
cgaaacttgg ccgacgatat ggttcggaat tctgctagag atctattta ccatgctgtt   2280
actcacgatg cagtcttggt gttcgagaat ttgtccaggg gtttcggtag acaaggaaag   2340
agaacattta tgaccgaaag acaatatacg aagatggaag actggctcac agctaagttg   2400
gcatatgagg gactgacatc caaaacttac ctatcgaaga cccttgcgca atatacgtcc   2460
aagacttgct ctaactgcgg atttactatt acgacggctg actatgatgg gatgcttgtg   2520
agattaaaaa agacctcgga tggttgggcc acaacattga acaataaaga gttgaaagct   2580
gagggccaaa taacttacta taataggtac aaacgccaaa cagtggaaaa ggagttgtcc   2640
gcagagttag acaggctttc tgaagaatcg gggaacaatg acatttcgaa gtggactaaa   2700
gggcgtcgtg acgaggcatt attccttgct aagaaaagat tctcccatag accagtgcag   2760
gagcagtttg tgtgcctgga ttgcggacac gaggttcacg cagatgagca agccgcattg   2820
```

| | |
|---|---:|
| aacattgcca ggtcgtggct ttttctgaac tctaatagca ccgaattcaa gtcatataag | 2880 |
| tcggggaaac aacccttttgt aggggcatgg caagcttttt ataagagaag gcttaaggag | 2940 |
| gtatggaagc ccaatgcata g | 2961 |

<210> SEQ ID NO 4
<211> LENGTH: 500
<212> TYPE: DNA
<213> ORGANISM: Medicago truncatula

<400> SEQUENCE: 4

| | |
|---|---:|
| aagggctctc tgtcatgatt tcatactttc attattgagc tctgtaatta caattatgac | 60 |
| catgagaaca tctcttattg tgtggccttt taattgctga tgttagtact gaaccaaagc | 120 |
| ttatcgtgat gatgtaaaag caataagtac ttgtttgtag cttctttgtg tctccctttg | 180 |
| ggcttaatac atctgtttag tgttgtggct ttggcataga cttctcttgg taataatgcc | 240 |
| ttgcaatgca aaatttcaat tatcaaattc tattatgttc tccttatg gtaacagctt | 300 |
| accctgtgga agatgagatt cttgagttga gtcattgcca atttttggca ttagcttttg | 360 |
| aattagtgaa ttttgacaaa aattaccgtg acactgattt tgttgaagct cttaagtgta | 420 |
| gtttttacaa aatttcagtg gctcgttgtg attatgtcaa actcacggcg aatgtagttc | 480 |
| ttacagaatt tcagtggctc | 500 |

<210> SEQ ID NO 5
<211> LENGTH: 4094
<212> TYPE: DNA
<213> ORGANISM: Artificial
<220> FEATURE:
<223> OTHER INFORMATION: Synthetic polynucleotide. DsCasX_Gm expression cassette comprising the promoter cassette, the DsCasX_Gm cassette and a 3' UTR

<400> SEQUENCE: 5

| | |
|---|---:|
| atcaacggag aaacaaagat aaaaatcaat tactcacatg aaagagtatt gatcacgagt | 60 |
| cactatggag cgacaatctc cagacaggat gtcagcatct tatcttcctt tgaagaaagc | 120 |
| atcatcaata acgatgtaat ggtggggaca tccactaagt tattgctctg caaacagctc | 180 |
| aaaaagctac tggccgacaa tcataattgc tcggcatgtg caggtggggc ctccactagc | 240 |
| aataatacaa gctttacagc ttgcagtgac tcatcctcca ataatggaga aaagacgtc | 300 |
| agcagtgacg aacaagggtc gaaagacttg cctatataag ggcattctcc cctcagttga | 360 |
| agatcatcga aagttggagc aataaactct ctcttcaaca aatctatctt ttatcttta | 420 |
| tcggtacctc agcatgggat ctaagaagag aagaattaaa caagatatgg agaagaggat | 480 |
| taacaagatt aggaagaaat tatccgctga taacgcaacc aaaccagttt ccgaagcgg | 540 |
| cccaatgaag actctgctcg ttagagtgat gacagacgat cttaagaaaa gactcgagaa | 600 |
| gcgtagaaag aagccggagg ttatgcccca ggtgatttct aataacgcag caaacaatct | 660 |
| tcgaatgttg ttggacgatt atactaaaat gaaggaagcc atccttcagg tgtactggca | 720 |
| ggaatttaaa gatgaccacg tgggtcttat gtgcaaattc gcgcagcccg caagcaagaa | 780 |
| gattgaccag aataaactca agccagagat ggacgaaaag gcaatttga ccactgcagg | 840 |
| gttcgcttgt tctcaatgtg acagccgtt gttcgtttat aagctcgaac aggtgagtga | 900 |
| gaaaggaaag gcgtatacca attactttgg gagatgtaat gtggctgagc atgagaagtt | 960 |
| aattcttctc gctcaattga agcctgagaa agacagtgat gaggctgtga catactcttt | 1020 |
| gggtaaattt gggcaacggg cattagattt ttattccatc cacgtgacta agaatcaac | 1080 |

```
ccacccagtg aagcctctag ctcaaatcgc tgggaacagg tgagcatcag cttttttcct    1140
tgattcagat ctcttggtga aattcgccaa ctctctactt ttttgtttct tctctaatat    1200
tcctgtgctc tgcttcttgc tgctgctgtt cttgtgttta ccaggtacgc ctcaggccca    1260
gtaggaaaag cgctgtcaga cgcatgtatg ggcactatcg catccttctt gagtaagtat    1320
caggatatta tcatagagca ccagaaagtc gtgaagggta atcagaagag attagaaagt    1380
ctcagagaat tagcgggtaa agagaattta gaatacccat cagttacatt gccaccgcag    1440
ccacatacta aggagggcgt ggatgcctat aacgaggtaa tcgcaagggt tcggatgtgg    1500
gttaacctaa atttatggca aaaacttaaa ctgagtaggg acgatgctaa gcccttactc    1560
cgattgaagg ggtttccatc ttttcctgtg gtagaacgcc gcgagaatga ggtcgattgg    1620
tggaatacaa taaacgaggt aaagaagctg attgatgcaa agcgcgatat gggtcgagtg    1680
ttctggtctg gggtgacggc cgagaagcgc aataccatat tagagggtta caactatttg    1740
ccaaacgaaa atgatcacaa aaaacgtgag ggttccttgg agaatcccaa aaagcctgcc    1800
aagcgtcaat tcggggattt gttgttgtat ctagagaaaa aatatgcagg agactgggga    1860
aaagtcttcg acgaggcctg ggaacggatc gacaaaaaaa tagcagggct tacttcacat    1920
attgaaaggg aagaagctag aaacgcggag gacgctcaat caaaggcagt gcttaccgat    1980
tggctcagag caaaggcatc attcgttttta gaacgattga aggaaatgga cgagaaggaa    2040
ttttacgctt gcgaaattca attacaaaag tggtacggtg acctccgtgg taacccccttt    2100 gctgtggagg cagagaacag ggttgtagat atctctggat tttctattgg tagtgatggt    2160
cacagtattc agtataggaa tttactagca tggaaatacc ttgagaacgg caagagagag    2220
ttctacttac taatgaatta cggcaagaaa ggcaggattc gctttaccga tggaactgat    2280
attaaaaaga gtggcaaatg gcaagggctt ctatatggag ggggtaaggc taaagtgatt    2340 gatttaaccct ttgatcctga cgacgaacaa ctaattattc tgcctctagc gtttggaact    2400
cgccaaggaa gagaatttat ctggaacgac ttgttgtcct tagagaccgg actcatcaag    2460
cttgcaaacg gcagagtaat agaaaagaca atatataaca aaaagattgg gagagatgaa    2520
ccggctctct tcgttgcatt aacattcgag aggcgggagg tggtggatcc atctaacata    2580
aagccggtaa acttaattgg cgtggatcgt ggtgaaaata ttccagctgt catcgcattg    2640
acagacccag agggttgccc actgcctgaa ttcaaagact cttcaggtgg acccacagat    2700
attctccgaa taggggaggg ttacaaggag aagcagcgtg ctattcaagc tgctaaagag    2760
gttgagcaga ggagggccgg gggttactcc cgtaaattcg cctctaaatc tcgaaacttg    2820
gccgacgata tggttcggaa ttctgctaga gatctatttt accatgctgt tactcacgat    2880
gcagtcttgg tgttcgagaa tttgtccagg ggtttcggta gacaaggaaa gagaacattt    2940
atgaccgaaa gacaatatac gaagatggaa gactggctca cagctaagtt ggcatatgag    3000
ggactgacat ccaaaactta cctatcgaag acccttgcgc aatatacgtc caagacttgc    3060
tctaactgcg gatttactat tacgacggct gactatgatg ggatgcttgt gagattaaaa    3120
aagacctcgg atggttgggc cacaacattg aacaataaag agttgaaagc tgagggccaa    3180
ataacttact ataataggta caaacgccaa acagtggaaa aggagttgtc cgcagagtta    3240
gacaggcttt ctgaagaatc ggggaacaat gacatttcga agtggactaa agggcgtcgt    3300
gacgaggcat tattcttgct taagaaaaga ttctccccata gaccagtgca ggagcagttt    3360
gtgtgcctgg attgcggaca cgaggttcac gcagatgagc aagccgcatt gaacattgcc    3420
aggtcgtggc ttttttctgaa ctctaatagc accgaattca agtcatataa gtcggggaaa    3480
```

```
caaccctttg taggggcatg gcaagctttt tataagagaa ggcttaagga ggtatggaag   3540
cccaatgcag gatctaagaa gagaagaatt aaacaagatt gagaggttaa ttaaaagggc   3600
tctctgtcat gatttcatac tttcattatt gagctctgta attacaatta tgaccatgag   3660
aacatctctt attgtgtggc cttttaattg ctgatgttag tactgaacca aagcttatcg   3720
tgatgatgta aaagcaataa gtacttgttt gtagcttctt tgtgtctccc tttgggctta   3780
atacatctgt ttagtgttgt ggctttggca tagacttctc ttggtaataa tgccttgcaa   3840
tgcaaaattt caattatcaa attctattat gttctcacct tatggtaaca gcttaccctg   3900
tggaagatga gattcttgag ttgagtcatt gccaattttt ggcattagct tttgaattag   3960
tgaattttga caaaaattac cgtgacactg attttgttga agctcttaag tgtagttttt   4020
acaaaatttc agtggctcgt tgtgattatg tcaaactcac ggcgaatgta gttcttacag   4080
aatttcagtg gctc                                                     4094
```

```
<210> SEQ ID NO 6
<211> LENGTH: 422
<212> TYPE: DNA
<213> ORGANISM: Dahlia mosaic virus

<400> SEQUENCE: 6
atcaacggag aaacaaagat aaaaatcaat tactcacatg aaagagtatt gatcacgagt     60
cactatggag cgacaatctc cagacaggat gtcagcatct tatcttcctt tgaagaaagc    120
atcatcaata acgatgtaat ggtggggaca tccactaagt tattgctctg caaacagctc    180
aaaaagctac tggccgacaa tcataattgc tcggcatgtg caggtggggc ctccactagc    240
aataatacaa gctttacagc ttgcagtgac tcatcctcca ataatggaga aaaagacgtc    300
agcagtgacg aacaagggtc gaaagacttg cctatataag ggcattctcc cctcagttga    360
agatcatcga aagttggagc aataaactct ctcttcaaca aatctatctt ttatctttta    420
tc                                                                   422
```

```
<210> SEQ ID NO 7
<211> LENGTH: 365
<212> TYPE: DNA
<213> ORGANISM: Dahlia mosaic virus

<400> SEQUENCE: 7
atcaacggag aaacaaagat aaaaatcaat tactcacatg aaagagtatt gatcacgagt     60
cactatggag cgacaatctc cagacaggat gtcagcatct tatcttcctt tgaagaaagc    120
atcatcaata acgatgtaat ggtggggaca tccactaagt tattgctctg caaacagctc    180
aaaaagctac tggccgacaa tcataattgc tcggcatgtg caggtggggc ctccactagc    240
aataatacaa gctttacagc ttgcagtgac tcatcctcca ataatggaga aaaagacgtc    300
agcagtgacg aacaagggtc gaaagacttg cctatataag ggcattctcc cctcagttga    360
agatc                                                                365
```

```
<210> SEQ ID NO 8
<211> LENGTH: 57
<212> TYPE: DNA
<213> ORGANISM: Dahlia mosaic virus

<400> SEQUENCE: 8
atcgaaagtt ggagcaataa actctctctt caacaaatct atcttttatc ttttatc        57
```

<210> SEQ ID NO 9
<211> LENGTH: 3149
<212> TYPE: DNA
<213> ORGANISM: Artificial
<220> FEATURE:
<223> OTHER INFORMATION: Synthetic polynucleotide. DsCasX_Gm cassette
      comprising nuclear localization sequences and DsCasX_Gm sequence
      with an intron operably dividing the CasX open reading frame into
      a 5' portion and a 3' portion

<400> SEQUENCE: 9

```
atgggatcta agaagagaag aattaaacaa gatatggaga gaggattaa caagattagg      60 aagaaattat ccgctgataa cgcaaccaaa ccagtttccc gaagcggccc aatgaagact    120
ctgctcgtta gagtgatgac agacgatctt aagaaaagac tcgagaagcg tagaaagaag    180
ccggaggtta tgccccaggt gatttctaat aacgcagcaa acaatcttcg aatgttgttg    240
gacgattata ctaaaatgaa ggaagccatc cttcaggtgt actggcagga atttaaagat    300
gaccacgtgg gtcttatgtg caaattcgcg cagcccgcaa gcaagaagat tgaccagaat    360
aaactcaagc cagagatgga cgaaaagggc aatttgacca ctgcagggtt cgcttgttct    420
caatgtggac agccgttgtt cgtttataag ctcgaacagg tgagtgagaa aggaaaggcg    480
tataccaatt actttgggag atgtaatgtg gctgagcatg agaagttaat tcttctcgct    540
caattgaagc ctgagaaaga cagtgatgag gctgtgacat actctttggg taaatttggg    600
caacgggcat tagatttta ttccatccac gtgactaaag aatcaaccca cccagtgaag    660
cctctagctc aaatcgctgg gaacaggtga gcatcagctt ttttccttga ttcagatctc    720
ttggtgaaat tcgccaactc tctactttt tgtttcttct ctaatattcc tgtgctctgc    780
ttcttgctgc tgctgttctt gtgtttacca ggtacgcctc aggcccagta ggaaaagcgc    840
tgtcagacgc atgtatgggc actatcgcat ccttcttgag taagtatcag gatattatca    900
tagagcacca gaaagtcgtg aagggtaatc agaagagatt agaaagtctc agagaattag    960
cgggtaaaga gaatttagaa tacccatcag ttacattgcc accgcagcca catactaagg   1020
agggcgtgga tgcctataac gaggtaatcg caagggttcg gatgtgggtt aacctaaatt   1080
tatggcaaaa acttaaactg agtagggacg atgctaagcc cttactccga ttgaaggggt   1140
ttccatcttt tcctgtggta gaacgccgcg agaatgaggt cgattggtgg aatacaataa   1200
acgaggtaaa gaagctgatt gatgcaaagc gcgatatggg tcgagtgttc tggtctgggg   1260
tgacggccga gaagcgcaat accatattag agggttacaa ctatttgcca aacgaaaatg   1320
atcacaaaaa acgtgagggt tccttggaga atcccaaaaa gcctgccaag cgtcaattcg   1380
gggatttgtt gttgtatcta gagaaaaaat atgcaggaga ctggggaaaa gtcttcgacg   1440
aggcctggga acggatcgac aaaaaaatag cagggcttac ttcacatatt gaagggaag   1500 aagctagaaa cgcggaggac gctcaatcaa aggcagtgct taccgattgg ctcagagcaa   1560
aggcatcatt cgttttagaa cgattgaagg aaatggacga aaggaattt tacgcttgcg   1620 aaattcaatt acaaaagtgg tacggtgacc tccgtggtaa ccccttgct gtggaggcag   1680 agaacagggt tgtagatatc tctggatttt ctattggtag tgatggtcac agtattcagt   1740
ataggaattt actagcatgg aaataccttg agaacggcaa agagagttc tacttactaa   1800 tgaattacgg caagaaaggc aggattcgct ttaccgatgg aactgatatt aaaagagtg   1860 gcaaatggca agggcttcta tatggagggg gtaaggctaa agtgattgat ttaaccttg   1920 atcctgacga cgaacaacta attattctgc ctctagcgtt tggaactcgc caggaagag   1980 aatttatctg gaacgacttg ttgtccttag agaccggact catcaagctt gcaaacggca   2040
```

```
gagtaataga aaagacaata tataacaaaa agattgggag agatgaaccg gctctcttcg    2100
ttgcattaac attcgagagg cgggaggtgg tggatccatc taacataaag ccggtaaact    2160
taattggcgt ggatcgtggt gaaaatattc cagctgtcat cgcattgaca gacccagagg    2220
gttgcccact gcctgaattc aaagactctt caggtggacc cacagatatt ctccgaatag    2280
gggagggtta caaggagaag cagcgtgcta ttcaagctgc taaagaggtt gagcagagga    2340
gggccggggg ttactcccgt aaattcgcct ctaaatctcg aaacttggcc gacgatatgg    2400
ttcggaattc tgctagagat ctattttacc atgctgttac tcacgatgca gtcttggtgt    2460
tcgagaattt gtccaggggt ttcggtagac aaggaaagag aacatttatg accgaaagac    2520
aatatacgaa gatggaagac tggctcacag ctaagttggc atatgaggga ctgacatcca    2580
aaacttacct atcgaagacc cttgcgcaat atacgtccaa gacttgctct aactgcggat    2640
ttactattac gacggctgac tatgatggga tgcttgtgag attaaaaaag acctcggatg    2700
gttgggccac aacattgaac aataaagagt tgaaagctga gggccaaata acttactata    2760
ataggtacaa acgccaaaca gtggaaaagg agttgtccgc agagttagac aggctttctg    2820
aagaatcggg gaacaatgac atttcgaagt ggactaaagg cgtcgtgac gaggcattat    2880 tcttgcttaa gaaaagattc tcccatagac cagtgcagga gcagtttgtg tgcctggatt    2940
gcggacacga ggttcacgca gatgagcaag ccgcattgaa cattgccagg tcgtggcttt    3000
ttctgaactc taatagcacc gaattcaagt catataagtc ggggaaacaa ccctttgtag    3060
gggcatggca agctttttat aagagaaggc ttaaggaggt atggaagccc aatgcaggat    3120
ctaagaagag aagaattaaa caagattga                                    3149

<210> SEQ ID NO 10
<211> LENGTH: 30
<212> TYPE: DNA
<213> ORGANISM: Solanum lycopersicum

<400> SEQUENCE: 10
ggatctaaga agagaagaat taaacaagat                                     30

<210> SEQ ID NO 11
<211> LENGTH: 653
<212> TYPE: DNA
<213> ORGANISM: Artificial
<220> FEATURE:
<223> OTHER INFORMATION: Synthetic polynucleotide. 5' portion of
      DsCasX_Gm

<400> SEQUENCE: 11
atggagaaga ggattaacaa gattaggaag aaattatccg ctgataacgc aaccaaacca     60
gtttcccgaa gcggcccaat gaagactctg ctcgttagag tgatgacaga cgatcttaag    120
aaaagactcg agaagcgtag aaagaagccg gaggttatgc cccaggtgat ttctaataac    180
gcagcaaaca atcttcgaat gttgttggac gattatacta aaatgaagga agccatcctt    240
caggtgtact ggcaggaatt taaagatgac acgtgggtc ttatgtgcaa attcgcgcag    300
cccgcaagca agaagattga ccagaataaa ctcaagccag atggacga aaagggcaat    360 ttgaccactg cagggttcgc ttgttctcaa tgtggacagc cgttgttcgt ttataagctc    420
gaacaggtga gtgagaaagg aaaggcgtat accaattact tgggagatg taatgtggct    480 gagcatgaga agttaattct tctcgctcaa ttgaagcctg agaaagacag tgatgaggct    540
```

| | |
|---|---|
| gtgacatact ctttgggtaa atttgggcaa cgggcattag attttattc catccacgtg | 600 |
| actaaagaat caacccaccc agtgaagcct ctagctcaaa tcgctgggaa cag | 653 |

<210> SEQ ID NO 12
<211> LENGTH: 125
<212> TYPE: DNA
<213> ORGANISM: Setaria italica

<400> SEQUENCE: 12

| | |
|---|---|
| gtgagcatca gcttttttcc ttgattcaga tctcttggtg aaattcgcca actctctact | 60 |
| tttttgtttc ttctctaata ttcctgtgct ctgcttcttg ctgctgctgt tcttgtgttt | 120 |
| accag | 125 |

<210> SEQ ID NO 13
<211> LENGTH: 2305
<212> TYPE: DNA
<213> ORGANISM: Artificial
<220> FEATURE:
<223> OTHER INFORMATION: Synthetic polynucleotide. 3' portion of DsCasX_Gm

<400> SEQUENCE: 13

| | |
|---|---|
| gtacgcctca ggcccagtag gaaaagcgct gtcagacgca tgtatgggca ctatcgcatc | 60 |
| cttcttgagt aagtatcagg atattatcat agagcaccag aaagtcgtga agggtaatca | 120 |
| gaagagatta gaaagtctca gagaattagc gggtaaagag aatttagaat acccatcagt | 180 |
| tacattgcca ccgcagccac atactaagga gggcgtggat gcctataacg aggtaatcgc | 240 |
| aagggttcgg atgtgggtta acctaaattt atggcaaaaa cttaaactga gtagggacga | 300 |
| tgctaagccc ttactccgat tgaaggggtt tccatcttt cctgtggtag aacgccgcga | 360 |
| gaatgaggtc gattggtgga atacaataaa cgaggtaaag aagctgattg atgcaaagcg | 420 |
| cgatatgggt cgagtgttct ggtctggggt gacggccgag aagcgcaata ccatattaga | 480 |
| gggttacaac tatttgccaa acgaaaatga tcacaaaaaa cgtgagggtt ccttggagaa | 540 |
| tcccaaaaag cctgccaagc gtcaattcgg ggatttgttg ttgtatctag agaaaaaata | 600 |
| tgcaggagac tggggaaaag tcttcgacga ggcctgggaa cggatcgaca aaaaaatagc | 660 |
| agggcttact tcacatattg aaagggaaga agctagaaac gcggaggacg ctcaatcaaa | 720 |
| ggcagtgctt accgattggc tcagagcaaa ggcatcattc gttttagaac gattgaagga | 780 |
| aatggacgag aaggaatttt acgcttgcga aattcaatta caaaagtggt acggtgacct | 840 |
| ccgtggtaac ccctttgctg tggaggcaga gaacagggtt gtagatatct ctggattttc | 900 |
| tattggtagt gatggtcaca gtattcagta taggaattta ctagcatgga atacccttga | 960 |
| gaacggcaag agagagttct acttactaat gaattacggc aagaaaggca ggattcgctt | 1020 |
| taccgatgga actgatatta aaagagtgg caaatggcaa gggcttctat atggaggggg | 1080 |
| taaggctaaa gtgattgatt taacctttga tcctgacgac gaacaactaa ttattctgcc | 1140 |
| tctagcgttt ggaactcgcc aaggaagaga atttatctgg aacgacttgt tgtccttaga | 1200 |
| gaccggactc atcaagcttg caaacggcag agtaatagaa aagacaatat ataacaaaaa | 1260 |
| gattgggaga gatgaaccgg ctctcttcgt tgcattaaca ttcgagaggc gggaggtggt | 1320 |
| ggatccatct aacataaagc cggtaaactt aattggcgtg gatcgtggtg aaaatattcc | 1380 |
| agctgtcatc gcattgacag acccagaggg ttgcccactg cctgaattca agactcttc | 1440 |
| aggtggaccc acagatattc tccgaatagg ggagggttac aaggagaagc agcgtgctat | 1500 |

```
tcaagctgct aaagaggttg agcagaggag ggccggggt  tactcccgta aattcgcctc    1560
taaatctcga aacttggccg acgatatggt tcggaattct gctagagatc tattttacca    1620
tgctgttact cacgatgcag tcttggtgtt cgagaatttg tccaggggtt tcggtagaca    1680
aggaaagaga acatttatga ccgaaagaca atatacgaag atggaagact ggctcacagc    1740
taagttggca tatgagggac tgacatccaa aacttaccta tcgaagaccc ttgcgcaata    1800
tacgtccaag acttgctcta actgcggatt tactattacg acggctgact atgatgggat    1860
gcttgtgaga ttaaaaaaga cctcggatgg ttgggccaca acattgaaca ataaagagtt    1920
gaaagctgag ggccaaataa cttactataa taggtacaaa cgccaaacag tggaaaagga    1980
gttgtccgca gagttagaca ggcttctga agaatcgggg aacaatgaca tttcgaagtg    2040
gactaaaggg cgtcgtgacg aggcattatt cttgcttaag aaaagattct cccatagacc    2100
agtgcaggag cagtttgtgt gcctggattg cggacacgag gttcacgcag atgagcaagc    2160
cgcattgaac attgccaggt cgtggctttt tctgaactct aatagcaccg aattcaagtc    2220
atataagtcg gggaaacaac cctttgtagg ggcatggcaa gctttttata agagaaggct    2280
taaggaggta tggaagccca atgca                                          2305
```

<210> SEQ ID NO 14
<211> LENGTH: 24
<212> TYPE: DNA
<213> ORGANISM: Glycine max

<400> SEQUENCE: 14

```
ttctgaattt gcgggttttg gatt                                           24
```

<210> SEQ ID NO 15
<211> LENGTH: 24
<212> TYPE: DNA
<213> ORGANISM: Glycine max

<400> SEQUENCE: 15

```
ttcgataaag ccgccaattg cttc                                           24
```

<210> SEQ ID NO 16
<211> LENGTH: 24
<212> TYPE: DNA
<213> ORGANISM: Glycine max

<400> SEQUENCE: 16

```
ttcagtgctt ccttcttcgg cttc                                           24
```

<210> SEQ ID NO 17
<211> LENGTH: 487
<212> TYPE: DNA
<213> ORGANISM: Glycine max

<400> SEQUENCE: 17

```
agttttagtg tttgaaaaaa aaagtataga taaatataaa atgttttata aaatataaaa    60
cgataaaaat gttttaaacg atatatatta taaaaaaaaa cgtttcaaaa ataaatacaa    120
aaatgttttt aaatatatat aatttaactc attaaagaaa ataaaaatgc aagtgcggtg    180
acaagacaag ctaaaagttg caaaagaaat ggcagggcta aaggctcac  ctactcctgg    240 atttaccaaa ttttggttcg tccctatact cgaaaaataa aacaaaataa atttcagtat    300
cttcgttttt gtatgctttg actgtgaggc gaggccaact ttcttcttct gtctgagatg    360 aatttttgttt gcctcctgtg aaggatgtat cattcaaagt gaatgttttg caactgccag    420
```

```
tagtcccaca tcgaccaaat attcttatta cagtgtgttt atatagcacc tggagaagga      480
atgggtt                                                                487

<210> SEQ ID NO 18
<211> LENGTH: 141
<212> TYPE: DNA
<213> ORGANISM: Artificial
<220> FEATURE:
<223> OTHER INFORMATION: Synthetic oligonucleotide. sgRNA_TS1.

<400> SEQUENCE: 18
gattacatct ggcgcgttta ttccattact ttggagccag tcccagcgac tatgtcgtat       60
ggacgaagcg cttatttatc ggagagaaaa ccgataagta aaacgcatca aaggaatttg      120
cgggttttgg attttttttt t                                                141

<210> SEQ ID NO 19
<211> LENGTH: 141
<212> TYPE: DNA
<213> ORGANISM: Artificial
<220> FEATURE:
<223> OTHER INFORMATION: Synthetic oligonucleotide. sgRNA_TS2.

<400> SEQUENCE: 19
gattacatct ggcgcgttta ttccattact ttggagccag tcccagcgac tatgtcgtat       60
ggacgaagcg cttatttatc ggagagaaaa ccgataagta aaacgcatca agataaagc       120 cgccaattgc ttctttttt t                                                 141

<210> SEQ ID NO 20
<211> LENGTH: 141
<212> TYPE: DNA
<213> ORGANISM: Artificial
<220> FEATURE:
<223> OTHER INFORMATION: Synthetic oligonucleotide. sgRNA_TS3.

<400> SEQUENCE: 20
gattacatct ggcgcgttta ttccattact ttggagccag tcccagcgac tatgtcgtat       60
ggacgaagcg cttatttatc ggagagaaaa ccgataagta aaacgcatca aggtgcttc       120 cttcttcggc ttctttttt t                                                 141

<210> SEQ ID NO 21
<211> LENGTH: 90
<212> TYPE: DNA
<213> ORGANISM: Artificial
<220> FEATURE:
<223> OTHER INFORMATION: Synthetic oligonucleotide. Donor-
      oligonucleotide

<400> SEQUENCE: 21
ttaagggata acagggtaat atagcgtaac tataacggtc ctaaggtagc gaattacgat       60
acaaggctac ctagcttcgc agttacgcta                                        90

<210> SEQ ID NO 22
<211> LENGTH: 26
<212> TYPE: DNA
<213> ORGANISM: Artificial
<220> FEATURE:
<223> OTHER INFORMATION: Synthetic oligonucleotide. Oligo-specific
      primer

<400> SEQUENCE: 22
ccttgtatcg taattcgcta ccttag                                            26
```

```
<210> SEQ ID NO 23
<211> LENGTH: 20
<212> TYPE: DNA
<213> ORGANISM: Artificial
<220> FEATURE:
<223> OTHER INFORMATION: Synthetic oligonucleotide. Primer Sequence
      EN2410

<400> SEQUENCE: 23
acataacaaa cactatttac                                              20

<210> SEQ ID NO 24
<211> LENGTH: 20
<212> TYPE: DNA
<213> ORGANISM: Artificial
<220> FEATURE:
<223> OTHER INFORMATION: Synthetic oligonucleotide. Primer Sequence
      EN2411

<400> SEQUENCE: 24
aattaatcgg gaaatcggac                                              20

<210> SEQ ID NO 25
<211> LENGTH: 20
<212> TYPE: DNA
<213> ORGANISM: Artificial
<220> FEATURE:
<223> OTHER INFORMATION: Synthetic oligonucleotide. Primer Sequence
      EN2412

<400> SEQUENCE: 25
aatcgcgtga ccttatactc                                              20

<210> SEQ ID NO 26
<211> LENGTH: 20
<212> TYPE: DNA
<213> ORGANISM: Artificial
<220> FEATURE:
<223> OTHER INFORMATION: Synthetic oligonucleotide. Primer Sequence
      EN2413

<400> SEQUENCE: 26
actgacacgc actcatacac                                              20

<210> SEQ ID NO 27
<211> LENGTH: 22
<212> TYPE: DNA
<213> ORGANISM: Artificial
<220> FEATURE:
<223> OTHER INFORMATION: Synthetic oligonucleotide.Primer Sequence
      EN1871

<400> SEQUENCE: 27
acwaacatcc aaccaacttg tc                                           22

<210> SEQ ID NO 28
<211> LENGTH: 21
<212> TYPE: DNA
<213> ORGANISM: Artificial
<220> FEATURE:
<223> OTHER INFORMATION: Synthetic oligonucleotide.Primer Sequence
      EN1866

<400> SEQUENCE: 28
tccagcaaag gacatcccct c                                            21
```

<210> SEQ ID NO 29
<211> LENGTH: 86
<212> TYPE: DNA
<213> ORGANISM: Glycine max

<400> SEQUENCE: 29
tgtcccacaa aatgaatttt gcatgtattc agtgcttcct tcttcggctt cactttttct    60
ggccggtgca gccggtaacc agtagt                                        86

<210> SEQ ID NO 30
<211> LENGTH: 83
<212> TYPE: DNA
<213> ORGANISM: Glycine max

<400> SEQUENCE: 30
tgtcccacaa aatgaatttt gcatgtattc agtgcttcct tcttcggggt aatatagcgt    60
aactataacg gtcctaaggt agc                                           83

<210> SEQ ID NO 31
<211> LENGTH: 20
<212> TYPE: DNA
<213> ORGANISM: Artificial
<220> FEATURE:
<223> OTHER INFORMATION: Synthetic oligonucleotide.Primer sequence
      EN2448

<400> SEQUENCE: 31
ccagaaaatc ggaaatggac                                               20

<210> SEQ ID NO 32
<211> LENGTH: 20
<212> TYPE: DNA
<213> ORGANISM: Artificial
<220> FEATURE:
<223> OTHER INFORMATION: Synthetic oligonucleotide.Primer sequence
      EN2449

<400> SEQUENCE: 32
ataagcgaag gagcaaaaag                                               20

<210> SEQ ID NO 33
<211> LENGTH: 20
<212> TYPE: DNA
<213> ORGANISM: Artificial
<220> FEATURE:
<223> OTHER INFORMATION: Synthetic oligonucleotide. Primer sequence
      EN2450

<400> SEQUENCE: 33
agaaaaaggc tgagaagaag                                               20

<210> SEQ ID NO 34
<211> LENGTH: 22
<212> TYPE: DNA
<213> ORGANISM: Artificial
<220> FEATURE:
<223> OTHER INFORMATION: Synthetic oligonucleotide.Primer sequence
      EN2451

<400> SEQUENCE: 34
ggaatttaaa aaaagtagag ag                                            22

```
<210> SEQ ID NO 35
<211> LENGTH: 21
<212> TYPE: DNA
<213> ORGANISM: Artificial
<220> FEATURE:
<223> OTHER INFORMATION: Synthetic oligonucleotide.Primer sequence
      EN2452

<400> SEQUENCE: 35
cttacgtagt agttttttgt c                                              21

<210> SEQ ID NO 36
<211> LENGTH: 20
<212> TYPE: DNA
<213> ORGANISM: Artificial
<220> FEATURE:
<223> OTHER INFORMATION: Synthetic oligonucleotide.Primer sequence
      EN2453

<400> SEQUENCE: 36
gagcggtgat taagattttc                                                20

<210> SEQ ID NO 37
<211> LENGTH: 33
<212> TYPE: DNA
<213> ORGANISM: Artificial
<220> FEATURE:
<223> OTHER INFORMATION: Synthetic oligonucleotide.Illumina Forward
      adapter

<400> SEQUENCE: 37
tcgtcggcag cgtcagatgt gtataagaga cag                                 33

<210> SEQ ID NO 38
<211> LENGTH: 34
<212> TYPE: DNA
<213> ORGANISM: Artificial
<220> FEATURE:
<223> OTHER INFORMATION: Synthetic oligonucleotide.Illumina Reverse
      adapter

<400> SEQUENCE: 38
gtctcgtggg ctcggagatg tgtataagag acag                                34

<210> SEQ ID NO 39
<211> LENGTH: 2961
<212> TYPE: DNA
<213> ORGANISM: Artificial
<220> FEATURE:
<223> OTHER INFORMATION: Synthetic polynucleotide.DsCasX_Zm
      (Deltaproteobacteria sp. CasX sequence codon optimized for Corn)

<400> SEQUENCE: 39
atggagaagc gcatcaataa aatccggaag aagctctccg ctgacaacgc aaccaaaccc     60
gtgtcgagat ccggtccaat gaagacctta ctcgtgcggg tcatgactgga cgatctgaag   120 aagcgattgg agaaaagacg aaagaaacct gaggtcatgc cgcaggttat aagcaacaat   180
gccgccaaca acctcaggat gctacttgat gactatacta aaatgaagga ggctatcctt   240
caggtctact ggcaggagtt taaggatgac acgtggggc ttatgtgtaa attcgcacag    300
cctgcttcta agaagatcga tcagaacaag ttgaagccgg aaatggacga agggaaac    360 cttacgacag caggattcgc atgctcacag tgtggccagc ctttgtttgt ctataagctt   420
gaacaggtaa gcgagaaggg taaggcgtac actaattatt cgggcggtg taatgtcgcc   480 gaacacgaga agctgatact gctggcccaa ctcaaaccag agaaagactc ggacgaagct   540
```

| | |
|---|---|
| gtaacatata gcctaggaaa gtttggacag agggcacttg atttctattc gatccacgtc | 600 |
| accaaagaat cgacccatcc tgtcaagccg ttggctcaga ttgctggtaa cagatacgcg | 660 |
| agtggtcctg ttgggaaggc tctgtcagac gcctgcatgg gtaccattgc tagctttctc | 720 |
| agcaagtacc aagacataat cattgagcac agaaggtgg tcaaagggaa tcagaagcgg | 780 |
| ctcgagagcc tgcgtgaatt ggcaggcaag agaatcttg agtatccttc agttacattg | 840 |
| ccacccagc cgcataccaa agaggggtt gacgcctata atgaagtcat tgcacgggtg | 900 |
| agaatgtggg taaatttgaa cctatggcag aagctaaagc tctctcggga cgatgctaag | 960 |
| cctctgctga ggcttaaggg cttcccttcc ttccctgtag tcgaacgtcg ggagaatgag | 1020 |
| gtcgactggt ggaatactat aaacgaggtt aaaaagctga tcgatgctaa aagggacatg | 1080 |
| ggcagggtgt tttggagcgg cgtgactgcg gagaagagaa ataccatcct agaaggctat | 1140 |
| aactacctac ctaatgagaa tgatcacaaa agagggaag ggtcactcga aaatccaaag | 1200 |
| aaaccagcga agcggcagtt tggcgatctt ttgctatatc ttgaaaagaa gtatgctgga | 1260 |
| gattgggta aggtgtttga tgaggcttgg gagagaattg acaagaaaat agctgggcta | 1320 |
| acaagccaca tcgagagaga agaggcgagg aatgctgagg atgcacagag caaagcggtg | 1380 |
| ttgactgact ggctgcgtgc gaaggcatca tttgtcttgg agcgtcttaa agagatggat | 1440 |
| gaaaaggaat tttatgcatg cgagattcag ctccagaagt ggtatggaga cttgcgcggg | 1500 |
| aaccctttcg ccgttgaggc agaaaacagg gttgtagaca tttccggatt cagcattggg | 1560 |
| tctgatggac attctataca gtaccgcaac ctactagcat ggaagtacct agagaatggt | 1620 |
| aaacgtgagt tttatctgct catgaactac ggcaagaaag gccgtattcg gtttaccgac | 1680 |
| gggacggaca taaaaaagtc agggaaatgg cagggtcttc tttatggcgg aggcaaggca | 1740 |
| aaagtcatcg atttaacctt tgatccggac gatgagcagc ttattatttt gccattggcc | 1800 |
| tttggcactc gtcaggggag ggaatttata tggaatgatc tcctgtcact ggagaccggc | 1860 |
| cttattaaat tggctaacgg ccgggtaatc gaaaaaacaa tttataataa gaaaatcggg | 1920 |
| cgtgatgaac cagctctgtt cgttgccctg acatttgaaa gaagggaagt agtcgatcca | 1980 |
| tctaacatca aaccagtgaa tctgattggg gtcgaccgcg gcgagaacat tcccgctgtg | 2040 |
| atagcactca cagaccccga aggatgtcca cttcccgagt tcaaggattc ttcgggcggt | 2100 |
| ccaacagata ttttacggat cggggaagga tataaagaaa acaacgagc tatccaggcc | 2160 |
| gccaaggaag ttgagcagag acgcgctggt ggatactcga gaaagttcgc atctaagagc | 2220 |
| cgcaatttgg cggatgacat ggttcgtaat tcagctcggg acctcttcta ccatgcagta | 2280 |
| acacacgacg cggtactcgt gttcgagaat ttgtcacgcg gatttggacg ccaagggaag | 2340 |
| aggacgttca tgacagagag gcagtacacc aaaatggagg actggctcac ggccaagctt | 2400 |
| gcatacgaag gcctaacatc aaaaacatat ttgagcaaga cactcgcaca atacacatct | 2460 |
| aagacgtgct ctaactgtgg ttttacgata accaccgccg actacgacgg aatgctggtg | 2520 |
| cggctgaaaa aaacttcaga tggttgggcc acgacactta caataagga gttgaaagca | 2580 |
| gagggccaaa ttacctacta caaccggtat aaacgccaaa cggtggagaa ggagttatct | 2640 |
| gcagaacttg accggctctc cgaagagagt ggaaataatg acatcagtaa gtggactaag | 2700 |
| ggacgcagag atgaggccct gtttctcttg aaaaagcgtt tttcgcatag gcctgtgcaa | 2760 |
| gagcaattcg tgtgcctcga ttgcggtcat gaggtacatg cagatgagca agcggcctta | 2820 |
| aacatcgcta ggtcctggct cttcttaaac agtaactcga cggaatttaa gtcatataag | 2880 |

| | |
|---|---|
| tccggtaagc agccgttcgt tggagcctgg caagccttct acaagcgtag attgaaggag | 2940 |
| gtttggaagc cgaacgcgta g | 2961 |

<210> SEQ ID NO 40
<211> LENGTH: 578
<212> TYPE: DNA
<213> ORGANISM: Oryza sativa

<400> SEQUENCE: 40

| | |
|---|---|
| tctacaagac agaagatgaa tttcatgaca atactaggaa tacaaaataa gcaacgaact | 60 |
| gaagaaggat gcatcctggt taatccatcg accatgtctt agtagagttt tcttctgtgt | 120 |
| ttctgtgttg aagctttatg atttaccttta tactttagtc aagatgaata agaaataagt | 180 |
| atgtgtttcc gtgtgaggcg gtaatatgta gtaccttgta tttccatcca tcttcgtatg | 240 |
| gacaataata ataagacctc tgtttgcttc atgatataat caagctctca taagttgtat | 300 |
| agctgattta gcaatacctc gcaagctaga aagattgtct gtaattgttc attttatcat | 360 |
| catattcaaa tctttgtgaa ttccaaaact gacatgtcag tacaaaatct ggcaggagta | 420 |
| caaaactttc agctcctcac ctactcatga aaattcaatg taatacatag acatggcagg | 480 |
| gcagttaaca tattttggt ggcacgagtt aaagtcagca tcgagttgaa accatggatt | 540 |
| atacaagcag gattaagttg aaatttcaga agaaatag | 578 |

<210> SEQ ID NO 41
<211> LENGTH: 4980
<212> TYPE: DNA
<213> ORGANISM: Artificial
<220> FEATURE:
<223> OTHER INFORMATION: Synthetic polynucleotide. DsCasX_Zm expression
cassette comprising the promoter cassette , the DsCasX_Zm cassette
and the 3' UTR

<400> SEQUENCE: 41

| | |
|---|---|
| atcaacggag aaacaaagat aaaaatcaat tactcacatg aaagagtatt gatcacgagt | 60 |
| cactatggag cgacaatctc cagacaggat gtcagcatct tatcttcctt tgaagaaagc | 120 |
| atcatcaata acgatgtaat ggtggggaca tccactaagt tattgctctg caaacagctc | 180 |
| aaaaagctac tggccgacaa tcataattgc tcggcatgtg caggtggggc ctccactagc | 240 |
| aataatacaa gctttacagc ttgcagtgac tcatcctcca ataatggaga aaaagacgtc | 300 |
| agcagtgacg aacaagggtc gaaagacttg cctatataag ggcattctcc cctcagttga | 360 |
| agatcatcga aagttggagc aataaactct ctcttcaaca aatctatctt ttatctttta | 420 |
| tcggcgcgcc gggccaccgt cttcggtacg cgctcactcc gccctctgcc tttgttactg | 480 |
| ccacgtttct ctgaatgctc tcttgtgtgg tgattgctga gagtggttta gctggatcta | 540 |
| gaattacact ctgaaatcgt gttctgcctg tgctgattac ttgccgtcct tgtagcagc | 600 |
| aaaatatagg gacatggtag tacgaaacga agatagaacc tacacagcaa tacgagaaat | 660 |
| gtgtaatttg gtgcttagcg gtatttattt aagcacatgt tggtgttata gggcacttgg | 720 |
| attcagaagt ttgctgttaa tttaggcaca ggcttcatac tacatgggtc aatagtatag | 780 |
| ggattcatat tataggcgat actataataa tttgttcgtc tgcagagctt attatttgcc | 840 |
| aaaattagat attcctattc tgttttttgtt tgtgtgctgt taaattgtta acgcctgaag | 900 |
| gaataaatat aaatgacgaa attttgatgt ttatctctgc tcctttattg tgaccataag | 960 |
| tcaagatcag atgcacttgt tttaaatatt gttgtctgaa gaataagta ctgacagtat | 1020 |
| tttgatgcat tgatctgctt gtttgttgta acaaaattta aaaataaaga gtttccttttt | 1080 |

```
tgttgctctc cttacctcct gatggtatct agtatctacc aactgacact atattgcttc   1140
tctttacata cgtatcttgc tcgatgcctt ctccctagtg ttgaccagtg ttactcacat   1200
agtctttgct catttcattg taatgcagat accaagcggg gtaccatggg atctaagaag   1260
agaagaatta aacaagatat ggagaagcgc atcaataaaa tccggaagaa gctctccgct   1320
gacaacgcaa ccaaacccgt gtcgagatcc ggtccaatga agaccttact cgtgcgggtc   1380
atgacggacg atctgaagaa gcgattggag aaaagacgaa agaaacctga ggtcatgccg   1440
caggttataa gcaacaatgc cgccaacaac ctcaggatgc tacttgatga ctatactaaa   1500
atgaaggagg ctatccttca ggtctactgg caggagttta aggatgacca cgtgggggctt   1560 atgtgtaaat tcgcacagcc tgcttctaag aagatcgatc agaacaagtt gaagccggaa   1620
atggacgaga agggaaacct tacgacagca ggattcgcat gctcacagtg tggccagcct   1680
ttgtttgtct ataagcttga acaggtaagc gagaagggta aggcgtacac taattatttc   1740
gggcggtgta atgtcgccga acacgagaag ctgatactgc tggcccaact caaaccagag   1800
aaagactcgg acgaagctgt aacatatagc ctaggaaagt ttggacagag ggcacttgat   1860
ttctattcga tccacgtcac caaagaatcg acccatcctg tcaagccgtt ggctcagatt   1920
gctggtaaca gatcgcgag tggtcctgtt gggaaggctc tgtcagacgc ctgcatgggt   1980
accattgcta gctttctcag caagtaccaa gacataatca ttgagcacca gaaggtgagc   2040
atcagctttt ttccttgatt cagatctctt ggtgaaattc gccaactctc tactttttg    2100 tttcttctct aatattcctg tgctctgctt cttgctgctg ctgttcttgt gtttaccagg   2160
tggtcaaagg gaatcagaag cggctcgaga gcctgcgtga attggcaggc aaggagaatc   2220
ttgagtatcc ttcagttaca ttgccacccc agccgcatac caaagagggg gttgacgcct   2280
ataatgaagt cattgcacgg gtgagaatgt gggtaaattt gaacctatgg cagaagctaa   2340
agctctctcg ggacgatgct aagcctctgc tgaggcttaa gggcttccct tccttccctg   2400
tagtcgaacg tcgggagaat gaggtcgact ggtggaatac tataaacgag gttaaaaagc   2460
tgatcgatgc taaagggac atgggcaggg tgttttggag cggcgtgact gcggagaaga   2520
gaaataccat cctagaaggc tataactacc tacctaatga gaatgatcac aaaaagaggg   2580
aagggtcact cgaaaatcca agaaaccag cgaagcggca gtttggcgat cttttgctat   2640
atcttgaaaa gaagtatgct ggagattggg gtaaggtgtt tgatgaggct tgggagagaa   2700
ttgacaagaa aatagctggg ctaacaagcc acatcgagag agaagaggcg aggaatgctg   2760
aggatgcaca gagcaaagcg gtgttgactg actggctgcg tgcgaaggca tcatttgtct   2820
tggagcgtct taaagagatg gatgaaaagg aatttatgc atgcgagatt cagctccaga   2880
agtggtatgg agacttgcgc gggaacccctt tcgccgttga ggcagaaaac agggttgtag   2940
acatttccgg attcagcatt gggtctgatg gacattctat acagtaccgc aacctactag   3000 catgaagta cctagagaat ggtaaacgtg agttttatct gctcatgaac tacggcaaga   3060
aaggccgtat tcggtttacc gacgggacgg acataaaaaa gtcagggaaa tggcagggtc   3120
ttctttatgg cggaggcaag gcaaaagtca tcgatttaac ctttgatccg gacgatgagc   3180
agcttattat tttgccattg gccttttggca ctcgtcaggg gagggaattt atatggaatg   3240
atctcctgtc actggagacc ggccttatta aattggctaa cggccgggta atcgaaaaaa   3300
caatttataa taagaaaatc gggcgtgatg aaccagctct gttcgttgcc ctgacatttg   3360
aaagaaggga agtagtcgat ccatctaaca tcaaaccagt gaatctgatt ggggtcgacc   3420
gcggcgagaa cattcccgct gtgatagcac tcacagaccc cgaaggatgt ccacttcccg   3480
```

```
agttcaagga ttcttcgggc ggtccaacag atattttacg gatcggggaa ggatataaag    3540
aaaaacaacg agctatccag gccgccaagg aagttgagca gagacgcgct ggtggatact    3600
cgagaaagtt cgcatctaag agccgcaatt tggcggatga catggttcgt aattcagctc    3660
gggacctctt ctaccatgca gtaacacacg acgcggtact cgtgttcgag aatttgtcac    3720
gcggatttgg acgccaaggg aagaggacgt tcatgacaga gaggcagtac accaaaatgg    3780
aggactggct cacggccaag cttgcatacg aaggcctaac atcaaaaaca tatttgagca    3840
agacactcgc acaatacaca tctaagacgt gctctaactg tggttttacg ataaccaccg    3900
ccgactacga cggaatgctg gtgcggctga aaaaaacttc agatggttgg gccacgacac    3960
ttaacaataa ggagttgaaa gcagagggcc aaattaccta ctacaaccgg tataaacgcc    4020
aaacggtgga aaggagtta tctgcagaac ttgaccggct ctccgaagag agtggaaata    4080
atgacatcag taagtggact aagggacgca gagatgaggc cctgtttctc ttgaaaaagc    4140 gttttttcgca taggcctgtg caagagcaat tcgtgtgcct cgattgcggt catgaggtac    4200
atgcagatga gcaagcggcc ttaaacatcg ctaggtcctg gctcttctta aacagtaact    4260
cgacggaatt taagtcatat aagtccggta agcagccgtt cgttggagcc tggcaagcct    4320
tctacaagcg tagattgaag gaggtttgga agccgaacgc gggatctaag aagagaagaa    4380
ttaaacaaga ttagttaatt aatctacaag acagaagatg aatttcatga caatactagg    4440
aatacaaaat aagcaacgaa ctgaagaagg atgcatcctg gttaatccat cgaccatgtc    4500
ttagtagagt tttcttctgt gtttctgtgt tgaagcttta tgatttacct tatactttag    4560
tcaagatgaa taagaaataa gtatgtgttt ccgtgtgagg cggtaatatg tagtaccttg    4620
tatttccatc catcttcgta tggacaataa taataagacc tctgtttgct tcatgatata    4680
atcaagctct cataagttgt atagctgatt tagcaatacc tcgcaagcta gaaagattgt    4740
ctgtaattgt tcattttatc atcatattca aatctttgtg aattccaaaa ctgacatgtc    4800
agtacaaaat ctggcaggag tacaaaactt tcagctcctc acctactcat gaaaattcaa    4860
tgtaatacat agacatggca gggcagttaa catattttg gtggcacgag ttaaagtcag    4920
catcgagttg aaaccatgga ttatacaagc aggattaagt tgaaatttca gaagaaatag    4980
```

<210> SEQ ID NO 42
<211> LENGTH: 1239
<212> TYPE: DNA
<213> ORGANISM: Artificial
<220> FEATURE:
<223> OTHER INFORMATION: Chimeric DNA molecule comprising promoter cassette from Dahlia Mosaic Virus fused to an intron sequence from Zea mays.

<400> SEQUENCE: 42

```
atcaacggag aaacaaagat aaaaatcaat tactcacatg aaagagtatt gatcacgagt      60
cactatggag cgacaatctc cagacaggat gtcagcatct tatcttcctt tgaagaaagc     120
atcatcaata acgatgtaat ggtggggaca tccactaagt tattgctctg caaacagctc     180
aaaaagctac tggccgacaa tcataattgc tcggcatgtg caggtggggc ctccactagc     240
aataatacaa gctttacagc ttgcagtgac tcatcctcca ataatggaga aaaagacgtc     300
agcagtgacg aacaagggtc gaaagacttg cctatataag ggcattctcc cctcagttga     360
agatcatcga aagttggagc aataaactct ctcttcaaca aatctatctt ttatctttta     420
tcggcgcgcc gggccaccgt cttcggtacg cgctcactcc gccctctgcc tttgttactg     480
ccacgttcct ctgaatgctc tcttgtgtgg tgattgctga gagtggttta gctggatcta     540
```

```
gaattacact ctgaaatcgt gttctgcctg tgctgattac ttgccgtcct ttgtagcagc      600
aaaatatagg gacatggtag tacgaaacga agatagaacc tacacagcaa tacgagaaat      660
gtgtaatttg gtgcttagcg gtatttattt aagcacatgt tggtgttata gggcacttgg      720
attcagaagt ttgctgttaa tttaggcaca ggcttcatac tacatgggtc aatagtatag      780
ggattcatat tataggcgat actataataa tttgttcgtc tgcagagctt attatttgcc      840
aaaattagat attcctattc tgtttttgtt tgtgtgctgt taaattgtta acgcctgaag      900
gaataaatat aaatgacgaa attttgatgt ttatctctgc tcctttattg tgaccataag      960
tcaagatcag atgcacttgt tttaaatatt gttgtctgaa gaataagta ctgacagtat      1020 tttgatgcat tgatctgctt gtttgttgta acaaaattta aaaataaaga gtttccttt      1080 tgttgctctc cttacctcct gatggtatct agtatctacc aactgacact atattgcttc      1140
tctttacata cgtatcttgc tcgatgcctt ctccctagtg ttgaccagtg ttactcacat      1200
agtctttgct catttcattg taatgcagat accaagcgg                            1239

<210> SEQ ID NO 43
<211> LENGTH: 804
<212> TYPE: DNA
<213> ORGANISM: Zea mays

<400> SEQUENCE: 43
accgtcttcg gtacgcgctc actccgccct ctgcctttgt tactgccacg tttctctgaa       60
tgctctcttg tgtggtgatt gctgagagtg gtttagctgg atctagaatt acactctgaa      120
atcgtgttct gcctgtgctg attacttgcc gtcctttgta gcagcaaaat atagggacat      180
ggtagtacga aacgaagata gaacctacac agcaatacga gaatgtgta atttggtgct      240 tagcggtatt tatttaagca catgttggtg ttatagggca cttggattca gaagtttgct      300
gttaatttag gcacaggctt catactacat gggtcaatag tatagggatt catattatag      360
gcgatactat aataatttgt tcgtctgcag agcttattat ttgccaaaat tagatattcc      420
tattctgttt ttgtttgtgt gctgttaaat tgttaacgcc tgaaggaata aatataaatg      480
acgaaatttt gatgtttatc tctgctcctt tattgtgacc ataagtcaag atcagatgca      540
cttgttttaa atattgttgt ctgaagaaat aagtactgac agtattttga tgcattgatc      600
tgcttgtttg ttgtaacaaa atttaaaaat aaagagtttc cttttgttg ctctccttac      660 ctcctgatgg tatctagtat ctaccaactg acactatatt gcttctcttt acatacgtat      720
cttgctcgat gccttctccc tagtgttgac cagtgttact cacatagtct ttgctcattt      780
cattgtaatg cagataccaa gcgg                                             804

<210> SEQ ID NO 44
<211> LENGTH: 3149
<212> TYPE: DNA
<213> ORGANISM: Artificial
<220> FEATURE:
<223> OTHER INFORMATION: Synthetic polynucleotide. DsCasX_Zm cassette
      comprising  nuclear localization sequences  and theDsCasX_Gm
      sequence with an intron that operably divides the CasX  open
      reading frame into a 5' and 3' portion.

<400> SEQUENCE: 44
atgggatcta agaagagaag aattaaacaa gatatggaga agcgcatcaa taaaatccgg       60
aagaagctct ccgctgacaa cgcaaccaaa cccgtgtcga gatccggtcc aatgaagacc      120
ttactcgtgc gggtcatgac ggacgatctg aagaagcgat tggagaaaag acgaaagaaa      180
```

```
cctgaggtca tgccgcaggt tataagcaac aatgccgcca caaccctcag gatgctactt      240
gatgactata ctaaaatgaa ggaggctatc cttcaggtct actggcagga gtttaaggat      300
gaccacgtgg ggcttatgtg taaattcgca cagcctgctt ctaagaagat cgatcagaac      360
aagttgaagc cggaaatgga cgagaaggga aaccttacga cagcaggatt cgcatgctca      420
cagtgtggcc agcctttgtt tgtctataag cttgaacagg taagcgagaa gggtaaggcg      480
tacactaatt atttcgggcg gtgtaatgtc gccgaacacg agaagctgat actgctggcc      540
caactcaaac cagagaaaga ctcggacgaa gctgtaacat atagcctagg aaagtttgga      600
cagagggcac ttgatttcta ttcgatccac gtcaccaaag aatcgaccca tcctgtcaag      660
ccgttggctc agattgctgg taacagatac gcgagtggtc ctgttgggaa ggctctgtca      720
gacgcctgca tgggtaccat tgctagcttt ctcagcaagt accaagacat aatcattgag      780
caccagaagg tgagcatcag cttttttcct tgattcagat ctcttggtga aattcgccaa      840
ctctctactt ttttgtttct tctctaatat tcctgtgctc tgcttcttgc tgctgctgtt      900
cttgtgttta ccaggtggtc aaagggaatc agaagcggct cgagagcctg cgtgaattgg      960
caggcaagga gaatcttgag tatccttcag ttacattgcc accccagccg cataccaaag     1020 aggggggttga cgcctataat gaagtcattg cacggggtgag aatgtgggta aatttgaacc     1080
tatggcagaa gctaaagctc tctcgggacg atgctaagcc tctgctgagg cttaagggct     1140
tcccttcctt ccctgtagtc gaacgtcggg agaatgaggt cgactggtgg aatactataa     1200
acgaggttaa aaagctgatc gatgctaaaa gggacatggg cagggtgttt tggagcggcg     1260
tgactgcgga gaagagaaat accatcctag aaggctataa ctacctacct aatgagaatg     1320
atcacaaaaa gagggaaggg tcactcgaaa atccaaagaa accagcgaag cggcagtttg     1380
gcgatctttt gctatatctt gaaaagaagt atgctgagaa ttggggtaag gtgtttgatg     1440
aggcttggga gagaattgac aagaaaatag ctgggctaac aagccacatc gagagagaag     1500
aggcgaggaa tgctgaggat gcacagagca aagcggtgtt gactgactgg ctgcgtgcga     1560
aggcatcatt tgtcttggag cgtcttaaag agatggatga aaaggaattt tatgcatgcg     1620
agattcagct ccagaagtgg tatggagact tgcgcgggaa ccctttcgcc gttgaggcag     1680
aaaacagggt tgtagacatt tccggattca gcattgggtc tgatggacat tctatacagt     1740
accgcaacct actagcatgg aagtacctag agaatggtaa acgtgagttt tatctgctca     1800
tgaactacgg caagaaaggc cgtattcggt ttaccgacgg gacggacata aaaaagtcag     1860
ggaaatggca gggtcttctt tatggcgag gcaaggcaaa agtcatcgat ttaacctttg     1920
atccggacga tgagcagctt attattttgc cattggcctt tggcactcgt caggggaggg     1980
aatttatatg gaatgatctc ctgtcactgg agaccggcct tattaaattg gctaacggcc     2040
gggtaatcga aaaacaatt tataataaga aaatcgggcg tgatgaacca gctctgttcg     2100
ttgccctgac atttgaaaga agggaagtag tcgatccatc taacatcaaa ccagtgaatc     2160 tgattgggt cgaccgcggc gagaacattc ccgctgtgat agcactcaca gaccccgaag     2220
gatgtccact tcccgagttc aaggattctt cgggcggtcc aacagatatt ttacggatcg     2280
gggaaggata taagaaaaa caacgagcta tccaggccgc caaggaagtt gagcagagac     2340
gcgctggtgg atactcgaga aagttcgcat ctaagagccg caatttggcg gatgacatgg     2400
ttcgtaattc agctcgggac ctcttctacc atgcagtaac acacgacgcg gtactcgtgt     2460
tcgagaattt gtcacgcgga tttggacgcc aaggaagag gacgttcatg acagagaggc     2520
agtacaccaa aatggaggac tggctcacgg ccaagcttgc atacgaaggc ctaacatcaa     2580
```

```
aaacatatttt gagcaagaca ctcgcacaat acacatctaa gacgtgctct aactgtggtt    2640
ttacgataac caccgccgac tacgacggaa tgctggtgcg gctgaaaaaa acttcagatg    2700
gttgggccac gacacttaac aataaggagt tgaaagcaga gggccaaatt acctactaca    2760
accggtataa acgccaaacg gtggagaagg agttatctgc agaacttgac cggctctccg    2820
aagagagtgg aaataatgac atcagtaagt ggactaaggg acgcagagat gaggccctgt    2880
ttctcttgaa aaagcgtttt tcgcataggc ctgtgcaaga gcaattcgtg tgcctcgatt    2940
gcggtcatga ggtacatgca gatgagcaag cggccttaaa catcgctagg tcctggctct    3000
tcttaaacag taactcgacg gaatttaagt catataagtc cggtaagcag ccgttcgttg    3060
gagcctggca agccttctac aagcgtagat tgaaggaggt ttggaagccg aacgcgggat    3120
ctaagaagag aagaattaaa caagattag                                       3149

<210> SEQ ID NO 45
<211> LENGTH: 756
<212> TYPE: DNA
<213> ORGANISM: Artificial
<220> FEATURE:
<223> OTHER INFORMATION: Synthetic polynucleotide. 5' portion of
      DsCasX_Zm

<400> SEQUENCE: 45
atggagaagc gcatcaataa aatccggaag aagctctccg ctgacaacgc aaccaaaccc      60
gtgtcgagat ccggtccaat gaagaccttta ctcgtgcggg tcatgacgga cgatctgaag    120
aagcgattgg agaaaagacg aaagaaacct gaggtcatgc cgcaggttat aagcaacaat    180
gccgccaaca acctcaggat gctacttgat gactatacta aaatgaagga ggctatcctt    240
caggtctact ggcaggagtt taaggatgac cacgtggggc ttatgtgtaa attcgcacag    300
cctgcttcta gaagatcga tcagaacaag ttgaagccgg aaatggacga aagggaaac    360 cttacgacag caggattcgc atgctcacag tgtggccagc ctttgttttgt ctataagctt    420 gaacaggtaa gcgagaaggg taaggcgtac actaattatt tcgggcggtg taatgtcgcc    480
gaacacgaga agctgatact gctggcccaa ctcaaaccag agaaagactc ggacgaagct    540
gtaacatata gcctaggaaa gtttggacag agggcacttg atttctattc gatccacgtc    600
accaaagaat cgacccatcc tgtcaagccg ttggctcaga ttgctggtaa cagatacgcg    660
agtggtcctg ttgggaaggc tctgtcagac gcctgcatgg gtaccattgc tagctttctc    720
agcaagtacc aagacataat cattgagcac cagaag                               756

<210> SEQ ID NO 46
<211> LENGTH: 2202
<212> TYPE: DNA
<213> ORGANISM: Artificial
<220> FEATURE:
<223> OTHER INFORMATION: Synthetic polynucleotide.3' portion of DsCas_Zm

<400> SEQUENCE: 46
gtggtcaaag ggaatcagaa gcggctcgag agcctgcgtg aattggcagg caaggagaat      60
cttgagtatc cttcagttac attgccaccc cagccgcata ccaaagaggg ggttgacgcc    120
tataatgaag tcattgcacg ggtgagaatg tgggtaaatt tgaacctatg gcagaagcta    180
aagctctctc gggacgatgc taagcctctg ctgaggctta agggcttccc ttccttccct    240
gtagtcgaac gtcgggagaa tgaggtcgac tggtggaata ctataaacga ggttaaaaag    300
ctgatcgatg ctaaaaggga catgggcagg gtgttttgga gcggcgtgac tgcggagaag    360
```

```
agaaatacca tcctagaagg ctataactac ctacctaatg agaatgatca caaaagagg     420
gaagggtcac tcgaaaatcc aaagaaacca gcgaagcggc agtttggcga tcttttgcta    480
tatcttgaaa agaagtatgc tggagattgg ggtaaggtgt ttgatgaggc ttgggagaga    540
attgacaaga aaatagctgg gctaacaagc cacatcgaga gagaagaggc gaggaatgct    600
gaggatgcac agagcaaagc ggtgttgact gactggctgc gtgcgaaggc atcatttgtc    660
ttggagcgtc ttaaagagat ggatgaaaag gaattttatg catgcgagat tcagctccag    720
aagtggtatg gagacttgcg cgggaaccct ttcgccgttg aggcagaaaa cagggttgta    780
gacatttccg gattcagcat tgggtctgat ggacattcta tacagtaccg caacctacta    840
gcatggaagt acctagagaa tggtaaacgt gagttttatc tgctcatgaa ctacggcaag    900
aaaggccgta ttcggtttac cgacgggacg gacataaaaa agtcaggaa atggcagggt     960
cttctttatg gcggaggcaa ggcaaaagtc atcgatttaa cctttgatcc ggacgatgag   1020
cagcttatta ttttgccatt ggcctttggc actcgtcagg ggagggaatt tatatggaat   1080
gatctcctgt cactggagac cggccttatt aaattggcta acggccgggt aatcgaaaaa   1140
acaatttata ataagaaaat cgggcgtgat gaaccagctc tgttcgttgc cctgacattt   1200
gaaagaaggg aagtagtcga tccatctaac atcaaaccag tgaatctgat tggggtcgac   1260
cgcggcgaga acattcccgc tgtgatagca ctcacagacc ccgaaggatg tccacttccc   1320
gagttcaagg attcttcggg cggtccaaca gatattttac ggatcgggga aggatataaa   1380
gaaaaacaac gagctatcca ggccgccaag gaagttgagc agagacgcgc tggtggatac   1440
tcgagaaagt tcgcatctaa gagccgcaat ttggcggatg acatggttcg taattcagct   1500
cgggacctct tctaccatgc agtaacacac gacgcggtac tcgtgttcga gaatttgtca   1560
cgcggatttg gacgccaagg gaagaggacg ttcatgacag agaggcagta caccaaaatg   1620
gaggactggc tcacgccaa gcttgcatac gaaggcctaa catcaaaaac atatttgagc    1680
aagacactcg cacaatacac atctaagacg tgctctaact gtggttttac gataaccacc   1740
gccgactacg acggaatgct ggtgcggctg aaaaaaactt cagatggttg ggccacgaca   1800
cttaacaata aggagttgaa agcagagggc caaattacct actacaaccg gtataaacgc   1860
caaacggtgg agaaggagtt atctgcagaa cttgaccggc tctccgaaga gagtggaaat   1920
aatgacatca gtaagtggac taagggacgc agagatgagg ccctgtttct cttgaaaaag   1980
cgttttcgc ataggcctgt gcaagagcaa ttcgtgtgcc tcgattgcgg tcatgaggta    2040
catgcagatg agcaagcggc cttaaacatc gctaggtcct ggctcttctt aaacagtaac   2100
tcgacggaat ttaagtcata taagtccggt aagcagccgt tcgttggagc ctggcaagcc   2160
ttctacaagc gtagattgaa ggaggtttgg aagccgaacg cg                      2202
```

<210> SEQ ID NO 47
<211> LENGTH: 24
<212> TYPE: DNA
<213> ORGANISM: Zea mays

<400> SEQUENCE: 47

```
ttcccacaac cacatcactt ccca                                            24
```

<210> SEQ ID NO 48
<211> LENGTH: 24
<212> TYPE: DNA
<213> ORGANISM: Zea mays

```
<400> SEQUENCE: 48
ttctgaattg cctacatcat tatg                                              24

<210> SEQ ID NO 49
<211> LENGTH: 24
<212> TYPE: DNA
<213> ORGANISM: Zea mays

<400> SEQUENCE: 49
ttcccaacat tggcaagctt actt                                              24

<210> SEQ ID NO 50
<211> LENGTH: 397
<212> TYPE: DNA
<213> ORGANISM: Zea mays

<400> SEQUENCE: 50
tcgtaaaata gtggtgtcca aagaatttcc aggcccagtt gtaaaagcta aaatgctatt       60
cgaatttcta ctagcagtaa gtcgtgttta gaaattattt ttttatatac cttttttcct      120
tctatgtaca gtaggacaca gtgtcagcgc cgcgttgacg gagaatattt gcaaaaaagt      180
aaaagagaaa gtcatagcgg cgtatgtgcc aaaaacttcg tcacagagag gccataaga      240 aacatggccc acggcccaat acgaagcacc gcgacgaagc ccaaacagca gtccgtaggt      300
ggagcaaagc gctgggtaat acgcaaacgt tttgtcccac cttgactaat cacaagagtg      360
gagcgtacct tataaaccga gccgcaagca ccgaatt                                397

<210> SEQ ID NO 51
<211> LENGTH: 140
<212> TYPE: DNA
<213> ORGANISM: Artificial
<220> FEATURE:
<223> OTHER INFORMATION: Synthetic oligonucleotide. sgRNA_TS4.

<400> SEQUENCE: 51
gattacatct ggcgcgttta ttccattact ttggagccag tcccagcgac tatgtcgtat       60
ggacgaagcg cttatttatc ggagagaaaa ccgataagta aaacgcatca agcacaacc      120 acatcacttc ccattttttt                                                  140

<210> SEQ ID NO 52
<211> LENGTH: 140
<212> TYPE: DNA
<213> ORGANISM: Artificial
<220> FEATURE:
<223> OTHER INFORMATION: Synthetic oligonucleotide. sgRNA_TS5.

<400> SEQUENCE: 52
gattacatct ggcgcgttta ttccattact ttggagccag tcccagcgac tatgtcgtat       60
ggacgaagcg cttatttatc ggagagaaaa ccgataagta aaacgcatca aggaattgc      120 ctacatcatt atgtttttt                                                   140

<210> SEQ ID NO 53
<211> LENGTH: 140
<212> TYPE: DNA
<213> ORGANISM: Artificial
<220> FEATURE:
<223> OTHER INFORMATION: Synthetic oligonucleotide. sgRNA_TS6.
```

-continued

```
<400> SEQUENCE: 53
gattacatct ggcgcgttta ttccattact ttggagccag tcccagcgac tatgtcgtat      60
ggacgaagcg cttatttatc ggagagaaaa ccgataagta aaacgcatca aagcaacatt     120
ggcaagctta cttttttttt                                                 140

<210> SEQ ID NO 54
<211> LENGTH: 20
<212> TYPE: DNA
<213> ORGANISM: Artificial
<220> FEATURE:
<223> OTHER INFORMATION: Synthetic oligonucleotide. Primer sequence
      EN2454

<400> SEQUENCE: 54
cctgacagaa gcccaacaac                                                  20

<210> SEQ ID NO 55
<211> LENGTH: 21
<212> TYPE: DNA
<213> ORGANISM: Artificial
<220> FEATURE:
<223> OTHER INFORMATION: Synthetic oligonucleotide. Primer sequence
      EN2455
<220> FEATURE:
<221> NAME/KEY: misc_feature
<222> LOCATION: (1)..(21)
<223> OTHER INFORMATION: r = g or a

<400> SEQUENCE: 55
gaaattttac tatrcgatca c                                                21

<210> SEQ ID NO 56
<211> LENGTH: 20
<212> TYPE: DNA
<213> ORGANISM: Artificial
<220> FEATURE:
<223> OTHER INFORMATION: Synthetic oligonucleotide. Primer sequence
      EN2456
<220> FEATURE:
<221> NAME/KEY: misc_feature
<222> LOCATION: (1)..(20)
<223> OTHER INFORMATION: r = g or a

<400> SEQUENCE: 56
aatctrttgg tgagctgaag                                                  20

<210> SEQ ID NO 57
<211> LENGTH: 20
<212> TYPE: DNA
<213> ORGANISM: Artificial
<220> FEATURE:
<223> OTHER INFORMATION: Synthetic oligonucleotide. Primer sequence
      EN2457
<220> FEATURE:
<221> NAME/KEY: misc_feature
<222> LOCATION: (1)..(20)
<223> OTHER INFORMATION: w = a or t , y = t or c

<400> SEQUENCE: 57
aattgcawas tttgtyaggc                                                  20

<210> SEQ ID NO 58
<211> LENGTH: 20
<212> TYPE: DNA
<213> ORGANISM: Artificial
```

-continued

```
<220> FEATURE:
<223> OTHER INFORMATION: Synthetic oligonucleotide. Primer sequence
      EN2458
<220> FEATURE:
<221> NAME/KEY: misc_feature
<222> LOCATION: (1)..(20)
<223> OTHER INFORMATION: w = a or t , r = g or a , y = t or c

<400> SEQUENCE: 58
tttaagwaag ctacgryatc                                            20

<210> SEQ ID NO 59
<211> LENGTH: 20
<212> TYPE: DNA
<213> ORGANISM: Artificial
<220> FEATURE:
<223> OTHER INFORMATION: Synthetic oligonucleotide. Primer sequence
      EN2459
<220> FEATURE:
<221> NAME/KEY: misc_feature
<222> LOCATION: (1)..(20)
<223> OTHER INFORMATION: k = g or t , y = t or c

<400> SEQUENCE: 59
actcatakcc ttgcttctty                                            20

<210> SEQ ID NO 60
<211> LENGTH: 978
<212> TYPE: PRT
<213> ORGANISM: Unknown
<220> FEATURE:
<223> OTHER INFORMATION: Planctomycetes

<400> SEQUENCE: 60
```

Met Gln Glu Ile Lys Arg Ile Asn Lys Ile Arg Arg Arg Leu Val Lys
1               5                   10                  15

Asp Ser Asn Thr Lys Lys Ala Gly Lys Thr Gly Pro Met Lys Thr Leu
            20                  25                  30

Leu Val Arg Val Met Thr Pro Asp Leu Arg Glu Arg Leu Glu Asn Leu
        35                  40                  45

Arg Lys Lys Pro Glu Asn Ile Pro Gln Pro Ile Ser Asn Thr Ser Arg
    50                  55                  60

Ala Asn Leu Asn Lys Leu Leu Thr Asp Tyr Thr Glu Met Lys Lys Ala
65                  70                  75                  80

Ile Leu His Val Tyr Trp Glu Glu Phe Gln Lys Asp Pro Val Gly Leu
                85                  90                  95

Met Ser Arg Val Ala Gln Pro Ala Pro Lys Asn Ile Asp Gln Arg Lys
            100                 105                 110

Leu Ile Pro Val Lys Asp Gly Asn Glu Arg Leu Thr Ser Ser Gly Phe
        115                 120                 125

Ala Cys Ser Gln Cys Cys Gln Pro Leu Tyr Val Tyr Lys Leu Glu Gln
    130                 135                 140

Val Asn Asp Lys Gly Lys Pro His Thr Asn Tyr Phe Gly Arg Cys Asn
145                 150                 155                 160

Val Ser Glu His Glu Arg Leu Ile Leu Leu Ser Pro His Lys Pro Glu
                165                 170                 175

Ala Asn Asp Glu Leu Val Thr Tyr Ser Leu Gly Lys Phe Gly Gln Arg
            180                 185                 190

Ala Leu Asp Phe Tyr Ser Ile His Val Thr Arg Glu Ser Asn His Pro
        195                 200                 205

-continued

```
Val Lys Pro Leu Glu Gln Ile Gly Gly Asn Ser Cys Ala Ser Gly Pro
    210                 215                 220
Val Gly Lys Ala Leu Ser Asp Ala Cys Met Gly Ala Val Ala Ser Phe
225                 230                 235                 240
Leu Thr Lys Tyr Gln Asp Ile Ile Leu Glu His Gln Lys Val Ile Lys
                245                 250                 255
Lys Asn Glu Lys Arg Leu Ala Asn Leu Lys Asp Ile Ala Ser Ala Asn
                260                 265                 270
Gly Leu Ala Phe Pro Lys Ile Thr Leu Pro Pro Gln Pro His Thr Lys
                275                 280                 285
Glu Gly Ile Glu Ala Tyr Asn Asn Val Val Ala Gln Ile Val Ile Trp
290                 295                 300
Val Asn Leu Asn Leu Trp Gln Lys Leu Lys Ile Gly Arg Asp Glu Ala
305                 310                 315                 320
Lys Pro Leu Gln Arg Leu Lys Gly Phe Pro Ser Phe Pro Leu Val Glu
                325                 330                 335
Arg Gln Ala Asn Glu Val Asp Trp Trp Asp Met Val Cys Asn Val Lys
                340                 345                 350
Lys Leu Ile Asn Glu Lys Lys Glu Asp Gly Lys Val Phe Trp Gln Asn
                355                 360                 365
Leu Ala Gly Tyr Lys Arg Gln Glu Ala Leu Leu Pro Tyr Leu Ser Ser
                370                 375                 380
Glu Glu Asp Arg Lys Lys Gly Lys Lys Phe Ala Arg Tyr Gln Phe Gly
385                 390                 395                 400
Asp Leu Leu His Leu Glu Lys Lys His Gly Glu Asp Trp Gly Lys
                405                 410                 415
Val Tyr Asp Glu Ala Trp Glu Arg Ile Asp Lys Lys Val Glu Gly Leu
                420                 425                 430
Ser Lys His Ile Lys Leu Glu Glu Arg Arg Ser Glu Asp Ala Gln
                435                 440                 445
Ser Lys Ala Ala Leu Thr Asp Trp Leu Arg Ala Lys Ala Ser Phe Val
450                 455                 460
Ile Glu Gly Leu Lys Glu Ala Asp Lys Asp Glu Phe Cys Arg Cys Glu
465                 470                 475                 480
Leu Lys Leu Gln Lys Trp Tyr Gly Asp Leu Arg Gly Lys Pro Phe Ala
                485                 490                 495
Ile Glu Ala Glu Asn Ser Ile Leu Asp Ile Ser Gly Phe Ser Lys Gln
                500                 505                 510
Tyr Asn Cys Ala Phe Ile Trp Gln Lys Asp Gly Val Lys Lys Leu Asn
                515                 520                 525
Leu Tyr Leu Ile Ile Asn Tyr Phe Lys Gly Gly Lys Leu Arg Phe Lys
                530                 535                 540
Lys Ile Lys Pro Glu Ala Phe Glu Ala Asn Arg Phe Tyr Thr Val Ile
545                 550                 555                 560
Asn Lys Lys Ser Gly Glu Ile Val Pro Met Glu Val Asn Phe Asn Phe
                565                 570                 575
Asp Asp Pro Asn Leu Ile Ile Leu Pro Leu Ala Phe Gly Lys Arg Gln
                580                 585                 590
Gly Arg Glu Phe Ile Trp Asn Asp Leu Leu Ser Leu Glu Thr Gly Ser
                595                 600                 605
Leu Lys Leu Ala Asn Gly Arg Val Ile Glu Lys Thr Leu Tyr Asn Arg
610                 615                 620
```

```
Arg Thr Arg Gln Asp Glu Pro Ala Leu Phe Val Ala Leu Thr Phe Glu
625                 630                 635                 640

Arg Arg Glu Val Leu Asp Ser Ser Asn Ile Lys Pro Met Asn Leu Ile
            645                 650                 655

Gly Ile Asp Arg Gly Glu Asn Ile Pro Ala Val Ile Ala Leu Thr Asp
                660                 665                 670

Pro Glu Gly Cys Pro Leu Ser Arg Phe Lys Asp Ser Leu Gly Asn Pro
            675                 680                 685

Thr His Ile Leu Arg Ile Gly Glu Ser Tyr Lys Glu Lys Gln Arg Thr
690                 695                 700

Ile Gln Ala Ala Lys Glu Val Glu Gln Arg Arg Ala Gly Gly Tyr Ser
705                 710                 715                 720

Arg Lys Tyr Ala Ser Lys Ala Lys Asn Leu Ala Asp Asp Met Val Arg
            725                 730                 735

Asn Thr Ala Arg Asp Leu Leu Tyr Tyr Ala Val Thr Gln Asp Ala Met
                740                 745                 750

Leu Ile Phe Glu Asn Leu Ser Arg Gly Phe Gly Arg Gln Gly Lys Arg
            755                 760                 765

Thr Phe Met Ala Glu Arg Gln Tyr Thr Arg Met Glu Asp Trp Leu Thr
770                 775                 780

Ala Lys Leu Ala Tyr Glu Gly Leu Pro Ser Lys Thr Tyr Leu Ser Lys
785                 790                 795                 800

Thr Leu Ala Gln Tyr Thr Ser Lys Thr Cys Ser Asn Cys Gly Phe Thr
            805                 810                 815

Ile Thr Ser Ala Asp Tyr Asp Arg Val Leu Glu Lys Leu Lys Lys Thr
                820                 825                 830

Ala Thr Gly Trp Met Thr Thr Ile Asn Gly Lys Glu Leu Lys Val Glu
            835                 840                 845

Gly Gln Ile Thr Tyr Tyr Asn Arg Tyr Lys Arg Gln Asn Val Val Lys
850                 855                 860

Asp Leu Ser Val Glu Leu Asp Arg Leu Ser Glu Glu Ser Val Asn Asn
865                 870                 875                 880

Asp Ile Ser Ser Trp Thr Lys Gly Arg Ser Gly Glu Ala Leu Ser Leu
            885                 890                 895

Leu Lys Lys Arg Phe Ser His Arg Pro Val Gln Glu Lys Phe Val Cys
            900                 905                 910

Leu Asn Cys Gly Phe Glu Thr His Ala Asp Glu Gln Ala Ala Leu Asn
            915                 920                 925

Ile Ala Arg Ser Trp Leu Phe Leu Arg Ser Gln Glu Tyr Lys Lys Tyr
            930                 935                 940

Gln Thr Asn Lys Thr Thr Gly Asn Thr Asp Lys Arg Ala Phe Val Glu
945                 950                 955                 960

Thr Trp Gln Ser Phe Tyr Arg Lys Lys Leu Lys Glu Val Trp Lys Pro
            965                 970                 975

Ala Val

<210> SEQ ID NO 61
<211> LENGTH: 2937
<212> TYPE: DNA
<213> ORGANISM: Unknown
<220> FEATURE:
<223> OTHER INFORMATION: Planctomycetes
```

<400> SEQUENCE: 61

```
atgcaggaaa ttaaacgcat taacaaaatt cgccgccgcc tggtgaaaga tagcaacacc      60
aaaaaagcgg gcaaaaccgg cccgatgaaa accctgctgg tgcgcgtgat gaccccggat     120
ctgcgcgaac gcctggaaaa cctgcgcaaa aaaccggaaa acattccgca gccgattagc     180
aacaccagcc gcgcgaacct gaacaaactg ctgaccgatt ataccgaaat gaaaaaagcg     240
attctgcatg tgtattggga agaatttcag aaagatccgg tgggcctgat gagccgcgtg     300
gcgcagccgg cgccgaaaaa cattgatcag cgcaaactga ttccggtgaa agatggcaac     360
gaacgcctga ccagcagcgg ctttgcgtgc agccagtgct gccagccgct gtatgtgtat     420
aaactggaac aggtgaacga taaaggcaaa ccgcatacca actattttgg ccgctgcaac     480
gtgagcgaac atgaacgcct gattctgctg agcccgcata accggaagc gaacgatgaa      540
ctggtgacct atagcctggg caaatttggc cagcgcgcgc tggattttta tagcattcat     600
gtgacccgcg aaagcaacca tccggtgaaa ccgctggaac agattggcgg caacagctgc     660
gcgagcggcc cggtgggcaa agcgctgagc gatgcgtgca tgggcgcggt ggcgagcttt     720
ctgaccaaat atcaggatat tattctggaa catcagaaag tgattaaaaa aaacgaaaaa     780
cgcctggcga acctgaaaga tattgcgagc gcgaacggcc tggcgtttcc gaaaattacc     840
ctgccgccgc agccgcatac caaagaaggc attgaagcgt ataacaacgt ggtggcgcag     900
attgtgattt gggtgaacct gaacctgtgg cagaaactga aaattggccg cgatgaagcg     960
aaaccgctgc agcgcctgaa aggctttccg agctttccgc tggtggaacg ccaggcgaac    1020
gaagtggatt ggtgggatat ggtgtgcaac gtgaaaaaac tgattaacga aaaaaagaa     1080
gatggcaaag tgttttggca gaacctggcg ggctataaac gccaggaagc gctgctgccg    1140
tatctgagca gcgaagaaga tcgcaaaaaa ggcaaaaaat ttgcgcgcta tcagtttggc    1200
gatctgctgc tgcatctgga aaaaaaacat ggcgaagatt ggggcaaagt gtatgatgaa    1260
gcgtgggaac gcattgataa aaaagtggaa ggcctgagca acatattaa actgggaagaa    1320
gaacgccgca gcgaagatgc gcagagcaaa gcggcgctga ccgattggct gcgcgcgaaa    1380
gcgagctttg tgattgaagg cctgaaagaa gcggataaag atgaattttg ccgctgcgaa    1440
ctgaaactgc agaaatggta tggcgatctg cgcggcaaac cgtttgcgat gaagcggaa     1500
aacagcattc tggatattag cggctttagc aaacagtata actgcgcgtt tatttggcag    1560
aaagatggcg tgaaaaaact gaacctgtat ctgattatta actattttaa aggcggcaaa    1620
ctgcgcttta aaaaaattaa accggaagcg tttgaagcga accgcttta taccgtgatt     1680
aacaaaaaaa gcggcgaaat tgtgccgatg gaagtgaact ttaactttga tgatccgaac    1740
ctgattattc tgccgctggc gtttggcaaa cgccagggcc gcgaatttat ttggaacgat    1800
ctgctgagcc tggaaaccgg cagcctgaaa ctggcgaacg gccgcgtgat tgaaaaaacc    1860
ctgtataacc gccgcacccg ccaggatgaa ccggcgctgt tgtggcgct gacctttgaa     1920
cgccgcgaag tgctggatag cagcaacatt aaaccgatga acctgattgg cattgatcgc    1980
ggcgaaaaca ttccggcggt gattgcgctg accgatccgg aaggctgccc gctgagccgc    2040
tttaaagata gcctgggcaa cccgacccat attctgcgca ttggcgaaag ctataaagaa    2100
aaacagcgca ccattcaggc ggcgaaagaa gtggaacagc gccgcgcggg cggctatagc    2160
cgcaaatatg cgagcaaagc gaaaaacctg gcggatgata tggtgcgcaa caccgcgcgc    2220
gatctgctgt attatgcggt gacccaggat gcgatgctga ttttgaaaa cctgagccgc    2280
ggctttggcc gccagggcaa acgcaccttt atggcggaac gccagtatac ccgcatggaa    2340
```

```
gattggctga ccgcgaaact ggcgtatgaa ggcctgccga gcaaaaccta tctgagcaaa    2400
accctggcgc agtataccag caaaacctgc agcaactgcg gctttaccat taccagcgcg    2460
gattatgatc gcgtgctgga aaaactgaaa aaaaccgcga ccggctggat gaccaccatt    2520
aacggcaaag aactgaaagt ggaaggccag attacctatt ataaccgcta taaacgccag    2580
aacgtggtga agatctgag cgtggaactg gatcgcctga gcgaagaaag cgtgaacaac    2640
gatattagca gctggaccaa aggccgcagc ggcgaagcgc tgagcctgct gaaaaaacgc    2700
tttagccatc gcccggtgca ggaaaaattt gtgtgcctga actgcggctt tgaaacccat    2760
gcggatgaac aggcggcgct gaacattgcg cgcagctggc tgtttctgcg cagccaggaa    2820
tataaaaaat atcagaccaa caaaaccacc ggcaacaccg ataaacgcgc gtttgtggaa    2880
acctggcaga gcttttatcg caaaaaactg aaagaagtgt ggaaaccggc ggtgtaa       2937

<210> SEQ ID NO 62
<211> LENGTH: 2937
<212> TYPE: DNA
<213> ORGANISM: Artificial
<220> FEATURE:
<223> OTHER INFORMATION: Synthetic polynucleotide. PsCasX_Zm
      ( Planctomycetes sp. CasX sequence codon optimized for corn)

<400> SEQUENCE: 62
atgcaggaga tcaagagaat caacaaaatt cgccggagac tggtcaagga ttcgaacacg      60
aagaaggctg ggaagaccgg ccctatgaaa acgctcctgg taagggtgat gacaccggac     120
ctgagggaac ggctggaaaa tctgcggaaa aaacccgaga acattccgca accaatctct     180
aacacatcac gcgccaactt gaacaagctg cttacggatt acaccgagat gaaaaaggct     240
attctgcatg tctactggga ggagttccag aaggatcctg tgggactgat gtcgcgcgtt     300
gctcagccgg cgccaaaaaa cattgatcag cggaaattga ttcccgtgaa agatggaaac     360
gagcgcttaa cttcttccgg cttttgcctg tcacaatgct gccagcccct ctacgtgtac     420
aagcttgagc aagttaacga taagggcaag ccacatacta actactttgg gaggtgcaat     480
gtcagtgagc acgaacgact aattctcctg agccctcata gcccgaggc caatgacgag      540 ctggttacat atagtctagg caagttcggg cagcgggcct ggacttcta ctcgattcac      600 gtgactcgtg agtcaaacca tccggttaag ccgttggagc agataggtgg caatagctgc     660
gcttccggcc cagtgggaaa ggctctgtct gatgcttgta tgggcgcagt tgcgagtttc     720
cttacaaagt atcaggatat aatttttggag caccagaaag tcatcaagaa gaacgaaaaa     780
aggctggcaa atctaaaaga tattgcgtcc gccaatggtc tagcatttcc aaaaattaca      840
ctcccgccac aaccgcacac taaggagggg atagaggcat acaacaacgt ggtggctcag      900
attgtgatct gggtaaacct taatctgtgg caaaagctca aaattgggag ggatgaggca      960
aaaccacttc agagattgaa aggatttcct tccttcccgc ttgtggaacg tcaggctaac     1020
gaagtcgatt ggtgggacat ggtttgtaat gttaagaagc tgatcaacga gaaaaggaa     1080 gatgggaagg tgtttggca gaacttggcg gggtacaaaa ggcaagaagc cctactcccg     1140
tacctgtcaa gtgaagaaga ccgtaaaaag ggtaagaagt cgccagata tcagtttgga     1200 gatcttctgc tgcacttgga agaagcat ggtgaagatt ggggaaagt ttacgatgag     1260 gcctgggagc gaatagataa gaaggttgag ggtctatcca agcatattaa attggaggag     1320
gagcggcgat cggaagacgc ccagtctaag gcagcactta ctgattggtt gagggcaaaa     1380
gcatcttttg tcatcgaagg gctaaaggag gccgataagg atgaattttg caggtgtgag     1440
```

```
ctcaaacttc aaaaatggta tggagatctg aggggcaagc cattcgctat cgaggctgag    1500
aattctatac ttgatattag cggctttagc aaacagtata actgcgcatt catctggcaa    1560
aaagatggcg ttaaaaagtt gaatctctac cttattatca attatttcaa gggaggtaaa    1620
ttgcggttca agaagatcaa gcctgaagct tttgaggcca accgtttcta caccgtaatt    1680
aataagaaat caggggaaat tgtgccaatg gaagtaaact tcaattttga cgaccccaac    1740
cttatcattc tcccccctggc atttgggaag aggcaagggc gggaattcat ttggaatgat    1800
ttactttctc tcgagacagg tagtttgaaa ctggcaaatg gccgggtgat cgaaaaaaca    1860
ctttataatc ggcggacccg acaggatgag cctgcattgt ttgttgcact cacgtttgaa    1920
aggcgagaag tgttagattc atccaacatt aagccaatga atctcatcgg tattgatcga    1980
ggcgagaaca tcccagcagt tattgcactg accgatccag aagggtgccc cttgtcgagg    2040
tttaaggaca gtctgggcaa tccgacacat atacttcgga taggggaaag ttacaaggag    2100
aaacagagaa cgattcaggc agcaaaagag gttgaacagc gccgcgcagg aggttattcc    2160
agaaaatacg ctagcaaagc gaaaaatctt gccgatgaca tggttcggaa taccgcacgt    2220
gacctcctct attatgccgt gacacaagat gctatgttga tcttcgaaaa cctttcaaga    2280
ggattcggca ggcaaggcaa acgcactttt atggctgaga gacagtacac acgtatggaa    2340
gactggttga cggccaagct cgcttatgag gggctcccctt ccaaaaccta cttgtcgaaa    2400
acgctcgctc agtacacatc taagacttgc tccaactgtg gtttcacgat tacctccgcg    2460
gattatgaca gagtcttgga gaagttgaaa aaaactgcca caggctggat gactacaata    2520
aatgaaaagg agctgaaggt ggagggacag attacgtact ataatcgcta caaaaggcag    2580
aatgtagtaa aggacctgtc cgtggagctg atcgtctgt cggaggagtc ggttaacaac    2640
gacatttcat cttggaccaa agggcggagt ggggaagcac tttccttgct gaagaagcgc    2700
ttttcccacc gcccggtgca ggagaaattt gtgtgcctga actgtggctt cgagacccac    2760
gcggacgagc aggcggccct gaacatcgcg cgaagctggc tcttcctccg tagccaggag    2820
tacaagaagt accagacgaa caagacaacg ggcaatacag acaagcgggc attcgtggaa    2880
acttggcaga gttttttatag aaagaagttg aaggaggtct ggaaaccagc cgtgtga      2937
```

<210> SEQ ID NO 63
<211> LENGTH: 4956
<212> TYPE: DNA
<213> ORGANISM: Artificial
<220> FEATURE:
<223> OTHER INFORMATION: Synthetic polynucleotide. PsCasX_Zm expression cassette comprising the promoter cassette, the PsCasX_Zm cassette, and the 3' UTR
<400> SEQUENCE: 63

```
atcaacggag aaacaaagat aaaaatcaat tactcacatg aaagagtatt gatcacgagt     60
cactatggag cgacaatctc cagacaggat gtcagcatct tatcttcctt tgaagaaagc    120
atcatcaata acgatgtaat ggtggggaca tccactaagt tattgctctg caaacagctc    180
aaaaagctac tggccgacaa tcataattgc tcggcatgtg caggtggggc ctccactagc    240
aataatacaa gctttacagc ttgcagtgac tcatcctcca ataatggaga aaaagacgtc    300
agcagtgacg aacaagggtc gaaagacttg cctatataag ggcattctcc cctcagttga    360
agatcatcga aagttggagc aataaactct ctcttcaaca aatctatctt ttatcttta    420 tcggcgcgcc gggccaccgt cttcggtacg cgctcactcc gccctctgcc tttgttactg    480
ccacgttctt ctgaatgctc tcttgtgtgg tgattgctga gagtggttta gctggatcta    540
```

```
gaattacact ctgaaatcgt gttctgcctg tgctgattac ttgccgtcct ttgtagcagc    600
aaaatatagg gacatggtag tacgaaacga agatagaacc tacacagcaa tacgagaaat    660
gtgtaatttg gtgcttagcg gtatttattt aagcacatgt tggtgttata gggcacttgg    720
attcagaagt ttgctgttaa tttaggcaca ggcttcatac tacatgggtc aatagtatag    780
ggattcatat tataggcgat actataataa tttgttcgtc tgcagagctt attatttgcc    840
aaaattagat attcctattc tgttttttgtt tgtgtgctgt taaattgtta acgcctgaag    900
gaataaatat aaatgacgaa attttgatgt ttatctctgc tcctttattg tgaccataag    960
tcaagatcag atgcacttgt tttaaatatt gttgtctgaa gaataagta ctgacagtat    1020 tttgatgcat tgatctgctt gtttgttgta acaaaattta aaaataaaga gtttccttttt    1080 tgttgctctc cttacctcct gatggtatct agtatctacc aactgacact atattgcttc    1140
tctttacata cgtatcttgc tcgatgcctt ctccctagtg ttgaccagtg ttactcacat    1200
agtctttgct catttcattg taatgcagat accaagcggg gtaccatggg atctaagaag    1260
agaagaatta acaagatat gcaggagatc aagagaatca acaaaattcg ccggagactg    1320
gtcaaggatt cgaacacgaa gaaggctggg aagaccggcc ctatgaaaac gctcctggta    1380
agggtgatga caccggacct gagggaacgg ctggaaaatc tgcggaaaaa acccgagaac    1440
attccgcaac caatctctaa cacatcacgc gccaacttga acaagctgct tacggattac    1500
accgagatga aaaaggctat tctgcatgtc tactgggagg agttccagaa ggatcctgtg    1560
ggactgatgt cgcgcgttgc tcagccggcg ccaaaaaaca ttgatcagcg gaaattgatt    1620
cccgtgaaag atgaaacgga cgcttaact tcttccggct ttgcctgctc acaatgctgc    1680
cagcccctct acgtgtacaa gcttgagcaa gttaacgata agggcaagcc acatactaac    1740
tactttggga ggtgcaatgt cagtgagcac gaacgactaa ttctcctgag ccctcataag    1800
cccgaggcca atgacgagct ggttacatat agtctaggca agttcgggca gcgggccttg    1860
gacttctact cgattcacgt gactcgtgag tcaaaccatc cggttaagcc gttggagcag    1920
ataggtggca atagctgcgc ttccggccca gtgggaaagg ctctgtctga tgcttgtatg    1980
ggcgcagttg cgagtttcct tacaaagtat caggatataa ttttggagca ccagaaagtc    2040
atcaagaaga acgaaaaaag gctggcaaat ctaaagata ttgcgtccgc caatggtcta    2100
gcatttccaa aaattacact cccgccacaa ccgcacacta aggaggggat agaggcatac    2160
aacaacgtgg tggctcagat tgtgatctgg gtaaaccta atctgtggca aaagctcaaa    2220
attgggaggg atgaggcaaa accacttcag agattgaaag gatttccttc cttcccgctt    2280
gtggaacgtc aggctaacga agtcgattgg tgggacatgg tttgtaatgt taagaagctg    2340
atcaacgaga aaaaggaaga tgggaaggtg ttttggcaga acttggcggg gtacaaaagg    2400
caagaagccc tactcccgta cctgtcaagt gaagaagacc gtaaaaaggg taagaagttc    2460
gccagatatc agtttggaga tcttctgctg cacttggaga agaagcatgg tgaagattgg    2520
gggaaagttt acgatgaggc ctgggagcga atagataaga aggttgaggg tctatccaag    2580
catattaaat tggaggagga gcggcgatcg gaagacgccc agtctaaggc agcacttact    2640
gattggttga gggcaaaagc atcttttgtc atcgaagggc taaggaggc cgataaggat    2700 gaatttttgca ggtgtgagct caaacttcaa aaatggtatg gagatctgag gggcaagcca    2760
ttcgctatcg aggctgagaa ttctatactt gatattagcg gctttagcaa acagtataac    2820
tgcgcattca tctggcaaaa agatggcgtt aaaaagttga atctctacct tattatcaat    2880
tatttcaagg gaggtaaatt gcggttcaag aagatcaagc ctgaagcttt tgaggccaac    2940
```

```
cgtttctaca ccgtaattaa taagaaatca ggggaaattg tgccaatgga agtaaacttc      3000
aattttgacg accccaacct tatcattctc cccctggcat ttgggaagag caagggcgg       3060 gaattcattt ggaatgattt actttctctc gagacaggta gtttgaaact ggcaaatggc     3120
cgggtgatcg aaaaaacact ttataatcgg cggacccgac aggatgagcc tgcattgttt     3180
gttgcactca cgtttgaaag gcgagaagtg ttagattcat ccaacattaa gccaatgaat     3240
ctcatcggta ttgatcgagg cgagaacatc cagcagtta ttgcactgac cgatccagaa      3300
gggtgcccct tgtcgaggtt taaggacagt ctgggcaatc cgacacatat acttcggata     3360
ggggaaagtt acaaggagaa acagagaacg attcaggcag caaaagaggt tgaacagcgc     3420
cgcgcaggag gttattccag aaaatacgct agcaaagcga aaaatcttgc cgatgacatg     3480
gttcggaata ccgcacgtga cctcctctat tatgccgtga cacaagatgc tatgttgatc     3540
ttcgaaaacc tttcaagagg attcggcagg caaggcaaac gcacatttat ggctgagaga     3600
cagtacacac gtatggaaga ctggttgacg gccaagctcg cttatgaggg gctcccttcc     3660
aaaacctact tgtcgaaaac gctcgctcag tacacatcta agacttgctc caactgtggt     3720
ttcacgatta cctccgcgga ttatgacaga gtcttggaga agttgaaaaa aactgccaca     3780
ggctggatga ctacaataaa tggaaaggag ctgaaggtga gcatcagctt ttttccttga     3840
ttcagatctc ttggtgaaat tcgccaactc tctactttt tgtttcttct ctaatattcc      3900
tgtgctctgc ttcttgctgc tgctgttctt gtgtttacca ggtggaggga cagattacgt     3960
actataatcg ctacaaaagg cagaatgtag taaaggacct gtccgtggag ctggatcgtc     4020
tgtcggagga gtcggttaac aacgacattt catcttggac caagggcgg agtggggaag     4080 cactttcctt gctgaagaag cgcttttccc accgcccggt gcaggagaaa tttgtgtgcc     4140
tgaactgtgg cttcgagacc cacgcggacg agcaggcggc cctgaacatc gcgcgaagct     4200
ggctcttcct ccgtagccag gagtacaaga agtaccagac gaacaagaca acgggcaata     4260
cagacaagcg ggcattcgtg gaaacttggc agagtttta tagaaagaag ttgaaggagg     4320
tctggaaacc agccgtggga tctaagaaga gaagaattaa acaagattag ttaattaatc     4380
tacaagacag aagatgaatt tcatgacaat actaggaata caaataagc aacgaactga      4440 agaaggatgc atcctggtta atccatcgac catgtcttag tagagtttc ttctgtgttt       4500 ctgtgttgaa gctttatgat ttaccttata ctttagtcaa gatgaataag aaataagtat     4560
gtgtttccgt gtgaggcggt aatatgtagt accttgtatt tccatccatc ttcgtatgga     4620
caataataat aagacctctg tttgcttcat gatataatca agctctcata agttgtatag     4680
ctgatttagc aataccctcgc aagctagaaa gattgtctgt aattgttcat tttatcatca    4740
tattcaaatc tttgtgaatt ccaaaactga catgtcagta caaaatctgg caggagtaca     4800
aaactttcag ctcctcacct actcatgaaa attcaatgta atacatagac atggcagggc     4860
agttaacata ttttggtgg cacgagttaa agtcagcatc gagttgaaac catggattat       4920
acaagcagga ttaagttgaa atttcagaag aaatag                                4956
```

<210> SEQ ID NO 64
<211> LENGTH: 3119
<212> TYPE: DNA
<213> ORGANISM: Artificial
<220> FEATURE:
<223> OTHER INFORMATION: Synthetic polynucleotide. PsCasX_Zm cassette
      comprising the nuclear localization sequences and PsCasX_Zm
      sequence with an intron that operably divides the CasX open
      reading frame into a 5' portion and 3' portion

```
<400> SEQUENCE: 64
ggatctaaga agagaagaat taaacaagat atgcaggaga tcaagagaat caacaaaatt      60
cgccggagac tggtcaagga ttcgaacacg aagaaggctg ggaagaccgg ccctatgaaa     120
acgctcctgg taagggtgat gacaccggac ctgagggaac ggctggaaaa tctgcggaaa     180
aaacccgaga acattccgca accaatctct aacacatcac gcgccaactt gaacaagctg     240
cttacggatt acaccgagat gaaaaaggct attctgcatg tctactggga ggagttccag     300
aaggatcctg tgggactgat gtcgcgcgtt gctcagccgg cgccaaaaaa cattgatcag     360
cggaaattga ttcccgtgaa agatggaaac gagcgcttaa cttcttccgg ctttgcctgc     420
tcacaatgct gccagcccct ctacgtgtac aagcttgagc aagttaacga taagggcaag     480
ccacatacta actactttgg gaggtgcaat gtcagtgagc acgaacgact aattctcctg     540
agccctcata gcccgaggc caatgacgag ctggttacat atagtctagg caagttcggg     600
cagcgggcct tggacttcta ctcgattcac gtgactcgtg agtcaaacca tccggttaag     660
ccgttggagc agataggtgg caatagctgc gcttccggcc cagtgggaaa ggctctgtct     720
gatgcttgta tgggcgcagt tgcgagtttc cttacaaagt atcaggatat aattttggag     780
caccagaaag tcatcaagaa gaacgaaaaa aggctggcaa atctaaaaga tattgcgtcc     840
gccaatggtc tagcatttcc aaaaattaca ctcccgccac aaccgcacac taaggagggg     900
atagaggcat acaacaacgt ggtggctcag attgtgatct gggtaaacct taatctgtgg     960
caaaagctca aaattgggag ggatgaggca aaaccacttc agagattgaa aggatttcct    1020
tccttcccgc ttgtggaacg tcaggctaac gaagtcgatt ggtgggacat ggtttgtaat    1080
gttaagaagc tgatcaacga gaaaaaggaa gatgggaagg tgttttggca gaacttggcg    1140
gggtacaaaa ggcaagaagc cctactcccg tacctgtcaa gtgaagaaga ccgtaaaaag    1200
ggtaagaagt tcgccagata tcagtttgga gatcttctgc tgcacttgga gaagaagcat    1260
ggtgaagatt gggggaaagt ttacgatgag gcctgggagc gaatagataa gaaggttgag    1320
ggtctatcca agcatattaa attggaggag gagcggcgat cggaagacgc ccagtctaag    1380
gcagcactta ctgattggtt gagggcaaaa gcatcttttg tcatcgaagg gctaaaggag    1440
gccgataagg atgaattttg caggtgtgag ctcaaacttc aaaaatggta tggagatctg    1500
agggcaagc cattcgctat cgaggctgag aattctatac ttgatattag cggctttagc    1560
aaacagtata actgcgcatt catctggcaa aaagatggcg ttaaaaagtt gaatctctac    1620
cttattatca attatttcaa gggaggtaaa ttgcggttca agaagatcaa gcctgaagct    1680
tttgaggcca accgtttcta caccgtaatt aataagaaat caggggaaat tgtgccaatg    1740
gaagtaaact tcaattttga cgaccccaac cttatcattc tccccctggc atttgggaag    1800
aggcaagggc gggaattcat ttggaatgat ttactttctc tcgagacagg tagtttgaaa    1860
ctggcaaatg gccgggtgat cgaaaaaaca ctttataatc ggcggacccg acaggatgag    1920
cctgcattgt ttgttgcact cacgtttgaa aggcgagaag tgttagattc atccaacatt    1980
aagccaatga atctcatcgg tattgatcga ggcgagaaca tcccagcagt tattgcactg    2040
accgatccag aagggtgccc cttgtcgagg tttaaggaca gtctgggcaa tccgacacat    2100
atacttcgga taggggaaag ttacaaggag aaacagagaa cgattcaggc agcaaaagag    2160
gttgaacagc gccgcgcagg aggttattcc agaaaatacg ctagcaaagc gaaaaatctt    2220
gccgatgaca tggttcggaa taccgcacgt gacctcctct attatgccgt gacacaagat    2280
gctatgttga tcttcgaaaa cctttcaaga ggattcggca ggcaaggcaa acgcacattt    2340
```

```
atggctgaga  dacagtacac  acgtatggaa  gactggttga  cggccaagct  cgcttatgag   2400
gggctcccct  tccaaaaccta cttgtcgaaa  acgctcgctc  agtacacatc  taagacttgc   2460
tccaactgtg  gtttcacgat  tacctccgcg  gattatgaca  gagtcttgga  gaagttgaaa   2520
aaaactgcca  caggctggat  gactacaata  aatggaaagg  agctgaaggt  gagcatcagc   2580
ttttttcctt  gattcagatc  tcttggtgaa  attcgccaac  tctctacttt  tttgtttctt   2640
ctctaatatt  cctgtgctct  gcttcttgct  gctgctgttc  ttgtgtttac  caggtggagg   2700
gacagattac  gtactataat  cgctacaaaa  ggcagaatgt  agtaaaggac  ctgtccgtgg   2760
agctggatcg  tctgtcggag  gagtcggtta  acaacgacat  ttcatcttgg  accaaagggc   2820
ggagtgggga  agcactttcc  ttgctgaaga  agcgcttttc  ccaccgcccg  gtgcaggaga   2880
aatttgtgtg  cctgaactgt  ggcttcgaga  cccacgcgga  cgagcaggcg  gccctgaaca   2940
tcgcgcgaag  ctggctcttc  ctccgtagcc  aggagtacaa  gaagtaccag  acgaacaaga   3000
caacgggcaa  tacagacaag  cgggcattcg  tggaaacttg  gcagagtttt  tatagaaaga   3060
agttgaagga  ggtctggaaa  ccagccgtgg  gatctaagaa  gagaagaatt  aaacaagat   3119
```

<210> SEQ ID NO 65
<211> LENGTH: 2538
<212> TYPE: DNA
<213> ORGANISM: Artificial
<220> FEATURE:
<223> OTHER INFORMATION: Synthetic polynucleotide. 5' portion of PsCasX_Zm

<400> SEQUENCE: 65

```
atgcaggaga  tcaagagaat  caacaaaatt  cgccggagac  tggtcaagga  ttcgaacacg     60
aagaaggctg  ggaagaccgg  ccctatgaaa  acgctcctgg  taagggtgat  gacaccggac    120
ctgagggaac  ggctggaaaa  tctgcggaaa  aaacccgaga  acattccgca  accaatctct    180
aacacatcac  gcgccaactt  gaacaagctg  cttacggatt  acaccgagat  gaaaaaggct    240
attctgcatg  tctactggga  ggagttccag  aaggatcctg  tgggactgat  gtcgcgcgtt    300
gctcagccgg  cgccaaaaaa  cattgatcag  cggaaattga  ttcccgtgaa  agatggaaac    360
gagcgcttaa  cttcttccgg  ctttgcctgc  tcacaatgct  gccagcccct  ctacgtgtac    420
aagcttgagc  aagttaacga  taagggcaag  ccacatacta  actactttgg  gaggtgcaat    480
gtcagtgagc  acgaacgact  aattctcctg  agccctcata  agcccgaggc  caatgacgag    540
ctggttacat  atagtctagg  caagttcggg  cagcggggcct  tggacttcta  ctcgattcac    600
gtgactcgtg  agtcaaacca  tccggttaag  ccgttggagc  agataggtgg  caatagctgc    660
gcttccggcc  cagtgggaaa  ggctctgtct  gatgcttgta  tgggcgcagt  tgcgagtttc    720
cttacaaagt  atcaggatat  aattttggag  caccagaaag  tcatcaagaa  gaacgaaaaa    780
aggctggcaa  atctaaaaga  tattgcgtcc  gccaatggtc  tagcatttcc  aaaaattaca    840
ctcccgccac  aaccgcacac  taaggagggg  atagaggcat  acaacaacgt  ggtggctcag    900
attgtgatct  gggtaaacct  taatctgtgg  caaaagctca  aaattgggag  ggatgaggca    960
aaaccacttc  agagattgaa  aggatttcct  tccttcccgc  ttgtggaacg  tcaggctaac   1020
gaagtcgatt  ggtgggacat  ggtttgtaat  gttaagaagc  tgatcaacga  gaaaaaggaa   1080
gatgggaagg  tgttttggca  gaacttggcg  gggtacaaaa  ggcaagaagc  cctactcccg   1140
tacctgtcaa  gtgaagaaga  ccgtaaaaag  ggtaagaagt  cgccagata  tcagtttgga   1200 gatcttctgc  tgcacttgga  gaagaagcat  ggtgaagatt  ggggaaagt  ttacgatgag   1260
```

```
gcctgggagc gaatagataa gaaggttgag ggtctatcca agcatattaa attggaggag    1320
gagcggcgat cggaagacgc ccagtctaag gcagcactta ctgattggtt gagggcaaaa    1380
gcatcttttg tcatcgaagg gctaaaggag gccgataagg atgaattttg caggtgtgag    1440
ctcaaacttc aaaaatggta tggagatctg aggggcaagc cattcgctat cgaggctgag    1500
aattctatac ttgatattag cggctttagc aaacagtata actgcgcatt catctggcaa    1560
aaagatggcg ttaaaaagtt gaatctctac cttattatca attatttcaa gggaggtaaa    1620
ttgcggttca agaagatcaa gcctgaagct tttgaggcca accgtttcta caccgtaatt    1680
aataagaaat caggggaaat tgtgccaatg gaagtaaact tcaattttga cgaccccaac    1740
cttatcattc tcccctggc atttgggaag aggcaagggc gggaattcat ttggaatgat    1800
ttactttctc tcgagacagg tagtttgaaa ctggcaaatg gccgggtgat cgaaaaaaca    1860
ctttataatc ggcggacccg acaggatgag cctgcattgt ttgttgcact cacgtttgaa    1920
aggcgagaag tgttagattc atccaacatt aagccaatga atctcatcgg tattgatcga    1980
ggcgagaaca tcccagcagt tattgcactg accgatccag aagggtgccc cttgtcgagg    2040
tttaaggaca gtctgggcaa tccgacacat atacttcgga taggggaaag ttacaaggag    2100
aaacagagaa cgattcaggc agcaaaagag gttgaacagc gccgcgcagg aggttattcc    2160
agaaaatacg ctagcaaagc gaaaaatctt gccgatgaca tggttcggaa taccgcacgt    2220
gacctcctct attatgccgt gacacaagat gctatgttga tcttcgaaaa cctttcaaga    2280
ggattcggca ggcaaggcaa acgcacattt atggctgaga gacagtacac acgtatggaa    2340
gactggttga cggccaagct cgcttatgag gggctcccctt ccaaaaccta cttgtcgaaa    2400
acgctcgctc agtacacatc taagacttgc tccaactgtg gtttcacgat tacctccgcg    2460
gattatgaca gagtcttgga gaagttgaaa aaaactgcca caggctggat gactacaata    2520
aatggaaagg agctgaag                                                 2538
```

<210> SEQ ID NO 66
<211> LENGTH: 396
<212> TYPE: DNA
<213> ORGANISM: Artificial
<220> FEATURE:
<223> OTHER INFORMATION: Synthetic polynucleotide.3' portion of
     PsCasX_Zm

<400> SEQUENCE: 66

```
gtggagggac agattacgta ctataatcgc tacaaaaggc agaatgtagt aaaggacctg      60
tccgtggagc tggatcgtct gtcggaggag tcggttaaca acgacatttc atcttggacc     120
aaagggcgga gtggggaagc actttccttg ctgaagaagc gcttttccca ccgcccggtg     180
caggagaaat ttgtgtgcct gaactgtggc ttcgagaccc acgcggacga gcaggcggcc     240
ctgaacatcg cgcgaagctg gctcttcctc cgtagccagg agtacaagaa gtaccagacg     300
aacaagacaa cgggcaatac agacaagcgg gcattcgtgg aaacttggca gagttttttat     360 agaaagaagt tgaaggaggt ctggaaacca gccgtg                              396
```

<210> SEQ ID NO 67
<211> LENGTH: 116
<212> TYPE: DNA
<213> ORGANISM: Glycine max

```
<400> SEQUENCE: 67
ccagaaaatc ggaaatggac aatctttctt gttacgcaat tctgaatttg cgggttttgg     60
atttggactt ggtcgtcaac acagtctaat taatatcttt ttgctccttc gcttat        116

<210> SEQ ID NO 68
<211> LENGTH: 110
<212> TYPE: DNA
<213> ORGANISM: Glycine max

<400> SEQUENCE: 68
ccagaaaatc ggaaatggac aatctttctt gttacgcaat tctgaatttg cgggttttgg     60
acttggtcgt caacacagtc taattaatat cttttgctc cttcgcttat                110

<210> SEQ ID NO 69
<211> LENGTH: 102
<212> TYPE: DNA
<213> ORGANISM: Glycine max

<400> SEQUENCE: 69
ccagaaaatc ggaaatggac aatctttctt gttacgcaat tctgaatttg cgggttggtc     60
gtcaacacag tctaattaat atcttttgc tccttcgctt at                        102

<210> SEQ ID NO 70
<211> LENGTH: 109
<212> TYPE: DNA
<213> ORGANISM: Glycine max

<400> SEQUENCE: 70
ccagaaaatc ggaaatggac aatctttctt gttacgcaat tctgaatttg cgggtttgga     60
cttggtcgtc aacacagtct aattaatatc tttttgctcc ttcgcttat                109

<210> SEQ ID NO 71
<211> LENGTH: 110
<212> TYPE: DNA
<213> ORGANISM: Glycine max

<400> SEQUENCE: 71
ccagaaaatc ggaaatggac aatctttctt gttacgcaat tctgaatttg cgggttttgg     60
acttggtcgt caacacagtc taattaatat cttttgctc cttcgcttat                110

<210> SEQ ID NO 72
<211> LENGTH: 104
<212> TYPE: DNA
<213> ORGANISM: Glycine max

<400> SEQUENCE: 72
ccagaaaatc ggaaatggac aatctttctt gttacgcaat tctgaatttg cgggacttgg     60
tcgtcaacac agtctaatta atatcttttt gctccttcgc ttat                     104

<210> SEQ ID NO 73
<211> LENGTH: 114
<212> TYPE: DNA
<213> ORGANISM: Glycine max

<400> SEQUENCE: 73
ccagaaaatc ggaaatggac aatctttctt gttacgcaat tctgaatttg cgggttttgg     60
ttggacttgg tcgtcaacac agtctaatta atatcttttt gctccttcgc ttat          114
```

<210> SEQ ID NO 74
<211> LENGTH: 146
<212> TYPE: DNA
<213> ORGANISM: Glycine max

<400> SEQUENCE: 74
agaaaaaggc tgagaagaag ctcagcggtt ggggcttgtt tggctccaag tatgaagatg    60
ccgccgatct cttcgataaa gccgccaatt gcttcaagct cgccaaatca tgttttcct   120 ctttctctct actttttta aattcc                                        146

<210> SEQ ID NO 75
<211> LENGTH: 120
<212> TYPE: DNA
<213> ORGANISM: Glycine max

<400> SEQUENCE: 75
agaaaaaggc tgagaagaag ctcagcggtt ggggcttgtt tggctccaag tatgaagatg    60
ccgccgatct cttctcgcca aatcatgttt ttcctctttc tctctacttt ttttaaatt   120

<210> SEQ ID NO 76
<211> LENGTH: 133
<212> TYPE: DNA
<213> ORGANISM: Glycine max

<400> SEQUENCE: 76
agaaaaaggc tgagaagaag ctcagcggtt ggggcttgtt tggctccaag tatgaagatg    60
ccgccgatct cttcgataaa gccgccatcg ccaaatcatg ttttcctct ttctctctac   120 ttttttaaa ttc                                                      133

<210> SEQ ID NO 77
<211> LENGTH: 146
<212> TYPE: DNA
<213> ORGANISM: Glycine max

<400> SEQUENCE: 77
cttacgtagt agttttttgt cccacaaaat gaattttgca tgtattcagt gcttccttct    60
tcggcttcac ttttctggc cggtgcagcc ggtaaccagt agtcatattt ggatgttaaa   120
gagacagaaa atcttaatca ccgctc                                       146

<210> SEQ ID NO 78
<211> LENGTH: 130
<212> TYPE: DNA
<213> ORGANISM: Glycine max

<400> SEQUENCE: 78
cttacgtagt agttttttgt cccacaaaat gaattttgca tgtattcagt gcttccttct    60
ggccggtggc agccggtaac cagtagtcat atttggatgt taaagagaca gaaaatctta   120
atcaccgctc                                                         130

<210> SEQ ID NO 79
<211> LENGTH: 2961
<212> TYPE: DNA
<213> ORGANISM: Artificial
<220> FEATURE:
<223> OTHER INFORMATION: Synthetic polynucleotide. DsCasX_Gm2
      (Deltaproteobacteria sp. CasX codon optimized for Soy)

<400> SEQUENCE: 79

```
atggagaaac gcatcaacaa gatacgcaag aagctctccg ctgataacgc cacaaaaccc      60
gtctcacgct ctggccctat gaagacactg cttgtccgcg taatgacaga cgatctcaag     120
aagcgattgg aaaagcgacg caaaaagccg gaagtgatgc cacaagtgat ctcaaacaat     180
gcggccaaca accttcggat gctcctcgac gattacacaa agatgaagga agctatccta     240
caagtgtact ggcaagagtt caagacgat catgttggct tgatgtgcaa attcgctcaa     300
ccagcctcca agaaaattga ccaaaacaaa ctcaaaccag aaatggacga aagggcaat     360
cttactactg ctggattcgc ttgctctcaa tgtggtcagc ccttgttcgt ttacaagcta     420
gagcaagtaa gcgaaaaggg caaagcctat acgaactact tcggccggtg taatgtggca     480
gagcacgaga aactaatcct gttggcccag ctaaagcctg aaaaggatag cgacgaggct     540
gttacctata gtctcgggaa attcggacaa agggcgttgg acttttactc tattcatgtg     600
actaaggagt ccactcaccc agtaaaacct ttagctcaaa tagctggcaa tcgttatgcc     660
tctgggccag ttgggaaagc tctttccgat gcctgcatgg aacaatcgc cagctttctc     720
tcaaagtacc aggacatcat aattgaacac caaaaggttg ttaaagggaa tcagaagcgt     780
ctggaatcat tgagggaact ggccgggaag gagaatttgg aatacccag tgtcaccta     840
cctcctcaac ctcacacaaa ggaaggcgtg gacgcctaca cgaggtgat tgctcgcgtg     900
aggatgtggg tgaatcttaa cctctggcag aagttaaagc tctcaaggga tgacgctaag     960
cctttactcc gattgaaggg gtttccctcg tttccggtgg ttgaaagacg tgaaaacgaa    1020
gtggattggt ggaacacgat taacgaagtc aagaagctga ttgatgccaa gcgtgatatg    1080
ggtcgagtgt tctggagcgg tgttactgcc gaaaagcgca acactatcct tgaaggttac    1140
aactatcttc cgaacgagaa cgaccacaag aagcgcgagg gttcactcga aaatcccaag    1200
aagccagcta acgacagtt cggagaccct ctgctttatc ttgagaagaa atacgctggg    1260
gattggggaa aggtcttcga cgaagcctgg gagcgaattg acaaaaagat cgctggactt    1320
acctcccaca tcgaaaggga ggaagcacgt aatgctgagg atgctcagag taaggcagtg    1380
cttacagatt ggctccgggc aaaagcgtca ttcgttcttg aaagattgaa ggagatggat    1440
gagaaggagt tctacgcttg tgagatccaa ttacagaagt ggtatggaga cttgcgtgga    1500
aaccctttcg cagtcgaggc cgagaaccgc gtcgtggaca tctcagggtt ttcaatcggt    1560
agtgacggcc atagcatcca atatcggaac ttactagcat ggaaatacct tgagaatgga    1620
aaacgcgagt tctacttgct tatgaactac ggcaagaaag gacgaatacg tttcacagat    1680
gggaccgaca tcaaaaaatc agggaaatgg caagggttgc tttatggagg tggcaaagca    1740
aaagttattg atcttacatt cgatccagac gatgaacagc ttatcatact ccctctagca    1800
ttcggaaccc gacaaggccg agagtttatc tggaacgatc tattgagcct ggaaacaggg    1860
ctcattaagc tcgctaatgg tagagtgatc gaaaaaacaa tctacaacaa gaaaatcggt    1920
cgtgacgagc cagcccttt cgtggctctt acgtttgaaa ggagggaagt cgttgatccg    1980
agcaacatca agccggtcaa cctcataggg gtggatagag gcgagaacat tccggcggtt    2040
attgctttaa cagatccaga gggatgtcct ctgcctgagt ttaaagacag tagtggagga    2100
ccaacggata ttctccgcat tggcgaaggc tacaaggaga acaacgcgc aatccaagct    2160
gcaaaggaag ttgaacagcg gcgtgctggt ggatactcac gcaaattcgc atctaagtct    2220
cggaacctgg cagatgatat ggtcaggaat agtgctcgtg acctgttcta tcatgctgtt    2280
actcacgacg ccgttctcgt attcgaaaac ctgtcacgcg gattcgggag acaggggaaa    2340
```

```
cggacattca tgactgaacg tcaatatacc aagatggaag actggctcac cgctaagctg    2400
gcgtacgaag gacttacatc caaaacctat ctatctaaaa ctctggctca atatacttcc    2460
aagacttgct ctaattgcgg tttcacaatt actactgccg actacgatgg catgttggtg    2520
aggctcaaga agacatctga tggttgggca accacactta caacaagga gcttaaagca    2580 gagggacaga tcacttacta caatcgctac aaaaggcaaa ctgtggagaa ggaactgtct    2640
gccgaattgg acagactcag cgaggaatcg ggcaataacg cacatctcaaa atggactaag    2700 ggccgccgtg atgaggccct ctttctactc aaaaaacggt tcagccatag gccagtccaa    2760
gaacagttcg tatgccttga ctgcggacac gaggttcatg ctgatgaaca ggctgccttg    2820
aacatcgcta gatcatggct gttccttaac tcgaactcaa ctgagtttaa aagctacaag    2880
tccggaaagc aacctttcgt aggagcttgg caagcgtttt acaaaaggag acttaaggag    2940
gtctggaaac ctaacgcata a                                              2961

<210> SEQ ID NO 80
<211> LENGTH: 2961
<212> TYPE: DNA
<213> ORGANISM: Artificial
<220> FEATURE:
<223> OTHER INFORMATION: Synthetic polynucleotide.
      DsCasX_M1(Deltaproteobacteria sp. CasX codon optimized for
      Monocots)

<400> SEQUENCE: 80
atggagaaac gcatcaataa gatccgcaag aaactctctg ccgataatgc tactaaacct      60
gtttcgcggt caggcccgat gaagacctta ctggtccgag ttatgactga cgacctcaaa     120
aaacgattgg agaagcgccg caaaaagccg gaagttatgc cacaagtaat cagcaacaat     180
gcggccaata acctccgaat gttactggat gactacacaa agatgaagga ggctatactc     240
caagtctatt ggcaagagtt taaagacgac cacgttggcc tcatgtgcaa attcgcccaa     300
cccgccagca aaagattga ccaaaacaaa cttaaaccgg agatgacga aaagggcaac     360 ctgacaacgg cgggtttcgc gtgttcacaa tgtggacagc ctctgttcgt gtacaagcta     420
gagcaagtta gtgaaaaggg caaagcctat acgaattact cgggagggtg taacgttgct     480
gagcacgaga agttaatcct actggcccaa ctcaaacctg aaaaggatag cgacgaagct     540
gttacttatt cacttgggaa attcggtcaa cgggctctgg acttctactc cattcatgtt     600
actaaggaat cgactcaccc ggttaaacca ttggcacaga tcgctgggaa ccggtatgca     660
agtggccctg ttgaaaaagc tctttctgac gcctgcatgg gcactattgc ctcattctta     720
agcaaatacc aagacataat cattgaacac cagaaggttg tgaagggcaa tcagaaaagg     780
cttgagtcat tgcgtgaatt ggctgggaag gagaacttgg aatatccatc tgtcacactg     840
ccaccacaac cacatacaaa ggaaggcgtc gatgcctaca acgaggttat cgcccgtgta     900
cgcatgtggg tgaacctaaa cttatggcag aagctcaagt tgtcacgtga tgacgccaaa     960
cccctattga gacttaaggg ttttccgtcc tttccagtgg tggaacgtag ggagaacgaa    1020
gtggattggt ggaacactat caacgaagtc aaaaaactga ttgacgctaa cgcgacatg     1080 ggacgggtgt tctggagcgg cgttacggct gagaagcgaa acacgatact cgaaggttac    1140
aactacctcc caaacgaaaa cgaccacaag aagcgggagg cagtttgga gaaccccaaa     1200 aaaccgctca acggcagtt cgggacttac tactatacc ttgagaagaa gtacgctggg    1260 gattgggca aggtcttcga cgaagcgtgg gaacgtatcg acaagaaaat cgccggactt    1320
actagccaca ttgaacgcga ggaggcacgg aatgccgagg acgctcagtc taaagcggtt    1380
```

```
cttactgact ggctgcgggc aaaagcctct ttcgttcttg aacgccttaa ggagatggac      1440
gaaaaggagt tttacgcttg tgagatccag ttacagaagt ggtacgggga cttgcgcggc      1500
aatccgttcg ctgttgaagc tgaaaaccgc gtggttgaca taagtggctt ctccatcggc      1560
agcgatgggc attcaattca atatcgcaat ctgttggcat ggaaatacct ggagaatggc      1620
aaacgcgagt tctatctact gatgaactac ggcaaaaaag gtcgtattcg gtttacggat      1680
ggtactgata tcaagaagtc cggaaaatgg caaggcttgc tttatggagg tggcaaagca      1740
aaagttattg acctcacctt cgacccagat gatgagcagc tcattatcct gccgctggca      1800
ttcggtactc gacaagggcg tgagtttatc tggaacgacc tattgtcgct tgagaccggg      1860
ctcattaagc tcgccaacgg ccgtgtaatc gaaaaaacta tctacaacaa gaaaatcggc      1920
cgagatgaac ctgcactatt cgtagcgttg acgttcgaaa gacgtgaggt cgtcgatccg      1980
agtaacatta agccggttaa tctcataggt gttgatcggg gtgagaacat tcccgctgta      2040
atcgctctga cagatccaga gggatgtcct ctgccggagt tcaaagactc atcaggcgga      2100
cctacagata ttctgcggat aggtgaaggg tacaaggaga acaacgcgc catccaagca       2160 gcgaaggaag ttgaacaacg tagagctggt ggatattcta ggaaattcgc ctctaagagt      2220
cgcaatcttg ccgatgatat ggttcgaaat tccgcgcgcg acctattcta tcacgccgtt      2280
actcacgatg ctgttctcgt atttgaaaac ttatccaggg gtttcggaag acagggaaaa      2340
cgaacgttta tgacggaacg ccaatataca aagatggaag actggcttac agctaaactc      2400
gcctatgagg gcctcacaag caaaacatac ctctctaaaa ctttggcaca gtataccagc      2460
aagacgtgct cgaattgcgg cttcacgatt acaaccgccg actatgatgg aatgctcgtg      2520
cgcctcaaga gacgtcaga cggctgggca actaccctca acaacaagga attgaaagcg       2580
gaaggtcaaa ttacctatta caatcggtac aaaaggcaga ctgttgaaaa ggaactgtcg      2640
gcggagttag accggttgag cgaggaatct gggaacaacg acattagcaa atggactaaa      2700
ggccgtaggg acgaagcact cttcctgctc aaaaaacgct tttcgcatcg accagtgcaa      2760
gaacagtttg tctgtctgga ctgtggccat gaggtccacg ccgatgaaca agcggcactt      2820
aacatcgctc gttcatggct gttcctcaac tcaaattcga ccgagttcaa gagctacaaa      2880
tcaggaaagc agccgttcgt tggagcatgg caagcctttt acaagcgtcg gctaaaggaa      2940
gtgtggaagc ctaacgctta a                                                2961
```

<210> SEQ ID NO 81
<211> LENGTH: 33
<212> TYPE: DNA
<213> ORGANISM: Solanum tuberosum

<400> SEQUENCE: 81

```
atgggtagca aaaagaggcg tatcaagcag gac                                     33
```

<210> SEQ ID NO 82
<211> LENGTH: 30
<212> TYPE: DNA
<213> ORGANISM: Solanum lycopersicum

<400> SEQUENCE: 82

```
ggatctaaga agcgtaggat caagcaagat                                         30
```

<210> SEQ ID NO 83
<211> LENGTH: 289
<212> TYPE: DNA
<213> ORGANISM: Medicago truncatula

<400> SEQUENCE: 83
gggtcttagt ttacttttct tgatttgtaa tgtacaatgg ggctgtggtg tttatatttc    60
atttaatcgt taatgtacta ctttatacta gttgtttata tttaaaaaag cataaacttt   120
gcctcatcta aatgtacttg aattgagttt acttagaagt gcttgaattg agtttgtgta   180
aatgaacata attttagtag tgcttagatt aagttcacat atcactactt tataccaggg   240
gattactatt cttttagct tttgttttta ctgttggttt tttgccaaa                289

<210> SEQ ID NO 84
<211> LENGTH: 134
<212> TYPE: DNA
<213> ORGANISM: Glycine max
<220> FEATURE:
<221> NAME/KEY: misc_feature
<222> LOCATION: (1)..(134)
<223> OTHER INFORMATION: Fragment of Sequence 74 from position 13 to 146

<400> SEQUENCE: 84
agaagaagct cagcggttgg ggcttgtttg gctccaagta tgaagatgcc gccgatctct    60
tcgataaagc cgccaattgc ttcaagctcg ccaaatcatg ttttcctct ttctctctac    120 ttttttttaaa ttcc                                                    134

<210> SEQ ID NO 85
<211> LENGTH: 108
<212> TYPE: DNA
<213> ORGANISM: Glycine max
<220> FEATURE:
<221> NAME/KEY: misc_feature
<222> LOCATION: (1)..(108)
<223> OTHER INFORMATION: Fragment of Sequence 75 from position 13 to 120

<400> SEQUENCE: 85
agaagaagct cagcggttgg ggcttgtttg gctccaagta tgaagatgcc gccgatctct    60
tctcgccaaa tcatgttttt cctctttctc tctactttt tttaaatt                 108

<210> SEQ ID NO 86
<211> LENGTH: 121
<212> TYPE: DNA
<213> ORGANISM: Glycine max
<220> FEATURE:
<221> NAME/KEY: misc_feature
<222> LOCATION: (1)..(121)
<223> OTHER INFORMATION: Fragment of Sequence 76 from position 13 to 133

<400> SEQUENCE: 86
agaagaagct cagcggttgg ggcttgtttg gctccaagta tgaagatgcc gccgatctct    60
tcgataaagc cgccatcgcc aaatcatgtt tttcctcttt ctctctactt tttttaaatt   120
c                                                                  121

<210> SEQ ID NO 87
<211> LENGTH: 130
<212> TYPE: DNA
<213> ORGANISM: Glycine max
<220> FEATURE:
<221> NAME/KEY: misc_feature
<222> LOCATION: (1)..(130)
<223> OTHER INFORMATION: Fragment of Sequence 77 from position 17 to 146

```
<400> SEQUENCE: 87
ttgtcccaca aaatgaattt tgcatgtatt cagtgcttcc ttcttcggct tcactttttc      60
tggccggtgc agccggtaac cagtagtcat atttggatgt taaagagaca gaaaatctta    120
atcaccgctc                                                            130

<210> SEQ ID NO 88
<211> LENGTH: 114
<212> TYPE: DNA
<213> ORGANISM: Glycine max
<220> FEATURE:
<221> NAME/KEY: misc_feature
<222> LOCATION: (1)..(114)
<223> OTHER INFORMATION: Fragment of Sequence 78 from position 17 to 130

<400> SEQUENCE: 88
ttgtcccaca aaatgaattt tgcatgtatt cagtgcttcc ttctggccgg tggcagccgg      60
taaccagtag tcatatttgg atgttaaaga gacagaaaat cttaatcacc gctc          114
```